United States Patent
Stamatoyannopoulos et al.

(10) Patent No.: US 11,900,600 B2
(45) Date of Patent: Feb. 13, 2024

(54) METHODS OF ANALYZING MICROSCOPY IMAGES USING MACHINE LEARNING

(71) Applicant: Altius Institute for Biomedical Sciences, Seattle, WA (US)

(72) Inventors: John A. Stamatoyannopoulos, Seattle, WA (US); Shreeram Akilesh, Seattle, WA (US); Alexander Muratov, Seattle, WA (US); Wouter Meuleman, Seattle, WA (US); William Kerwin, Seattle, WA (US)

(73) Assignee: Altius Institute for Biomedical Sciences, Seattle, WA (US)

( * ) Notice: Subject to any disclaimer, the term of this patent is extended or adjusted under 35 U.S.C. 154(b) by 0 days.

(21) Appl. No.: 18/045,342

(22) Filed: Oct. 10, 2022

(65) Prior Publication Data

US 2023/0274423 A1    Aug. 31, 2023

Related U.S. Application Data

(63) Continuation of application No. 16/630,090, filed as application No. PCT/US2018/042964 on Jul. 19, 2018, now Pat. No. 11,501,429.

(Continued)

(51) Int. Cl.
*G06T 7/00* (2017.01)
*G06N 20/00* (2019.01)
(Continued)

(52) U.S. Cl.
CPC ........... *G06T 7/0012* (2013.01); *G06N 20/00* (2019.01); *G16B 40/20* (2019.02); *G16B 40/30* (2019.02);
(Continued)

(58) Field of Classification Search
CPC ......... G06T 7/155; G06T 7/162; G06T 7/187; G06T 7/215; G06T 7/64; G06T 7/73; G06T 2207/10056; G06T 2207/30242; G06T 7/0008; G06T 7/20; G06T 2200/24; G06T 2207/20012; G06T 2207/20216; G06T 2207/30164; G06T 2207/30196; G06T 5/005; G06T 5/50; G06T 7/0006; G06T 7/0014; G06T 7/136; G06T 7/60;
(Continued)

(56) References Cited

U.S. PATENT DOCUMENTS 7,062,076 B1   6/2006  Osborne et al.
2012/0220022 A1*  8/2012  Ehrlich ................. G01N 15/14
                                              435/286.2

(Continued)

FOREIGN PATENT DOCUMENTS

WO    2013082123    6/2013
WO    2013113707    8/2013

OTHER PUBLICATIONS

Raja et al., (2013) "Automated image analysis and inference of gene function from high—Content screens", Eurasip, 1-5.
(Continued)

*Primary Examiner* — Ajibola A Akinyemi
(74) *Attorney, Agent, or Firm* — Bozicevic, Field & Francis LLP; Shweta Chandra

(57) ABSTRACT

Disclosed herein are methods of utilizing machine learning methods to analyze microscope images of populations of cells.

20 Claims, 27 Drawing Sheets

Related U.S. Application Data

(60) Provisional application No. 62/534,679, filed on Jul. 19, 2017.

(51) Int. Cl.
  *G16B 40/30* (2019.01)
  *G16B 40/20* (2019.01)

(52) U.S. Cl.
  CPC .............. *G06T 2207/20081* (2013.01); *G06T 2207/20084* (2013.01); *G06T 2207/30024* (2013.01)

(58) Field of Classification Search
  CPC ........... G06T 11/60; G06T 2207/10004; G06T 2207/10016
  USPC ........................................................ 382/128
  See application file for complete search history.

(56) References Cited

U.S. PATENT DOCUMENTS

| | | |
|---|---|---|
| 2012/0244532 A1 | 9/2012 | Craighead et al. |
| 2016/0314580 A1 | 10/2016 | Lloyd et al. |
| 2017/0132362 A1* | 5/2017 | Skinner .................. G16B 30/00 |
| 2018/0228460 A1 | 8/2018 | Singh et al. |
| 2019/0246929 A1* | 8/2019 | Angle .................. A61B 5/7282 |

OTHER PUBLICATIONS

Zhou et al., (2008) "Computational Systems Bioinformatics and Bioimaging for Pathway Analysis and Drug Screening", Proceedings Of The Ieee, (96)8:1310-1331.

* cited by examiner

METHODS OF ANALYZING MICROSCOPY IMAGES USING MACHINE LEARNING

CROSS-REFERENCE

This application claims the benefit of U.S. Provisional Application No. 62/534,679, filed on Jul. 19, 2017, which application is incorporated herein by reference.

BACKGROUND

Large populations of cell can be difficult to screen and characterize efficiently, especially when screening for the purpose of identifying subtle phenotypic differences between cells. High-resolution imaging of cells can provide a wealth of cell phenotype data, however, the interpretation of such data is complex as well as difficult to correlate with the detailed molecular genetic data provided by modern sequencing techniques. Accordingly, there is an unmet need for new methods that facilitate the interpretation of high-resolution cell imaging data.

SUMMARY

Disclosed herein are methods and systems for using statistical and/or machine learning techniques to analyze images of cells or sub-cellular structures for the purpose of identifying a set of key cell attributes that may be used, for example, to: (i) characterize individual cells, sub-populations of cells, or entire populations of cells, (ii) discriminate between cells or cell populations that exhibit subtle differences in their phenotypic traits, e.g., in response to a physical or chemical stimulus, a genetic mutation, or an environmental change, and (iii) correlate cell phenotypic traits, or changes thereof, to biochemical, physiological, genetic, epigenetic, genomic, or other types of bioassay and nucleic acid sequencing data.

Disclosed herein are methods for identifying a genetic, epigenetic, or genomic trait in a cell sample, the method comprising: a) capturing a series of one or more images of the cell sample; and b) processing the series of one or more images using a machine learning algorithm to identify one or more cell phenotypic traits that are correlated with the genetic, epigenetic, or genomic trait; wherein the machine learning algorithm has been trained using a training data set that comprises cell image data and nucleic acid sequence data.

In some embodiments, the one or more cell phenotypic traits comprise one or more observable phenotypic traits. In some embodiments, the one or more observable phenotypic traits comprise one or more of cell shape or morphology, size, texture, internal structure, patterns of distribution of one or more specific proteins, glycosylated proteins, nucleic acid molecules, lipid molecules, glycosylated lipid molecules, carbohydrate molecules, metabolites, ions, or any combination thereof. In some embodiments, the one or more cell phenotypic traits comprise one or more latent variables or traits that are not directly observable in the series of one or more images. In some embodiments, the machine learning algorithm comprises an unsupervised machine learning algorithm. In some embodiments, the unsupervised machine learning algorithm comprises an artificial neural network, an association rule learning algorithm, a hierarchical clustering algorithm, a cluster analysis algorithm, a matrix factorization approach, a dimensionality reduction approach, or any combination thereof. In some embodiments, the unsupervised machine learning algorithm is an artificial neural network comprising an autoencoder, a stacked autoencoder, a denoising autoencoder, a variational autoencoder, or any combination thereof. In some embodiments, the autoencoder, stacked autoencoder, denoising autoencoder, variational autoencoder, or any combination thereof, is used to determine a set of one or more latent variables that comprise a compressed representation of one or more key cell attributes. In some embodiments, the autoencoder, stacked autoencoder, denoising autoencoder, variational autoencoder, or any combination thereof, is used to perform generative modeling to predict a change in one or more cell phenotypic, genotypic, epigenotypic, or genomic traits based on a change in one or more latent variables. In some embodiments, a set of predictions derived from the generative model is used to design a regulatory agent that targets a genetic, epigenetic, or genomic abnormality. In some embodiments, the training data set further comprises gene expression data or DNase I hypersensitivity assay data. In some embodiments, the training data set incorporates one or more constraints on a state of the cells in the sample. In some embodiments, the cell sample comprises a single cell. In some embodiments, the cell sample comprises a plurality of cells. In some embodiments, the series of one or more images are captured using a super-resolution fluorescence microscopy technique.

Also disclosed herein are cell characterization systems comprising: a) a pre-processing module configured to identify one or more regions of interest within a series of one or more images, wherein each image of the series comprises an image of one or more cells from a population of cells; and b) an analysis module configured to receive an output data set from the pre-processing module and apply a series of one or more transformations to the output data to generate a cell characterization data set, wherein the cell characterization data set comprises a basis representation of one or more key attributes of cells within the population.

In some embodiments, the cell characterization data set is of lower dimensionality than that of the output data set from the pre-processing module. In some embodiments, the cell characterization data set comprises a representation of one or more key attributes of a single cell or of a sub-population of cells within the population. In some embodiments, the one or more key attributes of the cells comprise one or more latent variables or traits. In some embodiments, the one or more key attributes of the cells comprise one or more observable phenotypic traits. In some embodiments, the one or more observable phenotypic traits comprise cell shape or morphology, size, texture, internal structure, patterns of distribution of one or more specific proteins, glycosylated proteins, nucleic acid molecules, lipid molecules, glycosylated lipid molecules, carbohydrate molecules, metabolites, ions, or any combination thereof. In some embodiments, the analysis module is configured to execute one or more of the following statistical or machine learning algorithms to implement the series of one or more transformations: a probabilistic graphical model, a regression analysis model, an eigenvector-based analysis, a supervised machine learning algorithm, a semi-supervised machine learning algorithm, or an unsupervised machine learning algorithm. In some embodiments, the analysis module is configured to execute an eigenvector-based analysis comprising a principle component analysis of the output data set. In some embodiments, the analysis module is configured to execute a regression analysis model comprising L1 regularization or L2 regularization. In some embodiments, the analysis module is configured to execute a supervised machine learning algorithm comprising an artificial neural network, a decision tree, a logistical model tree, a Random Forest, a support vector machine, or any combination thereof. In some embodiments, the analysis module is configured to execute an unsupervised machine learning algorithm comprising an artificial neural network, an association rule learning algorithm, a hierarchical clustering algorithm, a cluster analysis algorithm, a matrix factorization approach, a dimensionality reduction approach, or any combination thereof. In some embodiments, the supervised or unsupervised machine learning algorithm is trained using a training data set that incorporates one or more constraints on cell population state. In some embodiments, the supervised or unsupervised machine learning algorithm is trained using a training data set that incorporates DNase I hypersensitivity assay data, nucleic acid sequencing data, or gene expression profiling data, or any combination thereof for one or more cells of the cell population. In some embodiments, nucleic acid sequencing data or gene expression profiling data for one or more cells of the cell population is used as additional input for the analysis module. In some embodiments, the one or more key attributes of the cells comprise one or more phenotypic traits, genotypic traits, epigenotypic traits, genomic traits, or any combination thereof. In some embodiments, the one or more genotypic traits comprise a single nucleotide polymorphism (SNP), an insertion mutation, a deletion mutation, a repeat sequence, or any combination thereof. In some embodiments, the one or more genomic traits comprise a gene expression level, a gene activation level, a gene suppression level, a chromatin accessibility level, or any combination thereof. In some embodiments, the one or more key attributes identified by the analysis module are used to identify correlations between phenotypic traits, genotypic traits, and genomic traits. In some embodiments, the supervised or unsupervised machine learning algorithm is continuously updated using new training data. In some embodiments, the new training data is drawn from a training database that resides on the internet or in the cloud. In some embodiments, the analysis module is configured to execute an unsupervised machine learning algorithm comprising an artificial neural network, and wherein the artificial neural network comprises an autoencoder, a stacked autoencoder, a denoising autoencoder, a variational autoencoder, a deep learning neural network, a deep belief network, or any combination thereof. In some embodiments, the artificial neural network is a deep learning neural network, and wherein the deep learning neural network is a deep convolutional generative adversarial network (DCGAN). In some embodiments, the series of one or more images comprise phase contrast, fluorescence, super-resolution fluorescence, or electron microscopy images. In some embodiments, the pre-processing module is configured to identify the one or more regions of interest by applying one or more image processing algorithms to the series of one or more images. In some embodiments, the one or more image processing algorithms comprise a flat-field correction algorithm, a noise removal algorithm, an aberration correction algorithm, or any combination thereof. In some embodiments, the one or more regions of interest are identified through the use of an edge detection algorithm, a corner detection algorithm, a blob detection algorithm, a ridge detection algorithm, a scale-invariant feature transform, a thresholding algorithm, a template matching algorithm, a linear Hough transform, a circular Hough transform, a generalized Hough transform, or any combination thereof. In some embodiments, the cell characterization data set is use to detect an effect of a change in environmental condition on cells of the population. In some embodiments, the cell characterization data set is used to detect an effect of an exposure to a chemical compound on cells of the population. In some embodiments, the chemical compound is a drug or drug candidate. In some embodiments, a decoder portion of the autoencoder, stacked autoencoder, denoising autoencoder, or variational autoencoder is used to perform generative modeling to predict changes in one or more cell phenotypic, genotypic, epigenotypic, or genomic traits based on changes in one or more latent variables identified by the autoencoder, stacked autoencoder, denoising autoencoder, or variational autoencoder, and information obtained therefrom is used to design a tissue-restricted, environmentally-responsive regulatory element.

Disclosed herein are methods for characterizing a population of cells, the method comprising: a) acquiring a series of one or more images of a population of cells, wherein at least one image of the series comprises an image of one or more cells; and b) processing the series of one or more images using a statistical or machine learning algorithm, wherein the statistical or machine learning algorithm generates a cell characterization data set that comprises a basis representation of one or more key attributes of cells within the population of cells.

In some embodiments, the method further comprises making a cell classification decision based on the cell characterization data set.

Disclosed herein are methods for screening drug candidates, the method comprising: a) acquiring a series of one or more images of a population of cells both before and after contacting the cells with a drug candidate, wherein at least one image of the series comprises an image of one or more cells, b) separately processing the series of one or more images acquired before and after the contacting step using a statistical or machine learning algorithm, wherein the statistical or machine learning algorithm generates a cell characterization data set for each series that comprises a basis representation of one or more key attributes of cells within the population of cells; and c) comparing the cell characterization data set for the population of cells after contacting with the drug candidate to that for the population of cells before contacting with the drug candidate, wherein detection of a change in the cell characterization data set indicates that the drug candidate activates or inactivates an intracellular signaling pathway that affects at least one key attribute of cells within the population of cells.

In some embodiments, the series of one or more images are acquired using phase contrast microscopy, fluorescence microscopy, super-resolution fluorescence microscopy, electron microscopy, or other super-resolution imaging technique. In some embodiments, the processing steps further comprise applying a flat-field correction algorithm, a noise removal algorithm, an aberration correction algorithm, or any combination thereof to the images in each series of images. In some embodiments, the processing steps further comprise applying one or more image processing algorithms to identify one or more regions of interest in the images of each series of images. In some embodiments, the statistical or machine learning algorithm comprises a probabilistic graphical model, a regression analysis model, an eigenvector-based analysis, a supervised machine learning algorithm, a semi-supervised machine learning algorithm, or an unsupervised machine learning algorithm. In some embodiments, the statistical or machine learning algorithm comprises an eigenvector-based analysis, and wherein the eigenvector-based analysis comprises a principle component analysis of processed image data. In some embodiments, the statistical or machine learning algorithm comprises a regression analysis model, and wherein the regression analysis model further comprises use of L1 regularization or L2 regularization. In some embodiments, the statistical or machine learning algorithm comprises a supervised machine learning algorithm, and wherein the supervised machine learning algorithm comprises an artificial neural network, a decision tree, a logistical model tree, a Random Forest, a support vector machine, or any combination thereof. In some embodiments, the statistical or machine learning algorithm comprises an unsupervised machine learning algorithm, and wherein the unsupervised machine learning algorithm comprises an artificial neural network, an association rule learning algorithm, a hierarchical clustering algorithm, a cluster analysis algorithm, a matrix factorization approach, a dimensionality reduction approach, or any combination thereof. In some embodiments, the supervised or unsupervised machine learning algorithm is trained using a training data set that incorporates one or more constraints on cell population state. In some embodiments, the supervised or unsupervised machine learning algorithm is trained using a training data set that incorporates nucleic acid sequencing data, gene expression profiling data, DNase I hypersensitivity assay data, or any combination thereof for one or more cells of the cell population. In some embodiments, nucleic acid sequencing data or gene expression profiling data for one or more cells of the cell population is used as additional input for the statistical or machine learning algorithm. In some embodiments, the supervised or unsupervised machine learning algorithm is continuously updated using new training data. In some embodiments, the new training data is drawn from a training database that resides on the internet or in the cloud. In some embodiments, the unsupervised machine learning algorithm comprises an artificial neural network, and wherein the artificial neural network comprises an autoencoder, a stacked autoencoder, a denoising autoencoder, a variational autoencoder, a deep learning neural network, a deep belief network, or any combination thereof. In some embodiments, the cell characterization data set is of lower dimensionality than that of image data used as input for the statistical or machine learning algorithm. In some embodiments, the cell characterization data set comprises a representation of one or more key attributes of a single cell or of a sub-population of cells within the population. In some embodiments, the one or more key attributes of the cells comprise one or more latent variables or traits. In some embodiments, the one or more key attributes of the cells comprise one or more observable phenotypic traits. In some embodiments, the one or more key attributes of the cells comprise one or more observable phenotypic traits, genotypic traits, epigenetic traits, genomic traits, or any combination thereof. In some embodiments, the one or more observable phenotypic traits comprise external shape, color, size, internal structure, patterns of distribution of one or more specific proteins, patterns of distribution of chromatin structure, glycosylated proteins, nucleic acid molecules, lipid molecules, glycosylated lipid molecules, carbohydrate molecules, metabolites, ions, or any combination thereof. In some embodiments, the one or more genotypic traits comprise a single nucleotide polymorphism (SNP), an insertion mutation, a deletion mutation, a repeat sequence, or any combination thereof. In some embodiments, the one or more genomic traits comprise a gene expression level, a gene activation level, a gene suppression level, a chromatin accessibility level, or any combination thereof. In some embodiments, the cell characterization data set is used to detect an effect of a change in environmental condition on cells of the population. In some embodiments, the cell characterization data set is used to detect an effect of an exposure to a chemical compound on cells of the population. In some embodiments, the chemical compound is a drug or drug candidate. In some embodiments, the cell characterization data set is used to detect a disease state in cells of the population. In some embodiments, the method further comprises: d) acquiring a series of one or more images of a population of cells both before and after independently contacting the cells with a plurality of drug candidates, wherein at least one image of the series comprises an image of one or more cells; e) separately processing the series of one or more images acquired before and after the independently contacting step for each drug candidate of the plurality of drug candidates using a statistical or machine learning algorithm, wherein the statistical or machine learning algorithm generates a cell characterization data set for each series that comprises a basis representation of one or more key attributes of cells within the population of cells; f) comparing the cell characterization data set for the population of cells after independently contacting the cells with the plurality of drug candidates to that for the population of cells before independently contacting the cells with the plurality of drug candidates, wherein detection of a change in the cell characterization data set indicates that a drug candidate of the plurality of drug candidates activates or inactivates an intracellular signaling pathway that affects at least one key attribute of cells within the population of cells; and g) selecting the drug candidate to be used as therapeutic drug based on a comparison of the characterization data set of the drug candidate with characterization data sets of the plurality of drug candidates.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
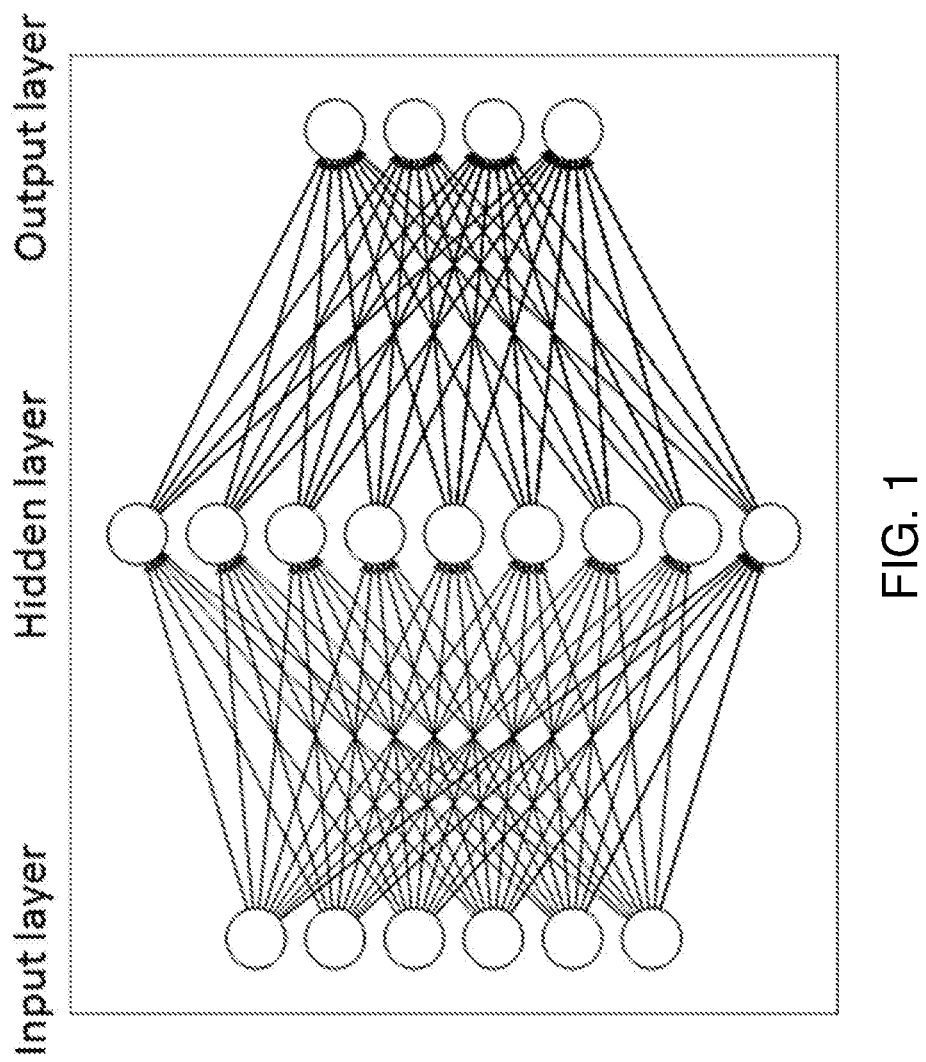
FIG. 1 provides a schematic illustration of a machine learning architecture comprising an artificial neural network with one hidden layer.

High-resolution imaging of cells or sub-cellular structures can provide a wealth of phenotypic data (e.g., data for size, shape, structure, metabolic status (when coupled with, e.g., fluorescent indicators of ion concentration, membrane potential, etc.), and the spatial distribution of specific molecular components), and in some cases, genotypic data (e.g., when identifying genotypes using techniques such as fluorescence in situ hybridization (FISH)). However, the interpretation of imaging data and its use for characterizing subtle phenotypic differences between single cells (or sub-cellular structures) within a population of cells, between sub-populations of cells, or between two or more different populations of cells, is complex as well as difficult to correlate with the detailed molecular genetic data provided by modern sequencing techniques.

The systems and methods disclosed herein relate to the use of statistical and/or machine learning techniques to analyze images of cells or sub-cellular structures for the purpose of identifying a set of key cell attributes, e.g., phenotypic traits, that may be used, for example, to: (i) characterize individual cells, sub-populations of cells, or entire populations of cells, (ii) discriminate between cells or cell populations that exhibit subtle differences in their phenotypic traits, e.g., in response to a physical or chemical stimulus, a genetic mutation, an epigenetic modification, or an environmental change, and (iii) correlate cell phenotypic traits, or changes thereof, to biochemical, physiological, genetic, epigenetic, genomic, or other types of bioassay and nucleic acid sequencing data. The disclosed systems and methods utilize novel combinations of advanced microscopy and imaging techniques, image processing, and statistical and/or machine learning algorithms to enable the detection of and discrimination between subtle differences in such cellular traits (or features) as external shape, color, size, internal structure, texture, patterns of distribution of one or more specific biomolecules (e.g., proteins, glycosylated proteins, nucleic acid molecules, lipid molecules, glycosylated lipid molecules, carbohydrate molecules, metabolites, or ions), or any combination thereof, and to identify a basis set of key cellular attributes (i.e., a cell characterization data set) that may be used to characterize single cells, sub-populations of cells, or entire populations of cells. In some embodiments, the key cellular attributes identified through the statistical and/or machine learning approach may or may not correspond to observable phenotypic traits. In preferred embodiments, the cell characterization data set is of reduced dimensionality compared to that of the complete multi-dimensional feature set identified through image processing, and thereby facilitates the handling and comparison of image data with other types of experimental data, e.g., that obtained through bioassay or nucleic acid sequencing methods. Any of a variety of advanced microscopy and imaging techniques, image processing techniques, and statistical and/or machine learning techniques known to those of skill in the art may be used in practicing or implementing the disclosed methods and systems, as will be described in more detail below. In some preferred embodiments, the imaging technique may comprise super-resolution fluorescence microscopy, while the statistical and/or machine learning algorithm used to process the image data and identify a basis set of key cellular attributes may comprise the use of principal component analysis (PCA) or an artificial neural network (ANN), e.g., a convolutional neural network (CNN) or an autoencoder.

In some embodiments, the disclosed methods and systems further comprise the incorporation of nucleic acid sequencing data, protein sequencing data, and/or other types of bioassay data (e.g., biochemical data, physiological data, metabolic data, etc.) in addition to imaging data as part of a training data set used to train a machine learning algorithm of the disclosed methods. The nucleic acid sequencing data, protein sequencing data, and/or other types of bioassay data may then be used as input to the machine learning algorithm used to identify a basis set of key cellular attributes and to draw correlations between cell phenotypic traits and biochemical, physiological, metabolic, genetic, epigenetic, and/or genomic traits. In some embodiments, the disclosed methods and systems may be used to detect biochemical, physiological, metabolic, genetic, epigenetic, and/or genomic differences between cells based on subtle phenotypic differences exhibited in image data. In some embodiments, the disclosed methods and systems may be used to detect a biochemical, physiological, metabolic, genetic, epigenetic, and/or genomic response in cells that have been subjected to a physical stimulus, a chemical stimulus (e.g., exposure to a drug candidate), and/or environmental change. In some embodiments, the disclosed methods and systems may be used to identify a physical stimulus, a chemical stimulus (e.g., exposure to a drug candidate), and/or environmental change that results in a phenotypic response that matches a target reference response (e.g., a known phenotypic response in cells exposed to a known drug).

The disclosed systems and methods may have utility in a variety of biomedical research, drug discovery and development, and clinical diagnostic applications including, but not limited to, the study of intracellular signaling pathways, cell differentiation pathways, the identification of different cell types in heterogeneous tissues, drug candidate screening, cancer diagnosis, etc.

Definitions:

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts may be expressed as "about" a particular value or range. About also includes the exact amount. Hence "about 5 µL" means "about 5 µL" and also "5 µL." Generally, the term "about" includes an amount that would be expected to be within experimental error.

As used herein, the phrase "genetic trait" may refer to the presence of a specific allele or mutation (e.g., a point mutation, insertion, deletion, or frameshift mutation, and the like) in a set of one or more coding DNA sequences (e.g., the coding regions of genes that code for proteins) or non-coding DNA sequences (e.g., DNA sequences that are transcribed into transfer RNA molecules, ribosomal RNA molecules, regulatory RNA molecules, and the like).

As used herein, the phrase "genomic trait" may refer to the normal and/or abnormal activation and/or suppression of gene expression (e.g., for one gene or a plurality of genes) in wild type and/or abnormal (e.g., diseased) cells and tissues. In some cases, a genomic trait may be correlated with one or more genetic traits, and vice versa. In some cases, a genomic trait may comprise, for example, chromatin accessibility, i.e., the accessibility of the DNA to binding of agents such as transcription factors.

As used herein, the phrase "epigenetic trait" may refer to the presence of a specific set of one or more biochemical modifications that are correlated with heritable cellular or physiological phenotypic traits but which do not involve alterations in the genomic DNA nucleotide sequence. Examples include, but are not limited to, DNA methylation and histone modification. Such traits may, in some cases, give rise to altered patterns of gene activity and expression.

As used herein a latent trait (or latent variable) is a trait or variable that is not directly observable in a data set (e.g., an image), but is rather inferred using a mathematical model from other variables that are observed (directly measured). In some cases, a set of one, two, three or more latent variables may define a "latent space".

The section headings used herein are for organizational purposes only and are not to be construed as limiting the subject matter described.

Samples of Interest:

The disclosed methods and systems may be used to process and characterize images of any of a variety of samples. A sample as described herein may be a fresh sample or a fixed sample. The sample may be a fresh sample. The sample may be a fixed sample. The sample may be subjected to a denaturing condition. The sample may be cryopreserved. The sample may be stained with DAPI, Hoechst, SiR-DNA, and/or other fluorescent or bright-field stains.

The sample may be a cell sample. A cell sample may comprise a single cell or a plurality of cells. The cell sample comprising a plurality of cells (e.g., a population of cells or a sub-population of cells) may comprise at least 2 cells, at least 5 cells, at least 10 cells, at least $10^2$ cells, at least $10^3$ cells, at least $10^4$ cells, at least $10^5$ cells, at least $10^6$ cells, at least $10^7$ cells, at least $10^8$ cells, or at least $10^9$ cells.

The cell sample may be obtained from the cells of an animal. For example, the animal cell sample may comprise cells from a marine invertebrate, fish, insect, amphibian, reptile, or mammal. The mammalian cell sample may be obtained from a primate (e.g., human, ape), equine, bovine, porcine, canine, feline, or rodent sample. In some cases, the mammal may be a human, ape, dog, cat, rabbit, ferret, or the like. In some cases, the rodent may be a mouse, rat, hamster, gerbil, chinchilla, or guinea pig. In some cases, cells may be derived from a bird, e.g., a canary, parakeet, or parrot. In some cases, reptile cells may be from a turtle, lizard, or snake. In some cases, fish cells may be from a tropical fish. For example, the fish cells may be from a zebrafish (such as *Danio rerio*). In some cases, cells may be derived from a nematode (such as *Caenorhabditis elegans*). In some cases, amphibian cells may be derived from a frog or toad. In some cases, arthropod cells may be derived from, for example, a tarantula or hermit crab.

The cell sample may comprise cells obtained from a mammalian cell sample. For example, the mammalian cells may be epithelial cells, connective tissue cells, hormone secreting cells, nerve cells, skeletal muscle cells, blood cells, immune system cells, stem cells, or any combination thereof.

Cell samples may be cells derived from a cell line. Exemplary cell lines include, but are not limited to, 293A cell line, 293FT cell line, 293F cell line, 293 H cell line, HEK 293 cell line, CHO DG44 cell line, CHO-S cell line, CHO-K1 cell line, Expi293F™ cell line, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cell line, FreeStyle™ CHO-S cell line, GripTite™ 293 MSR cell line, GS-CHO cell line, HepaRG™ cell line, T-REx™ Jurkat cell line, Per.C6 cell line, T-REx™-293 cell line, T-REx™-CHO cell line, T-REx™-HeLa cell line, NC-HIMT cell line, and PC12 cell line.

As noted, the cell sample may be obtained from cells of a primate. The primate may be a human, or a non-human primate. The cell sample may be obtained from a human. For example, the cell sample may comprise cells obtained from blood, urine, stool, saliva, lymph fluid, cerebrospinal fluid, synovial fluid, cystic fluid, ascites, pleural effusion, amniotic fluid, chorionic villus sample, vaginal fluid, interstitial fluid, buccal swab sample, sputum, bronchial lavage, Pap smear sample, or ocular fluid. The cell sample may comprise cells obtained from a blood sample, an aspirate sample, or a smear sample.

The cell sample may be a circulating tumor cell sample. A circulating tumor cell sample may comprise lymphoma cells, fetal cells, apoptotic cells, epithelia cells, endothelial cells, stem cells, progenitor cells, mesenchymal cells, osteoblast cells, osteocytes, hematopoietic stem cells, foam cells, adipose cells, transcervical cells, circulating cardiocytes, circulating fibrocytes, circulating cancer stem cells, circulating myocytes, circulating cells from a kidney, circulating cells from a gastrointestinal tract, circulating cells from a lung, circulating cells from reproductive organs, circulating cells from a central nervous system, circulating hepatic cells, circulating cells from a spleen, circulating cells from a thymus, circulating cells from a thyroid, circulating cells from an endocrine gland, circulating cells from a parathyroid, circulating cells from a pituitary, circulating cells from an adrenal gland, circulating cells from islets of Langerhans, circulating cells from a pancreas, circulating cells from a hypothalamus, circulating cells from prostate tissues, circulating cells from breast tissues, circulating cells from circulating retinal cells, circulating ophthalmic cells, circulating auditory cells, circulating epidermal cells, circulating cells from the urinary tract, or combinations thereof.

A cell sample may be a peripheral blood mononuclear cell sample.

A cell sample may comprise cancerous cells. The cancerous cells may form a cancer which may be a solid tumor or a hematologic malignancy. The cancerous cell sample may comprise cells obtained from a solid tumor. The solid tumor may include a sarcoma or a carcinoma. Exemplary sarcoma cell sample may include, but are not limited to, cell sample obtained from alveolar rhabdomyosarcoma, alveolar soft part sarcoma, ameloblastoma, angio sarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyo sarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, or telangiectatic osteosarcoma.

Exemplary carcinoma cell samples may include, but are not limited to, cell samples obtained from an anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

The cancerous cell sample may comprise cells obtained from a hematologic malignancy. Hematologic malignancy may comprise a leukemia, a lymphoma, a myeloma, a non-Hodgkin's lymphoma, or a Hodgkin's lymphoma. The hematologic malignancy may be a T-cell based hematologic malignancy. The hematologic malignancy may be a B-cell based hematologic malignancy. Exemplary B-cell based hematologic malignancy may include, but are not limited to, chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. Exemplary T-cell based hematologic malignancy may include, but are not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

A cell sample described herein may comprise a tumor cell line sample. Exemplary tumor cell line sample may include, but are not limited to, cell samples from tumor cell lines such as 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

A cell sample may comprise cells obtained from a biopsy sample.

The cell samples (such as a biopsy sample) may be obtained from an individual by any suitable means of obtaining the sample using well-known and routine clinical methods. Procedures for obtaining tissue samples from an individual are well known. For example, procedures for drawing and processing tissue sample such as from a needle aspiration biopsy are well-known and may be employed to obtain a sample for use in the methods provided. Typically, for collection of such a tissue sample, a thin hollow needle is inserted into a mass such as a tumor mass for sampling of cells that, after being stained, will be examined under a microscope.

Optical Imaging Techniques:

Any of a variety of advanced microscopy and imaging techniques known to those of skill in the art may be used to implement the disclosed methods. Examples include, but are not limited to, bright-field microscopy, dark-field microscopy, phase contrast microscopy, differential interference contrast microscopy (DIC), and the like, where the combination of magnification and contrast mechanism provides images having cellular or sub-cellular image resolution.

In some embodiments, one or more far-field or near-field fluorescence techniques may be utilized for detecting one or more cells described herein. In some cases, the microscopy method chosen for image acquisition may be a high magnification oil immersion microscopy method. In such cases, wide-field and/or confocal fluorescent microscopes may enable imaging with sub-cellular resolution.

Super-Resolution Imaging:

In some preferred embodiments, super-resolution light microscopy techniques which allow images to be captured with a higher resolution (e.g., approximately 10-200 nm resolution) than that determined by the diffraction limit of light may be utilized. In some cases, the super-resolution microscopy method may comprise a deterministic super-resolution microscopy method, which utilizes a fluorophore's nonlinear response to excitation to enhance image resolution. Exemplary deterministic super-resolution methods include stimulated emission depletion (STED), ground state depletion (GSD), reversible saturable optical linear fluorescence transitions (RESOLFT), structured illumination microscopy (SIM), and/or saturated structured illumination microscopy (SSIM). In some cases, the super-resolution microscopy method may comprise a stochastic super-resolution microscopy method, which utilizes a complex temporal behavior of a fluorescence signal, to enhance resolution. Exemplary stochastic super-resolution method include super-resolution optical fluctuation imaging (SOFI), all single-molecule localization methods (SMLM) such as spectral precision distance microscopy (SPDM), spectral precision distance microscopy using physically-modifiable fluorophores (SPDMphymod), photo-activated localization microscopy (PALM), fluorescence photo-activated localization microscopy (FPALM), stochastic optical reconstruction microscopy (STORM), and direct stochastical optical reconstruction microscopy (dSTORM). A more detailed description of suitable super-resolution optical microscopy methods for use in the disclosed methods and systems may be found in, for example, G. Patterson, et al., (2010), "Superresolution Imaging using Single-Molecule Localization", Annu Rev Phys Chem. 61: 345-367, and J. Vangindertael, et al. (2018), "An Introduction to Optical Super-Resolution Microscopy for the Adventurous Biologist", Methods Appl. Fluoresc. 6:022003.

In some embodiments, the microscopy method utilized may comprise a single-molecule localization method (SMLM) based on, for example, the use of nonlinear optical approaches to reduce the focal spot size of a laser used for illumination (i.e., illumination-based super-resolution), or the controlled activation and sampling of sparse subsets of photoconvertible fluorescent molecules (i.e., probe-based super-resolution). One non-limiting example of a single molecule localization method is a spectral precision distance microscopy (SPDM) which relies on, for example, stochastic bursts or blinking of fluorophores and subsequent temporal integration and computer processing of signals to achieve lateral resolution at, for example, between about 10 nm and about 100 nm.

In some embodiments, the microscopy method may comprise a spatially modulated illumination (SMI) method. An SMI method may, for example, utilize phased lasers and interference patterns to illuminate specimens and increase resolution by measuring the signal in the fringes of the resulting Moire patterns.

In some embodiments, the microscopy method may comprise a synthetic aperture optics (SAO) method. A SAO method may utilize a low magnification, low numerical aperture (NA) lens to achieve large field of view and depth of field, without sacrificing spatial resolution. For example, an SAO method may comprise illuminating the detection agent-labeled target (such as a target nucleic acid sequence) with a predetermined number (N) of selective excitation patterns, where the number (N) of selective excitation patterns is determined based upon the detection agent's physical characteristics corresponding to spatial frequency content (such as the size, shape, and/or spacing of the detection agents on the imaging target). The illuminated target is optically imaged at a resolution insufficient to resolve the detection agents (or objects) attached to the target, and the resultant images are processed using information on the selective excitation patterns to obtain a final image of the target at a resolution sufficient to resolve the detection agents (or objects). The number (N) of selective excitation patterns may correspond to the number of k-space sampling points in a k-space sampling space in a frequency domain, with the extent of the k-space sampling space being substantially proportional to an inverse of a minimum distance ($\Delta x$) between the objects that are to be resolved by SAO, and with the inverse of the k-space sampling interval between the k-space sampling points being less than a width (w) of a detected area captured by a pixel of a system for said optical imaging. The number (N) may be dependent on various parameters of the imaging system (such as the magnification of the objective lens, numerical aperture of the objective lens, wavelength of the light emitted from the imaging target, and/or effective pixel size of the pixel sensitive area of the image detector, etc.).

In some embodiments, an SAO method may be utilized to analyze sets of detection agent profiles from at least 100, at least 200, at least 250, at least 500, at least 1000, at least 10,000, or more cells imaged simultaneously within one field of view utilizing an imaging instrument. In some embodiments, the one field of view may be a single wide field of view allowing image capture of at least 100, at least 200, at least 250, at least 500, at least 1000, at least 10,000, or more cells.

The single wide field of view may be about 0.70 mm by about 0.70 mm field of view. The SAO imaging instrument may enable a resolution of about 0.25 µm with a 20×/0.45 NA lens. The SAO imaging instrument may enable a depth of field of about 2.72 µm with a 20×/0.45 NA lens. The imaging instrument may enable a working distance of about 7 mm with a 20×/0.45 NA lens. The imaging instrument may enable a single cross-section in the z dimension with a 20×/0.45 NA lens. In some cases, the imaging instrument may provide for acquiring a z-stack of two-dimensional images, e.g., a series of two-dimensional images (each comprising a field-of-view of about 0.70 mm by about 0.70 mm), where each image is offset in the z direction from the previous image by an incremental step (z-step) ranging from about 100 nm to about 1 µm and covering a total thickness of about 5 µm to about 25 µm. In some cases, the SAO method may further integrate and interpolate 3-dimensional images based on a z-stack of 2-dimensional images.

In some embodiments of the disclosed methods and systems, the SAO imaging instrument may comprise an SAO instrument as described in U.S. Patent Publication No. 2011/0228073 (Lightspeed Genomics, Inc).

Non-Optical Imaging Techniques:

In some embodiments, the disclosed methods and systems may be implemented using non-optical imaging techniques. Examples include, but are not limited to, transmission electron microscopy images, scanning electron microscopy images, and the like.

Image Pre-Processing:

In some embodiments of the disclosed methods and systems, a series of one or more images, e.g., images acquired using an imaging system such as an SAO optical microscopy system, may be pre-processed to, for example, correct image contrast and brightness, correct for non-uniform illumination, correct for an optical aberration (e.g., a spherical aberration, a chromatic aberration, etc.), remove noise, identify objects (e.g., cells or sub-cellular structures) within each of the images, segment each of the images to isolate the identified objects, tile segmented images to create composite images, perform feature extraction (e.g., identification and/or quantitation of object properties such as observable cellular phenotypic traits), or any combination thereof. In some embodiments of the disclosed methods and systems, pre-processing may be performed using a combination of one or more image processing methods that are distinct from the statistical and/or machine learning methods used for subsequent feature selection and analysis of the multi-dimensional feature data set produced as output by a pre-processing software module. In some embodiments of the disclosed methods and systems, the pre-processing may be performed using a set of one or more processors (e.g., one or more processors configured as part of a pre-processing hardware module) that are distinct from the processors used to perform the statistical and/or machine learning methods used for subsequent feature selection and analysis. In some embodiments, image pre-processing may be integrated with or performed directly by the statistical and/or machine learning methods used for subsequent feature selection and analysis.

In addition to the identification of cells or sub-cellular structures in the series of one or more images to be processed, examples of features, e.g., cellular phenotypic traits, that may be identified and/or quantified through image pre-processing include, but are not limited to, external shape or morphology, size, surface texture, internal structure, patterns of distribution of one or more specific proteins, glycosylated proteins, nucleic acid molecules, lipid molecules, glycosylated lipid molecules, carbohydrate molecules, or metabolites (which, in some cases, may require labeling with a suitable detection label such as a fluorophore or fluorescently labeled antibody), ions (e.g., as visualized using an appropriate ion-sensitive fluorophore), or any combination thereof.

Any of a variety of image processing methods known to those of skill in the art may be used for image pre-processing to identify objects with the images. Examples include, but are not limited to, Canny edge detection methods, Canny-Deriche edge detection methods, first-order gradient edge detection methods (e.g., the Sobel operator), second order differential edge detection methods, phase congruency (phase coherence) edge detection methods, other image segmentation algorithms (e.g., intensity thresholding, intensity clustering methods, intensity histogram-based methods, etc.), feature and pattern recognition algorithms (e.g., the generalized Hough transform for detecting arbitrary shapes, the circular Hough transform, etc.), image texture analysis methods (e.g., gray-level co-occurrence matrices), and mathematical analysis algorithms (e.g., Fourier transform, fast Fourier transform, wavelet analysis, auto-correlation, etc.), or any combination thereof.

Statistical Analysis Methods:

In some embodiments of the disclosed methods and systems, a multi-dimensional feature data set produced as output from an image pre-processing method or module is further analyzed using a combination of one or more statistical analysis methods for the purpose of identifying the key components that underlie the observed variation in cell phenotype within a population of imaged cells. The combination of one or more statistical analysis methods may thus be used to generate a cell characterization data set comprising representations of one or more key attributes (e.g., cell or sub-cellular structure attributes) that provide a basis set of parameters for characterizing single cells, sub-populations of cells within a population, or entire populations of cells. In some embodiments, one or more of the key components (or attributes) that comprise the cell characterization data set may correspond directly to observable cell phenotypic traits such as those outlined above. In some embodiments, one or more of the key components (or attributes) that comprise the cell characterization data set may not correspond directly to observable cell phenotypic traits but rather may comprise some combination of observable cell phenotypic traits or may comprise latent features, i.e., features that are too subtle to be directly visible in the original images. In preferred embodiments, the cell characterization data set is of reduced dimensionality compared to the multi-dimensional feature data set produced as output from an image pre-processing module (i.e., it provides a compressed representation of the complete feature data set), thereby facilitating handling and comparison of image data to other types of experimental data, e.g., that obtained through bioassay or nucleic acid sequencing methods. In some embodiments, one or more statistical analysis methods may be used in combination with one or more of the machine learning methods described below.

In some embodiments, the basis set of key attributes identified by a statistical and/or machine learning-based analysis of the present disclosure may comprise 1 key attribute, 2 key attributes, 3 key attributes, 4 key attributes, 5 key attributes, 6 key attributes, 7 key attributes, 8 key attributes, 9 key attributes, 10 key attributes, 15 key attributes, 20 key attributes, or more.

Any of a variety of suitable statistical analysis methods known to those of skill in the art may be used in performing the disclosed methods. Examples include, but are not limited to, eigenvector-based analysis, regression analysis, probabilistic graphical models, or any combination thereof.

Eigenvector-based analysis is commonly used in physics and engineering and comprises the determination of a set of eigenvectors (also known as characteristic vectors, proper vectors, or latent vectors) that form an orthogonal basis set of unit vectors (each denoting an orthogonal axis of a multi-dimensional space) which, in combination with a corresponding set of eigenvalues (or scalar values) may be used to describe a multi-dimensional input data set (or input data vector). The determination of the eigenvectors and eigenvalues comprises application of a linear transformation (i.e., a transformation that preserves the mathematical operations of addition and scalar multiplication) to the input data, and is equivalent to the diagonalization of a matrix representing a linear system of equations.

Principal component analysis (PCA) is one example of eigenvector-based multivariate analysis. It is a statistical procedure that uses an orthogonal transformation to convert a set of input data (e.g., experimental measurements or observations that are dependent on a set of possibly correlated variables) into a set of values of linearly uncorrelated variables called principal components. The transformation is defined in such a way that the first principal component has the largest possible variance (i.e., accounts for as much of the variability in the input data set as possible), and each succeeding component in turn has the highest variance possible under the constraint that it is orthogonal to the preceding components. The resulting vectors provide an uncorrelated orthogonal basis set that define the dimensional axes in a multi-dimensional space. PCA can be thought of as a technique for revealing the internal structure of experimental data in a way that best explains the variance in the data, and may be used to provide a lower-dimensional representation of a multi-dimensional data set by using only the first few principal components so that the dimensionality of the transformed data is reduced.

Regression analysis refers to a set of statistical analysis and modeling processes for estimating the relationships among several variables or parameters, e.g., the relationship between a experimentally-measured value (i.e., a dependent variable) and one or more independent experimental parameters (or independent variables). The objective of regression analysis is often to determine how the value of the dependent variable changes when any one of the independent variables is varied while the other independent variables are held fixed. It is also used to generate a function of the independent variables called the regression- or fitting-function by adjusting a series of one or more adjustable parameters in the fitting function such that the value of an error function, comprising, e.g., the sum of the squares of the differences between the fitting function and the experimental data, is minimized. Regression analysis overlaps with the field of machine learning.

A variety of regression analysis methods have been developed, including parametric and nonparametric regression techniques. Linear regression and ordinary least squares regression are parametric, i.e., the regression function is defined in terms of a finite number of unknown parameters that are estimated from the data. Nonparametric regression refers to techniques that allow the regression function to reside within a specified set of functions. The performance of regression analysis methods generally depends on how well the function chosen to model the form of the data generating process (typically unknown) conforms to the actual process, i.e., on how good the assumptions made about the data generation process are. Regression methods sometimes refer specifically to the estimation of continuous response (dependent) variables, as opposed to the discrete response variables that are determined using classification methods.

The term "regularization", as used in the fields of statistical analysis and machine learning, refers to the process of introducing additional information in order to solve an ill-defined problem or to prevent overfitting. A regularization term, R(f), is added to a loss function (or cost function, e.g., a square loss function) that describes the estimated cost (or error) associated with, e.g., a given set of adjustable parameters in a fitting function in the case of regression analysis (or, e.g., the estimated error in a predicted output data set and a known test data set, in a machine learning context). A parameter, k, may be included to control the importance of the regularization term. R(f) is typically chosen to impose a penalty on the complexity of the model used to describe the data. Regularization can thus be used, for example, to reduce the number of adjustable parameters having non-zero values in regression functions, to bias machine learning algorithms towards learning simpler models, to induce regression and/or machine learning models to be sparse, etc.

A variety of different regularization methods may be used in conjunction with statistical and/or machine learning algorithms in implementing the disclosed methods and systems. Examples include, but are not limited to, L1 regularization, L2 regularization, etc. Lasso (least absolute shrinkage and selection operator) regression is an L1 regularization method that performs both variable selection and regularization in order to enhance the prediction accuracy and interpretability of the model it produces. Lasso regression adds a penalty term to the loss function that, in effect, shrinks the coefficients for less important features in the data set to zero, thus removing some features altogether. Lasso regression works well for feature selection in cases where there are a very large number of features in the data set. Ridge regression is an L2 regularization method that adds a different penalty term to the loss function. The key difference between L1 regularization and L2 regularization is the penalty term used in the loss function.

Probabilistic graphical models (PGMs) provide a framework for encoding probability distributions over complex domains, e.g., multivariate data sets distributed over large numbers of random variables that interact with each other.

These models or data representations rely on concepts derived from probability theory, graph algorithms, machine learning, etc., and provide the basis for a variety of state-of-the-art methods in medical diagnosis, image recognition, speech recognition, natural language processing, etc., and are also a foundational tool in formulating many machine learning problems. There are two basic PGM representations: Bayesian networks, which rely on a directed graph approach, and Markov networks, which use an undirected graph approach.

Machine Learning Methods:

In some embodiments of the disclosed methods and systems, a multi-dimensional feature data set produced as output from an image pre-processing method or module is further analyzed using a combination of one or more machine learning methods for the purpose of identifying the key components that underlie the observed variation in cell phenotype within a population of imaged cells. The combination of one or more machine learning methods may thus be used to generate a cell characterization data set comprising a representation of one or more key attributes (e.g., cell or sub-cellular structure attributes) that provide a basis set of parameters for characterizing single cells, sub-populations of cells within a population, or entire populations of cells. In some embodiments, one or more of the key components (or attributes) that comprise the cell characterization data set may correspond directly to observable cell phenotypic traits such as those outlined above. In some embodiments, one or more of the key components (or attributes) that comprise the cell characterization data set may not correspond directly to observable cell phenotypic traits but rather may comprise some combination of observable cell phenotypic traits or may comprise latent features, i.e., features that are too subtle to be directly visible in the original images. In preferred embodiments, the cell characterization data set is of reduced dimensionality compared to the multi-dimensional feature data set produced as output from an image pre-processing module, thereby facilitating handling and comparison of image data to other types of experimental data, e.g., that obtained through bioassay or nucleic acid sequencing methods. In some embodiments, one or more machine learning methods may be used in combination with one or more statistical analysis methods, such as those described above. In some embodiments, the one or more machine learning algorithms utilized in implementing the disclosed methods and systems may be used to perform the pre-processing of images (e.g., segmentation and feature extraction) in addition to subsequently performing feature selection for the determination of a cell characterization data set comprising key attributes.

Any of a variety of machine learning algorithms may be used in implementing the disclosed image processing and analysis methods. For example, the machine learning algorithm employed may comprise a supervised learning algorithm, an unsupervised learning algorithm, a semi-supervised learning algorithm, a deep learning algorithm, or any combination thereof. In some embodiments, the machine learning algorithm employed may comprise an artificial neural network algorithm, a Gaussian process regression algorithm, a logistical model tree algorithm, a random forest algorithm, a fuzzy classifier algorithm, a decision tree algorithm, a hierarchical clustering algorithm, a k-means algorithm, a fuzzy clustering algorithm, a deep Boltzmann machine learning algorithm, a deep convolutional neural network algorithm, a deep recurrent neural network, or any combination thereof, some of which will be described in more detail below.

As noted above, the machine learning algorithm(s) employed in the disclosed methods and systems for characterizing cells or populations of cells may comprise a supervised learning algorithm, an unsupervised learning algorithm, a semi-supervised learning algorithm, a deep learning algorithm, etc., or any combination thereof.

Supervised learning algorithms: In the context of the present disclosure, supervised learning algorithms are algorithms that rely on the use of a set of labeled training data to infer the relationship between a set of one or more features for a given cell (or sub-cellular structure) and a classification of the cell or sub-cellular structure according to a specified set of classes, or to infer the relationship between a set of input cellular features and a set of user-specified cell (or sub-cellular structure) types. The training data comprises a set of paired training examples, e.g., where each example comprises a set of features detected for a given cell and the resultant classification of the given cell.

Unsupervised learning algorithms: In the context of the present disclosure, unsupervised learning algorithms are algorithms used to draw inferences from training datasets consisting of cell feature datasets that are not paired with labeled cell classification data. One example of a commonly used unsupervised learning algorithm is cluster analysis, which is often used for exploratory data analysis to find hidden patterns or groupings in multi-dimensional data sets. Other examples of unsupervised learning algorithms include, but are not limited to, artificial neural networks, association rule learning algorithms, hierarchical clustering algorithms, matrix factorization approaches, dimensionality reduction approaches, or any combination thereof.

Matrix factorization (or matrix decomposition) approaches are methods for reducing the complexity of a matrix for the purpose of discovering underlying latent factors or for predicting missing values of the matrix. A number of widely used machine learning methods, mainly clustering methods, can be accommodated into matrix factorization frameworks, e.g., non-negative matrix factorization or tensor decomposition frameworks. Non-negative matrix factorization (NNMF) comprises a group of algorithms used in in multivariate analysis, linear algebra, and machine learning where a matrix V is factorized into (usually) two matrices W and H, with the property that all three matrices have no negative elements. The non-negative constraint makes the resulting matrices easier to inspect and interpret.

Dimensionality reduction approaches are methods for reducing the number of random variables under consideration by identifying a set of principal variables. They are typically used for processes such as feature selection and feature extraction. Examples of dimensionality reduction approaches that may be incorporated into machine learning approaches include, but are not limited to, principal component analysis (PCA), multidimensional scaling (MDS), t-distributed stochastic neighbor embedding (t-SNE), and uniform manifold approximation and projection (UMAP). Principal component analysis (PCA) has been described above.

Multidimensional scaling (MDS) is a set of data analysis algorithms that may be used to visualize the structure of a set of objects (e.g., a plurality of cells) from data that approximate the distances between pairs of objects. The data set (comprising similarity data, dissimilarity data, distance data, or proximity data) must reflect the degree of similarity or dissimilarity between pairs of objects. Each object is represented by a point in a multidimensional space. The points are arranged in this space so that the distances between pairs of points have the strongest possible correlation to the degree of similarity between the pairs of objects. That is, two similar objects are represented by two points that are close together, and two dissimilar objects are represented by two points that are far apart. The space is usually a two- or three-dimensional Euclidean space, but may be non-Euclidean and may have more dimensions. There are a variety of different specific MDS algorithms that can be classified according to whether the similarity data are qualitative (called nonmetric MDS) or quantitative (metric MDS). The number of similarity matrices used and the nature of the MDS model can also be used to classify MDS approaches as, e.g., classical MDS matrix, unweighted model), replicated MDS (several matrices, unweighted model), and weighted MDS (several matrices, weighted model).

t-distributed stochastic neighbor embedding (t-SNE) is a machine learning algorithm for nonlinear dimensionality reduction that allows one to represent high-dimensional data in a low-dimensional space of two or three dimensions for better visualization. Specifically, it models each high-dimensional object by a two- or three-dimensional point in such a way that similar objects are modeled by nearby points and dissimilar objects are modeled by distant points with high probability.

Uniform manifold approximation and projection (UMAP) is another example of a machine learning technique for dimension reduction. UMAP is constructed from a theoretical framework based in Riemannian geometry and algebraic topology. The result is a practical scalable algorithm that applies to real world data. The UMAP algorithm is competitive with t-SNE for visualization quality, and in some cases, preserves more of the global data structure with superior run time performance. Furthermore, UMAP has no computational restrictions on embedding dimension, making it viable as a general purpose dimension reduction technique for machine learning.

Semi-supervised learning algorithms: In the context of the present disclosure, semi-supervised learning algorithms are algorithms that make use of both labeled and unlabeled cell (or sub-cellular structure) classification data for training (typically using a relatively small amount of labeled data with a larger amount of unlabeled data).

Deep learning algorithms: In the context of the present disclosure, deep learning algorithms are algorithms inspired by the structure and function of the human brain called artificial neural networks (ANNs), and specifically, are large neural networks comprising many layers of coupled "nodes" that may be used to map cell feature data to cell (or sub-cellular structure) classification decisions. Artificial neural networks will be discussed in more detail below.

Decision tree-based expert systems: In the context of the present disclosure, expert systems are one example of supervised learning algorithms that may be designed to solve cell feature classification problems by applying a series of if—then rules. Expert systems typically comprise two subsystems: an inference engine and a knowledge base. The knowledge base comprises a set of facts (e.g., a training data set comprising cell feature data for a variety of cells or cell types, and the associated cell classification data provided by a skilled microscopist, pathologist, etc.) and derived rules (e.g., derived cell classification rules). The inference engine then applies the rules to data for a current cell classification problem to determine a classification of a cell or cell population.

Support vector machines (SVMs): In the context of the present disclosure, support vector machines are supervised learning algorithms that may be used for classification and regression analysis of cell feature classification data. Given a set of training data examples (e.g., cell feature data sets), each marked as belonging to one or the other of two categories (e.g., good or bad, pass or fail, normal or diseased), an SVM training algorithm builds a model that assigns new examples (e.g., feature data for a newly imaged cell or population of cells) to one category or the other.

Artificial neural networks (ANNs): In some cases, the machine learning algorithm used for the disclosed cell characterization methods and systems may comprise an artificial neural network (ANN), e.g., a deep machine learning algorithm. The cell characterization methods of the present disclosure may, for example, employ an artificial neural network to map cell feature data to cell classification decisions. The artificial neural network may comprise any type of neural network model, such as a feedforward neural network, radial basis function network, recurrent neural network, or convolutional neural network, and the like. In some embodiments, the disclosed methods and systems of the present disclosure may employ a pre-trained ANN architecture. In some embodiment, the disclosed methods and systems of the present disclosure may employ an ANN architecture wherein the training data set is continuously updated with real-time cell characterization data provided a single local cell characterization system, from a plurality of local cell characterization systems, or from a plurality of geographically distributed cell characterization systems.

As used throughout this disclosure, the term "real-time" refers to the rate at which experimental data or training data (e.g., cell feature data, cell classification data, constraints on cell population state, etc.) is acquired, processed, and/or used by a statistical and/or machine learning algorithm, e.g., an artificial neural network or deep machine learning algorithm, to update a cell classification decision or determination of a cell characterization data set. In general, the update rate for the cell characterization methods and systems of the present disclosure may range from about 0.1 Hz to about 1,000 Hz. In some embodiments, the update rate may be at least 0.1 Hz, at least 1 HZ, at least 10 Hz, at least 50 Hz, at least 100 Hz, at least 250 Hz, at least 500 Hz, at least 750 Hz, or at least 1,000 Hz. In some embodiments, the update rate may be at most 1,000 Hz, at most 750 Hz, at most 500 Hz, at most 250 Hz, at most 100 Hz, at most 50 Hz, at most 10 Hz, at most 1 Hz, or at most 0.1 Hz. Those of skill in the art will recognize that the update rate may have any value within this range, for example, about 200 Hz.

Figure 2:
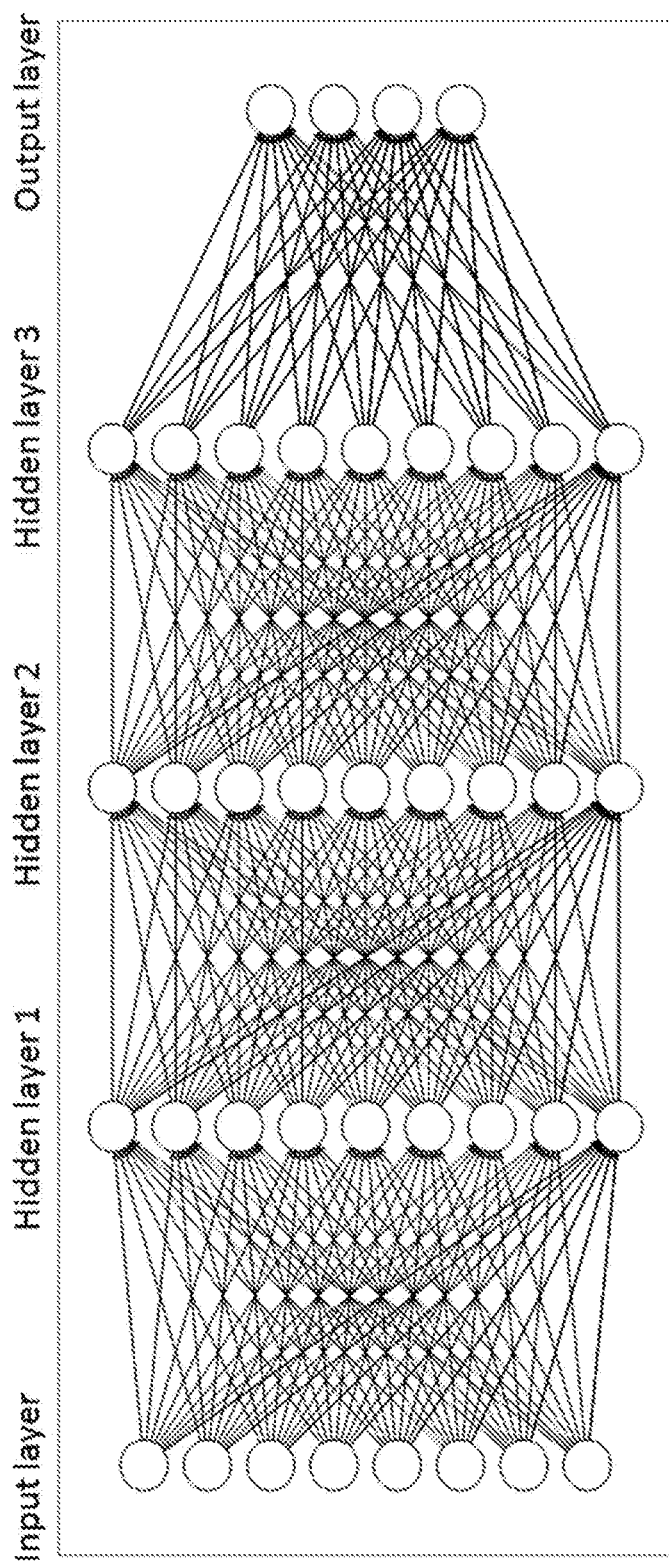
FIG. 2 provides a schematic illustration of a machine learning architecture comprising a deep learning algorithm, e.g., an artificial neural network comprising multiple hidden layers.
Figure 3:
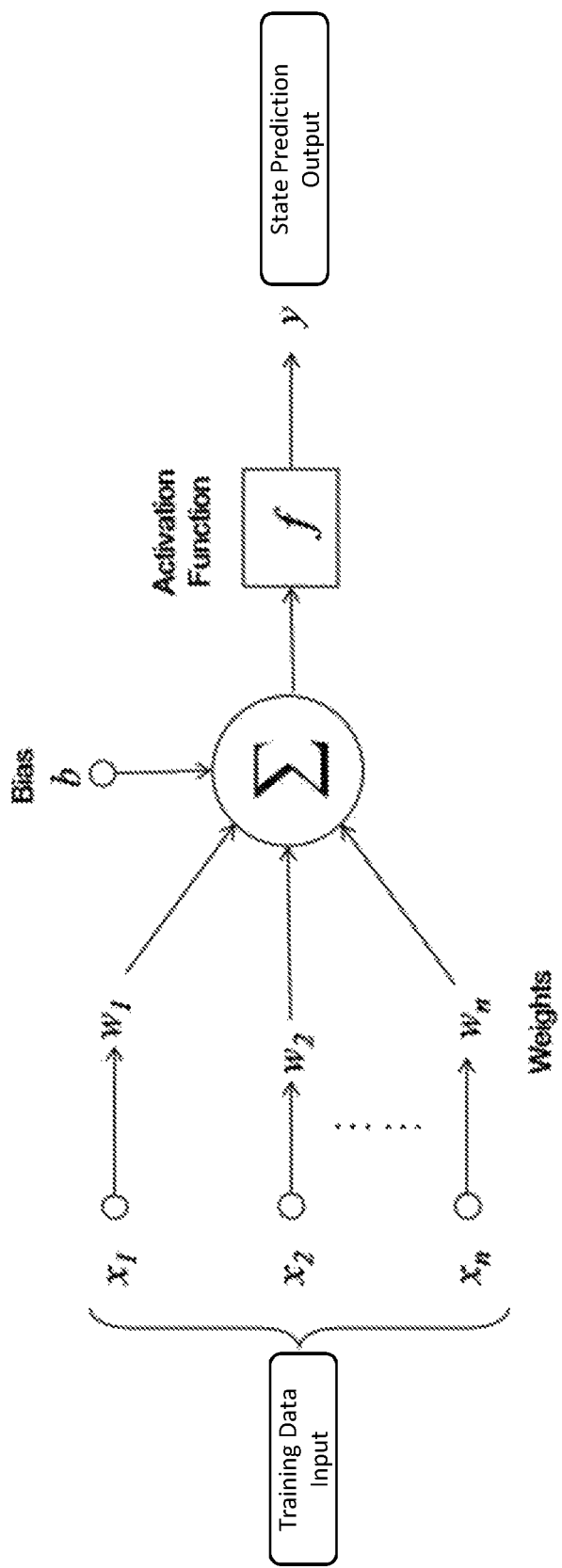
FIG. 3 provides a schematic illustration of a node within a layer of an artificial neural network or deep learning algorithm architecture.

Artificial neural networks generally comprise an interconnected group of nodes organized into multiple layers of nodes. For example, the ANN architecture may comprise at least an input layer, one or more hidden layers, and an output layer (FIG. 1 and FIG. 2). The ANN may comprise any total number of layers, and any number of hidden layers, where the hidden layers function as trainable feature extractors that allow mapping of a set of input data to a preferred output value or set of output values. Each layer of the neural network comprises a number of nodes (or neurons). A node receives input that comes either directly from the input data (e.g., cell feature data derived from image data, or other types of input data as will be discussed below, in the case of the presently disclosed methods) or the output of nodes in previous layers, and performs a specific operation, e.g., a summation operation. In some cases, a connection from an input to a node is associated with a weight (or weighting factor). In some cases, the node may, for example, sum up the products of all pairs of inputs, $x_i$, and their associated weights, $w_i$ (FIG. 3). In some cases, the weighted sum is offset with a bias, b, as illustrated in FIG. 3. In some cases, the output of a neuron may be gated using a threshold or activation function, f, which may be a linear or non-linear function. The activation function may be, for example, a rectified linear unit (ReLU) activation function or other function such as a saturating hyperbolic tangent, identity, binary step, logistic, arcTan, softsign, parameteric rectified linear unit, exponential linear unit, softPlus, bent identity, softExponential, Sinusoid, Sinc, Gaussian, or sigmoid function, or any combination thereof.

The weighting factors, bias values, and threshold values, or other computational parameters of the neural network, can be "taught" or "learned" in a training phase using one or more sets of training data. For example, the parameters may be trained using the input data from a training data set and a gradient descent or backward propagation method so that the output value(s) (e.g., a cell classification decision) that the ANN computes are consistent with the examples included in the training data set. The adjustable parameters of the model may be obtained from a back propagation neural network training process that may or may not be performed using the same hardware as that used for processing images and/or performing cell characterization.

Other specific types of deep machine learning algorithms, e.g., convolutional neural networks (CNNs) (often used for the processing of image data from machine vision systems) may also be used by the disclosed methods and systems. CNN are commonly composed of layers of different types: convolution, pooling, upscaling, and fully-connected node layers. In some cases, an activation function such as rectified linear unit may be used in some of the layers. In a CNN architecture, there can be one or more layers for each type of operation performed. A CNN architecture may comprise any number of layers in total, and any number of layers for the different types of operations performed. The simplest convolutional neural network architecture starts with an input layer followed by a sequence of convolutional layers and pooling layers, and ends with fully-connected layers. Each convolution layer may comprise a plurality of parameters used for performing the convolution operations. Each convolution layer may also comprise one or more filters, which in turn may comprise one or more weighting factors or other adjustable parameters. In some instances, the parameters may include biases (i.e., parameters that permit the activation function to be shifted). In some cases, the convolutional layers are followed by a layer of ReLU activation function. Other activation functions can also be used, for example the saturating hyperbolic tangent, identity, binary step, logistic, arcTan, softsign, parameteric rectified linear unit, exponential linear unit, softPlus, bent identity, softExponential, Sinusoid, Sinc, Gaussian, the sigmoid function and various others. The convolutional, pooling and ReLU layers may function as learnable features extractors, while the fully connected layers may function as a machine learning classifier. As with other artificial neural networks, the convolutional layers and fully-connected layers of CNN architectures typically include various adjustable computational parameters, e.g., weights, bias values, and threshold values, that are trained in a training phase as described above.

Figure 4:
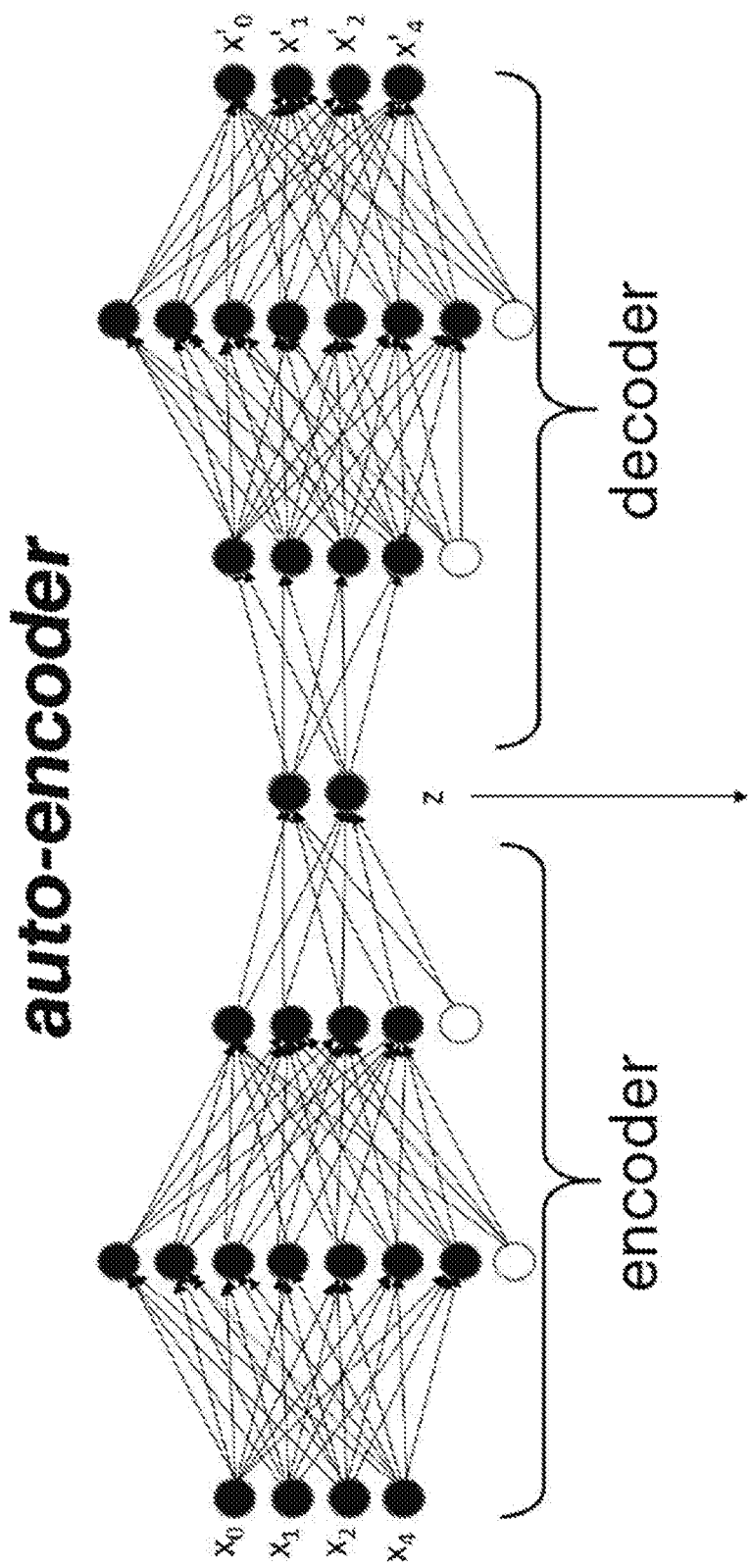
FIG. 4 illustrates the structure of an autoencoder.

Autoencoders: In the context of the present disclosure, an autoencoder (also sometimes referred to as an autoassociator or Diabolo network) is an artificial neural network used for unsupervised, efficient mapping of input data, e.g., cell feature data, to an output value, e.g., a cell classification decision or determination of a cell characterization data set comprising representations of one or more key cellular attributes. FIG. 4 illustrates the basic architecture of an autoencoder, which will be described in more detail below. Autoencoders are often used for the purpose of dimensionality reduction, i.e., the process of reducing the number of random variables under consideration by deducing a set of principal component variables. Dimensionality reduction may be performed, for example, for the purpose of feature selection (e.g., selection of the most relevant subset of the cell features presented in the original, multi-dimensional cell feature data set) or feature extraction (e.g., transformation of cell feature data in the original, multi-dimensional space to a space of fewer dimensions).

Any of a variety of different autoencoder algorithms known to those of skill in the art may be used in the disclosed methods and systems. Examples include, but are not limited to, stacked autoencoders, denoising autoencoders, variational autoencoders, or any combination thereof. Stacked autoencoders are neural networks consisting of multiple layers of sparse autoencoders in which the output of each layer is wired to the input of the successive layer. Variational autoencoders (VAEs) are autoencoder models that use the basic autoencoder architecture, but that make strong assumptions regarding the distribution of latent variables. They use a variational approach for latent representation learning, which results in an additional loss component, and may require the use of a specific training algorithm called Stochastic Gradient Variational Bayes (SGVB).

Deep belief networks (DBN): In some embodiments, the disclosed methods and systems may utilize a deep belief network (DBN). A deep belief network is a generative graphical model (or class of deep neural network) composed of multiple layers of latent variables ("hidden nodes"), with connections between the layers but not between the nodes within each layer. When trained on a set of training data without supervision, a DBN can learn to probabilistically reconstruct its inputs. The layers then act as feature detectors. After this learning step, a DBN can be further trained with supervision to perform classification. DBNs can be viewed as a composition of simple, unsupervised networks, such as autoencoders, where each sub-network's hidden layer serves as the visible layer for the next.

Deep convolutional generative adversarial networks (DC-GANs): In some embodiments, the disclosed methods and systems may utilize a deep convolutional generative adversarial network (DCGAN). DCGANs are a class of convolutional neural networks (CNNs) used for unsupervised learning that further comprise a generative adversarial network (GANs), i.e., a class of algorithms implemented by a system of two neural networks contesting with each other in a zero-sum game framework. One network generates candidate images (or solutions) and the other network evaluates them. Typically, the generative network learns to map from a latent space to a particular data distribution of interest, while the discriminative network discriminates between instances from the true data distribution and the candidate images or solutions produced by the generator. The generative network's training objective is to increase the error rate of the discriminative network (i.e., "fool" the discriminator network) by producing novel synthesized instances that appear to have come from the true data distribution). In practice, a known dataset serves as the initial training data for the discriminator. Training the discriminator involves presenting it with samples from the dataset, until it reaches some level of accuracy. Typically the generator is seeded with a randomized input that is sampled from a predefined latent space (e.g. a multivariate normal distribution). Thereafter, samples synthesized by the generator are evaluated by the discriminator. Backpropagation is applied in both networks so that the generator produces better images, while the discriminator becomes more skilled at flagging synthetic images. The generator is typically a deconvolutional neural network, and the discriminator is a convolutional neural network.

Long short-term memory networks (LSTMs): LSTMs are an extension of Recurrent Neural Networks (RNNs) used to capture higher-order structures in sequential data, such as text or time-series data. A common LSTM unit (or node) is composed of a cell, an input gate, an output gate and a forget gate. The cell is responsible for "remembering" values over arbitrary time intervals. Each of the three gates can be thought of as a "conventional" node or artificial neuron, as used in a multi-layer (or feedforward) neural network, i.e., they compute an activation (using an activation function) of a weighted sum. They can be thought as regulators of the flow of numerical values that pass through the connections of the LSTM, hence the denotation "gate".

Regularization and sparsity constraints: In some machine learning approaches, e.g., those comprising the use of an ANN model, regularization and/or application of sparsity constraints may be utilized to improve the performance of the model. For example, regularization is often used in the field of classification. Empirical training of classification algorithms, based on "learning" using a finite data set, generally poses an underdetermined problem as the algorithm is attempting to infer a function f(x) of any given input value, x, based on a discrete set of example input values $x_1$, $x_2$, $x_3$, $x_4$, etc. In some cases, L1 regularization, L2 regularization, or other regularization schemes may be employed. In some cases, for example when using an autoencoder architecture, a sparsity constraint that limits the number of non-zero coefficients (or trainable parameters) in the model may be imposed on the hidden layers to limit the number of active hidden layers or nodes, and thereby enhance the ability of the autoencoder to discover interesting structure in the input data set even if the number of hidden layers is large. A node may be thought of as being "active" if its output value is close to 1, or as being "inactive" if its output value is close to 0 (assuming that a sigmoid activation function is used). Application of a sparsity constraint limits the nodes to being inactive most of the time, e.g., by setting the activation coefficient to be a function of the input value and dependent on a sparsity parameter typically having a small value close to zero (e.g., 0.05).

ANN architecture: In general, for any of the various types of ANN algorithms or models that may be used in the methods and systems disclosed herein, the number of nodes used in the input layer of the ANN (which enable input of data from, for example, sub-sampling of an image frame, a multi-dimensional cell feature data set, and/or other types of input data) may range from about 10 to about 10,000 nodes. In some instances, the number of nodes used in the input layer may be at least 10, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, or at least 10,000. In some instances, the number of node used in the input layer may be at most 10,000, at most 9000, at most 8000, at most 7000, at most 6000, at most 5000, at most 4000, at most 3000, at most 2000, at most 1000, at most 900, at most 800, at most 700, at most 600, at most 500, at most 400, at most 300, at most 200, at most 100, at most 50, or at most 10. Those of skill in the art will recognize that the number of nodes used in the input layer may have any value within this range, for example, about 512 nodes.

In some instances, the total number of layers used in the ANN (including input and output layers) may range from about 3 to about 20, or more. In some instances the total number of layers may be at least 3, at least 4, at least 5, at least 10, at least 15, or at least 20. In some instances, the total number of layers may be at most 20, at most 15, at most 10, at most 5, at most 4, or at most 3. Those of skill in the art will recognize that, in some cases, the total number of layers used in the ANN may have any value within this range, for example, 8 layers.

In some instances, the total number of learnable or trainable parameters, e.g., weighting factors, biases, or threshold values, used in the ANN may range from about 1 to about 10,000. In some instances, the total number of learnable parameters may be at least 1, at least 10, at least 100, at least 500, at least 1,000, at least 2,000, at least 3,000, at least 4,000, at least 5,000, at least 6,000, at least 7,000, at least 8,000, at least 9,000, or at least 10,000. Alternatively, the total number of learnable parameters may be any number less than 100, any number between 100 and 10,000, or a number greater than 10,000. In some instances, the total number of learnable parameters may be at most 10,000, at most 9,000, at most 8,000, at most 7,000, at most 6,000, at most 5,000, at most 4,000, at most 3,000, at most 2,000, at most 1,000, at most 500, at most 100 at most 10, or at most 1. Those of skill in the art will recognize that the total number of learnable parameters used may have any value within this range, for example, about 2,200 parameters.

Training data sets: As noted above, the type of training data used for training a machine learning algorithm for use in the disclosed methods and systems will depend on, for example, whether a supervised or unsupervised approach is taken. In some instances, one or more training data sets may be used to train the algorithm in a training phase that is distinct from that of the application or use phase. In some instances, the training data may be continuously updated and used to update the machine learning algorithm in real time. In some cases, the training data may be stored in a training database that resides on a local computer or server. In some cases, the training data may be stored in a training database that resides online or in the cloud.

In some instances, e.g., classification of cells or sub-cellular structures based on an analysis of multi-dimensional cell feature data sets, the training data may comprise data derived from a series of one or more pre-processed, segmented images where each image of the series comprises an image of an individual cell or a plurality of cells. In some instances, the machine learning algorithm may be used to perform all or a portion of the pre-processing and segmentation of the series of one or more images as well as the subsequent analysis (e.g., a classification decision, a determination of a cell characterization data set comprising representations of one or more key attributes of the cells, etc.). In some cases, the training data set may include other types of input data as well as images or data derived from images. For example, in some instances, the training data set may also comprise nucleic acid sequencing data, protein sequencing data, biochemical assay data, physiological data, genetic data, epigenetic data, genomic data, or other types of bioassay data. In these cases, nucleic acid sequencing data, protein sequencing data, biochemical assay data, physiological data, genetic data, epigenetic data, genomic data, or other types of bioassay data may subsequently be used as input to the trained machine learning algorithm, and may in some instances be used to identify correlations between specific cell features (e.g., specific cellular phenotypic traits) and nucleic acid sequence data, protein sequence data, biochemical data, physiological data, genetic data, epigenetic data, genomic data, and/or other types of bioassay data. In some instances, a machine learning algorithm trained, for example, using a combination of image-derived data and nucleic acid sequence data may subsequently be able to detect and identify changes in genetic or genomic traits based purely on the analysis of input cell image data.

In some instances, the training data set may comprise DNase I hypersensitivity assay data, i.e., data from any of a variety of assay techniques known to those of skill in the art that are used to map DNase I hypersensitive sites to specific positions in the genome. DNase I hypersensitive sites (DHSs) are regions of chromatin that are sensitive to cleavage by the DNase I enzyme. In these specific regions of the genome, chromatin has lost its condensed structure, exposing the DNA and making it accessible to degradation by enzymes such as DNase I. These accessible chromatin zones are functionally related to transcriptional activity, since this remodeled state is necessary for the binding of proteins such as transcription factors. DHSs have been used as markers of regulatory DNA regions that map many types of cis-regulatory elements including promoters, enhancers, insulators, silencers and locus control regions. In some cases, these markers may be identified using DNase-Seq.

In some instances, the training data set may comprise additional data, for example, data regarding the stage of a cell division cycle or development cycle at which cells were images, data regarding the normal or diseased state (e.g., a cancerous state, a pathogen-infected state, a viral-infected state, etc.) of the cells in the images, or data regarding other physical, chemical, or environmental constraints or stimuli to which the cells were subjected.

Machine learning software: Any of a variety of commercial or open-source software packages, software languages, or software platforms known to those of skill in the art may be used to implement the machine learning algorithms of the disclosed methods and systems. Examples include, but are not limited to, Shogun (www.shogun-toolbox.org), Mlpack (www.mlpack.rog), R (r-project.org), Weka (www.cs.waikato.ac.nz/ml/weka/), Python (www.python.org), and/or Matlab (MathWorks, Natick, MA, www.mathworks.com).

Cell Characterization Methods and Systems:

In some embodiments, the hardware components of the systems disclosed herein may comprise one or more processors utilized for pre-processing of a series of one or more images, and one or more processors utilized for performing statistical and/or machine learning-based analyses of the data derived from the images. In some embodiments, the processor(s) used to perform the image pre-processing and the statistical and/or machine learning-based analyses may be the same. In some embodiments, the processor(s) used to perform the image pre-processing and the statistical and/or machine learning-based analyses may be different. In some embodiments, the hardware components of the disclose systems may further comprise computer-readable media for storage of one or more software modules comprising the software code used to perform the disclosed methods, and for storage of training data, input image data, pre-processed image data, intermediate analysis data, output data, or any combination thereof. In some embodiments, the disclosed systems may further comprise an imaging system, for example, a super-resolution fluorescence microscope system. In some embodiments, the disclosed systems may further comprise one or more user interface devices such as keyboards, joysticks, mice, or displays, and/or one or more network interfaces such as Ethernet or USB connections for interfacing with other processors, computers, servers, intranets, the internet, or cloud-based databases.

Figure 5:
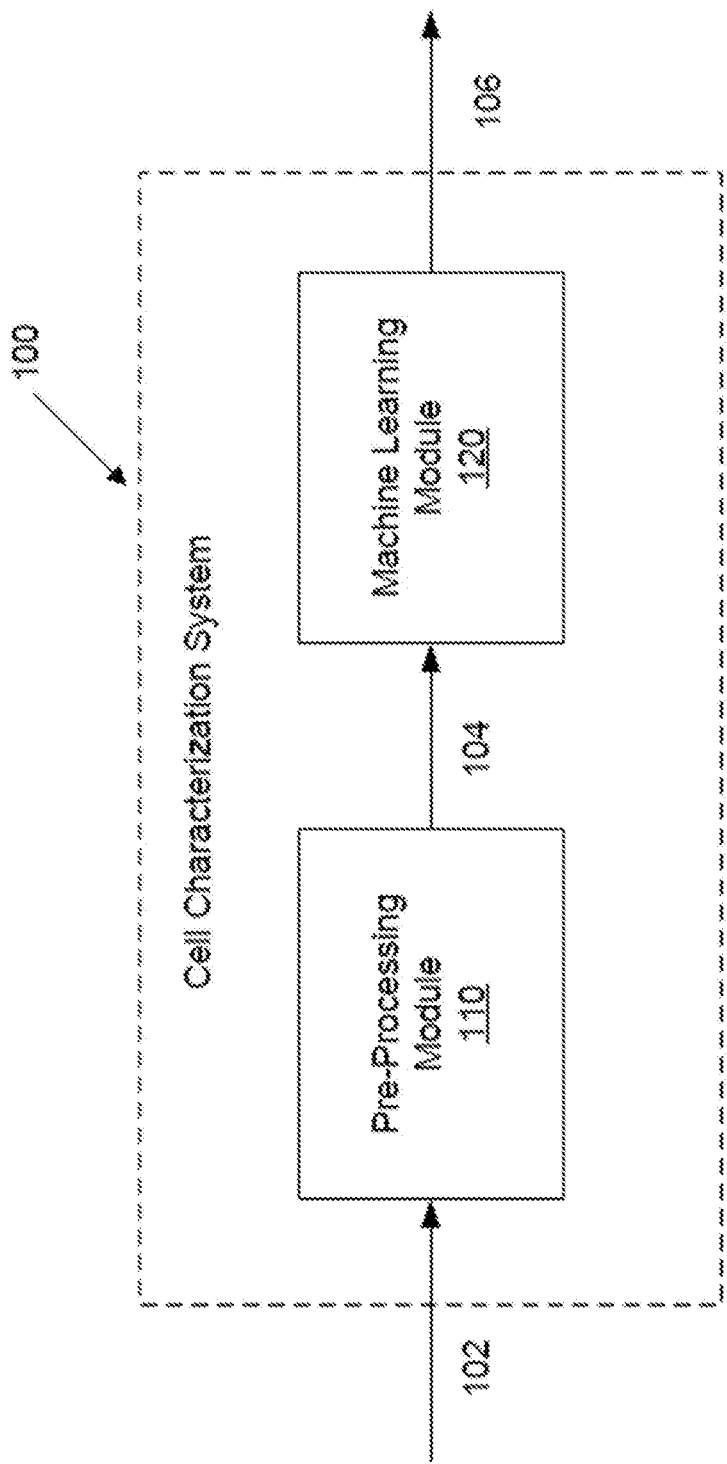
FIG. 5 shows a non-limiting example of a schematic block diagram of a cell characterization system comprising a pre-processing module and a machine learning module.

In some embodiments, the disclosed systems may comprise one or more software modules which further comprise the software code for performing the disclosed image processing and statistical and/or machine learning algorithms of the disclosed methods. In some embodiments, the machine learning algorithm used to perform classification and/or identification of key cellular attributes may also perform all or a portion of the image pre-processing and segmentation steps. In some embodiments, the disclosed systems may further comprise an imaging system, for example, a super-resolution fluorescence microscope system FIG. 5 illustrates a schematic block diagram of one non-limiting example of a cell characterization system comprising a pre-processing module and a machine learning module, in accordance with some embodiments. A cell characterization system 100 may comprise a pre-processing module 110 and a machine learning module 120 (also referred to as an analysis module, approximator, or an approximation module). The modules within the cell characterization system may be operatively connected to one another via a network or any type of communication link that allows transmission of data from one component to another. As noted above, the cell characterization system may be implemented using software, hardware, or a combination of software and hardware in a variety of different configurations.

In some embodiments, data comprising a series of one or more images of cells 102 may be collected using one or more optical or other microscopy techniques, as described elsewhere herein. The cell data 102 may comprise a series of one or more microscope images of single cells, a sub-population of cells, or an entire population of cells. The microscope images may be obtained using any of a variety of fluorescence or other microscopy techniques known to those of skill in the art. In some instances, the microscope images may be obtained using a wide-field fluorescence microscopy technique. In preferred embodiments, the microscope images may be obtained using a super-resolution microscopy technique.

In some embodiments, pre-processing module 110 may be configured to subject the single cell or cell population image data to one or more pre-processing techniques. For example, the pre-processing module may be used to remove imaging artifacts produced, for instance, by the microscopy technique used to acquire the images. In some instances, the pre-processing module may correct the microscope images for mechanical noise, such as drift of the microscope stage. In some instances, the pre-processing module may correct for uneven illumination of the microscope images, such as by applying image flat-field correction. In some instance, the pre-processing module may apply smoothing filters to reduce microscope image noise.

In some embodiments, the pre-processing module may be further configured to identify areas or regions of interest (ROI) within the microscope images. For instance, the pre-processing module may be configured to distinguish areas of interest within the microscope images in which an appreciable fluorescence signal is present from areas of non-interest within the images in which no appreciable fluorescence signal is present. The pre-processing module may be configured to detect the areas of interest by, for example, comparing the image intensity to a threshold on a pixel-by-pixel basis. Areas of interest may correspond to pixels in which the image intensity exceeds the threshold. Areas of interest may correspond to groups of, for instance, 2, 3, 4, 5, 6, 7, 8, 9, 10, or more than 10 adjacent pixels in which the image intensity exceeds the threshold. Discriminating areas of interest by groups of pixels may reduce the identification of "false positive" areas of interest, in which an area of interest is identified due to noise pushing the image intensity above the threshold for one or a few pixels.

In some cases, the pre-processing module may be configured to detect the areas of interest using a contour method. The pre-processing module may determine the image intensity, image intensity gradient, or both on a pixel-by-pixel basis and identify areas of interest based on the application of specified constraints to the image gradient. For instance, the pre-processing module may identify areas of interest as the collection of image pixels in which the image intensity, image intensity gradient, or both decrease monotonically as the distance from a central bright pixel or group of pixels increases. In some cases, the area of interest identified may be a single cell or nucleus. In some cases, a mask may be applied outside of the identified contour to eliminate signals from adjacent cells or nuclei.

The pre-processing module may be configured to output pre-processed cell population data 104 (e.g., cell feature data sets comprising data for one or more cell phenotypic traits) for single cells or a plurality of cells.

The pre-processing module may encode cell population data in a form of lower dimensionality as compared to that for the input series of images. For instance, fluorescence images of cells or cell populations may be informationally sparse, as only a small number of pixels may register a fluorescence signal in some cases. Additionally, optical images of cells or cell populations may display stereotypical behavior, owing to the known spatial variance of the optical signal in the vicinity of a cell. Both the sparsity of optical images of cell populations and their stereotypical behavior may make optical images of cell populations very compressible. In some instances, the pre-processing module may be viewed as enacting a form of compressed sensing on the cell population data, extracting a small set of features from each detected cell in the cell population, thereby reducing the amount of digital information required to describe cell population. In some embodiments, the pre-processing module may perform compression by a factor of greater than 10, greater than 100, or greater than 1,000. This high level of compression may significantly reduce the computational load on the machine learning module.

The machine learning module 120 may be configured to process the pre-processed cell population data 104 to extract a meaningful but simplified representation of the cell population data. For example, the machine learning module may be used to generate a set of cell characterization data 106 from the pre-processed cell population data, where the cell characterization data set comprises representations of one or more key attributes of individual cells or a plurality of cells within the population of cells. The cell characterization data set may correspond to a highly compressed, meaningful representation of the cell population data derived from a microscope image or series of microscope images.

The machine learning (or analysis) module 120 is used to extract a new representation of the cell population data (e.g., a cell characterization data set), where the new representation has characteristics such as low dimensionality, sparse coding, and/or invariance to certain noise sources or signal transformations. For example, the machine learning module 120 may map the image-derived input data to cell data representations that are insensitive (or less sensitive) to signal transformations that occur when the microscope moves relative to signal sources with the imaged sample, such as due to mild mechanical disturbance. In some instances, the machine learning module may determine representations of the cell population data that are corrected for changes in the properties of microscope images over time, for instance due to aging of components in the microscope, fluctuations in the intensity of the light delivered to the cell population by the light source, and other phenomena which alter the signal detected by the microscope over time. The key is that in each of the above cases, one or more statistical and/or machine learning-based transformations may be applied to the input cell population data, and depending on the representational scheme selected by the machine learning module, these transformations may or may not result in a change in the cell characterization data set that is output by the cell population characterization system. By training the machine learning algorithm to respond invariantly in the face of predictable and deterministic perturbations to the input data, these low-level changes may be rendered negligible compared to the high-level output of the cell characterization system.

In some embodiments, the high-level output of the cell characterization system may comprise, e.g., a cell classification decision. In some embodiments, the high-level output of the cell characterization system may comprise, e.g., the determination of a cell characterization data set comprising representations of one or more key attributes of single cells, sub-populations of cells, or entire populations of cells represented in the series of images used as input to the pre-processing module. As noted elsewhere, in some embodiments, the high-level output of the cell characterization system may comprise identification of correlations between phenotypic traits (e.g., comprising observable and/or latent phenotypic traits) and other cellular data, e.g., biochemical, physiological, metabolic, genetic, epigenetic, and/or genomic traits. In some embodiments, the high-level output of the cell characterization system may comprise detection and/or identification of biochemical, physiological, metabolic, genetic, epigenetic, and/or genomic traits, etc., based on the analysis of input cell image data.

In some embodiments, the above objective may be achieved by applying one or more machine learning methods that process their input data according to a learned (supervised) set of rules and map the input data to an output data set comprising, e.g., a cell classification decision or a cell characterization data set comprising representations of one or more key attributes of an input cell feature data set. In some embodiments, the above objectives may be achieved by applying one or more machine learning methods that process their input data according to a self-learned (unsupervised) set of rules. In some cases, the data set(s) used to train the one or more machine learning algorithms may include constraints relating to the underlying general cell population state space. Examples of such constraints include, but are not limited to, requiring that the cell population state should not change appreciably on the sub-second time scale, or that the cells of the cell population were in a specified stage of the cell division cell cycle at the time that they were imaged, as well as any other facts about the specific cell population state space as may be relevant for a given application.

As noted elsewhere, the machine learning module may also be implemented by explicitly modeling the input image data using probabilistic graphic models and/or using matrix methods such as L1/L2 lasso regularization (for finding sparse solutions) or eigenvector based approaches to find low rank approximations of the data matrix used for input. The machine learning module may also be implemented using neural networks such as autoencoders, stacked autoencoders, denoising autoencoders, deep belief networks, etc.

In some embodiments, the analysis module may be implemented as a multi-layered neural network where the output of each hidden layer of a plurality of hidden layers attempts to reconstruct the input from the preceding layer with some constraint imposed, or where its input has been either modified or transformed in a way to favor invariant representation. This may include so-called "deep belief networks" or "stacked auto-encoders". For example, the inner layers may be constrained by means of limiting what values their weights may take, or by limiting how quickly or tightly their weights may settle towards an optimal value as a form of a regularization strategy, etc. The multiple inner layers may lead to increasing degrees of abstraction and invariance to small perturbations of the signal. The layers may be updated separately, allowing for changes in cell population data over time to be learned by retraining of a low-level layer while the output of the higher level layers remain the same.

The training phase used to determine the parameters for the algorithm implemented at this stage may occur offline, but use of the analysis or machine learning module may be in real time. Updating of weights/coefficients may then occur regularly and while the analysis or machine learning module is in use.

Figure 6:
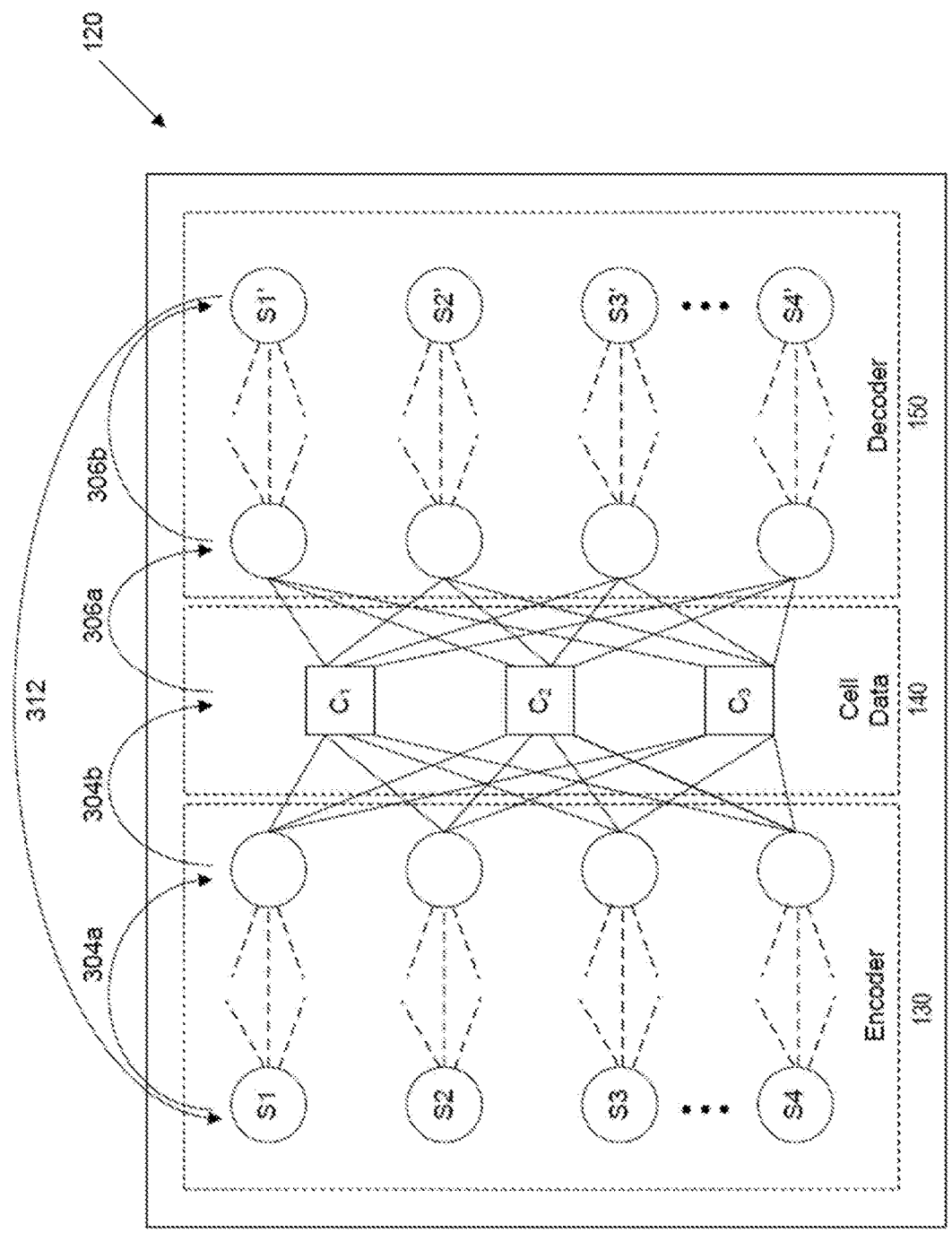
FIG. 6 shows an exemplary multi-layer autoencoder configured to convert a set of pre-processed cell population image data provided by the pre-processing module into minimal or basis set of cell population characterization parameters.

FIG. 6 illustrates an exemplary multi-layer autoencoder configured to convert a set of pre-processed cell population data from the pre-processing module into a cell characterization data set, in accordance with some embodiments. The machine learning module 120 may comprise an encoder 130 and a decoder 150. The machine learning module may be configured to output a cell characterization data set 140 comprising representations of one or more key attributes of single cells, sub-populations of cells, or the entire population of cells included in the input image data. The cell characterization data set may correspond to the a set of parameter values output by the inner-most layer of the autoencoder, and may or may not correspond to observable cellular phenotypic traits.

In some embodiments, the encoder may further comprise a plurality of encoding layers. Each encoding layer may comprise a plurality of nodes, each of which is associated with a numerical operator, an activation function, a bias, and/or a plurality of numerical weights (see FIG. 3) Similarly, the decoder may further comprise a plurality of decoding layers. Each decoding layer may comprise a plurality of nodes, each of which is also associated with a numerical operator, an activation function, a bias, and/or a plurality of numerical weights. The output of the innermost layer (or code layer) of the autoencoder may be the cell characterization data. The cell characterization data set may comprise a set of coefficients (e.g., adjusted parameter values) associated with a plurality of nodes. The cell characterization data set may comprise an abstract yet meaningful representation of cell population data within the machine learning architecture shown. In some embodiments, the machine learning module may comprise an autoencoder wherein the output of the decoder is a reconstruction of the input data set and is provided to the input to the encoder as part of an iterative training or analysis process. In some embodiments, the autoencoder may be a multi-layer autoencoder.

The encoder may be configured to receive an input comprising the set of pre-processed cell population data 104 from the pre-processing module. The set of pre-processed cell population data may be arranged as a vector S. The first layer of the encoder may be configured to reduce the dimensionality of the set of pre-processed cell population data by applying a transformation to the vector S. In some embodiments, the transformation may be a linear transformation. In other embodiments, the transformation may be a nonlinear transformation. The transformation may produce an output vector T having reduced dimensionality relative to the vector S, based on, for example, a function comprising a coefficient, a, a matrix W of weights at each node in the layer, and a transformation vector b:

$$T = a(WS + b) \tag{Equation 1}$$

The vector T may then be input to the second layer. Each successive encoding layer may apply matrix transformations of the same or similar form as Equation (1), with a successive reduction in dimensionality at each layer until the innermost layer (i.e., the code layer that represents the cell characterization data set) is reached.

The decoder may be configured to undo the abovementioned reduction in dimensionality in order to calculate the accuracy of the matrices of weights applied at each layer of the encoder. The cell characterization data set may be input to the first layer of the decoder, which may apply a linear transformation to increase dimensionality. Each successive decoding layer may apply further matrix transformations, until an output vector S' from the encoding layer that is of the same dimensionality as the original input data vector S is reached.

The initial weights of each node in each layer of the encoder, decoder, and code layer may be selected based on any predetermined procedure. The series of matrix transformations may be applied to map the input vector S at the first encoding layer to the output vector S' at the final decoding layer. An error function, such as an L1 error function or an L2 error function, may be calculated from S and S'. An algorithm, such as backpropagation-based training algorithm, may then be applied to update the weights at each node in each layer of the encoder, decoder, and code layer. The algorithm may be applied iteratively until the error function assessed at the output of the decoder reaches a minimum value or is less than a specified maximum error.

In some embodiments, sparsity constraints may be applied to some or all of the layers in the autoencoder model.

The machine learning module may be configured to distill a dataset having high dimensionality into a minimal set of numerical values that still represents the essential features of the input dataset while eliminating redundancy. This set of numerical values then forms the cell characterization data set corresponding to a given set of input cell population image data.

In some embodiments, the autoencoder can be designed in multiple layers in order to improve its robustness with regard to, for example, changes in the imaging performance of the microscope. This may also allow specific layers to be retrained in isolation to reduce the computational overhead of adapting the system to changing imaging conditions (e.g., physical changes to or variations in the microscope).

Accordingly, the cell characterization systems described herein may serve as a pipeline for processing cell population data comprising image information from single cells to thousands of cells. The system may be used to transform the multi-dimensional feature data set derived from image data to a higher-level representation of reduced dimensionality which represents salient features of the original image data.

Figure 7:
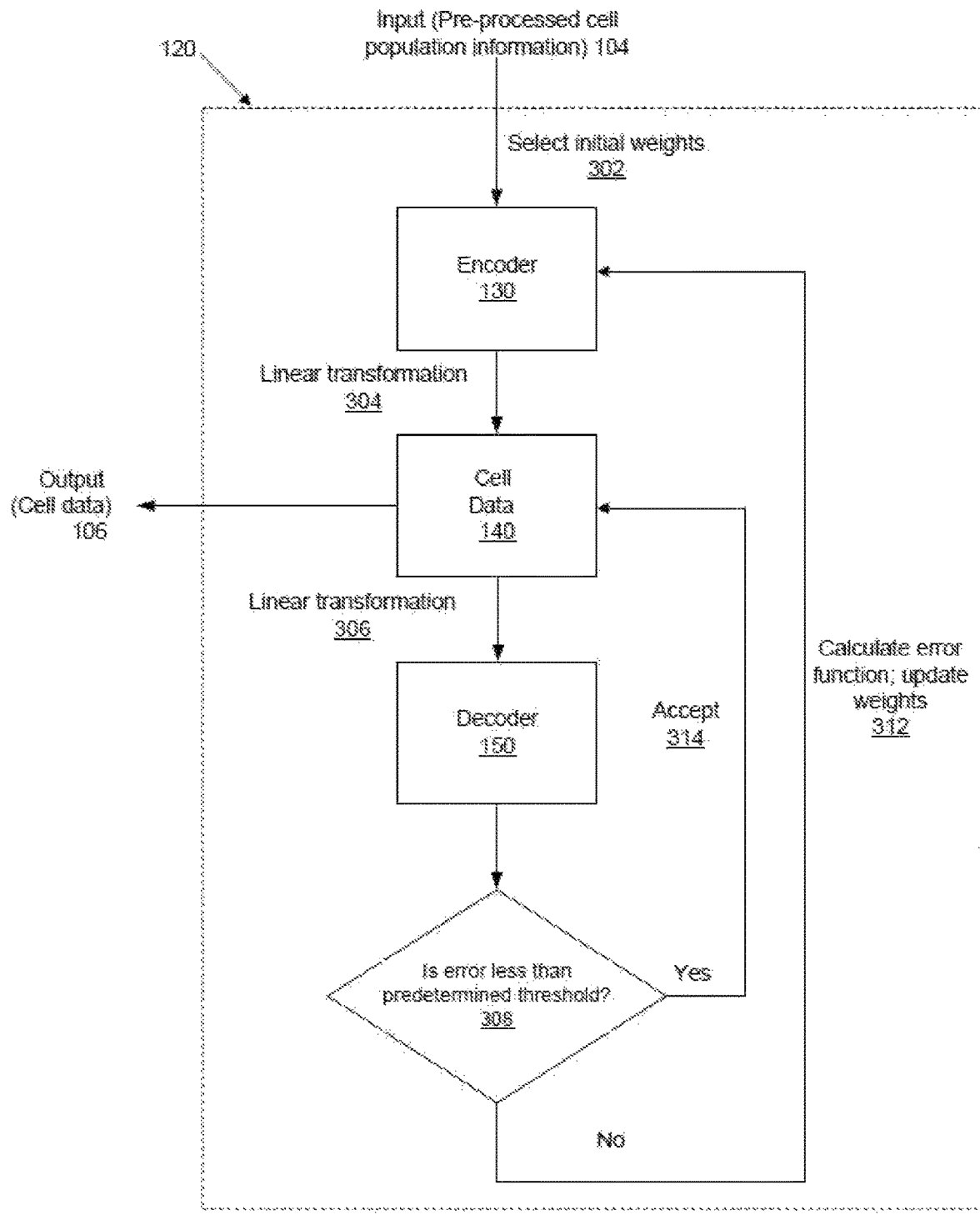
FIG. 7 shows a flowchart representing a process by which a minimal or basis set of cell population characterization parameters may be extracted from the input image data using an autoencoder algorithm comprising an encoder and a decoder.

FIG. 7 illustrates a flowchart representing a process by which cell characterization data may be extracted from the input to an autoencoder, in accordance with some embodiments of the present disclosure. The encoder 130 (of FIG. 6)

may accept as input a vector comprising a set of pre-processed cell population data 104 from the pre-processing module 110 (see FIG. 5). The initial weights 302 of each node in each layer of the encoder 130, code layer 140, and decoder 150 may be selected according to any preferred procedure. The encoder may apply a set of linear transformations 304, one linear transformation at each encoding layer, to calculate a first-pass cell characterization data set 106 which is output from the code layer 140. Each linear transformation at each layer of the encoder may reduce the dimensionality of the information passed to the next layer of the encoder.

The decoder may apply a further set of linear transformations 306, one linear transformation at each decoding layer. Each linear transformation at each layer of the decoder may increase the dimensionality of the information passed to the next layer of the decoder. The final layer of the decoder may produce a test code given by the weights of the nodes of the final layer of the decoder. The test code may be of the same dimensionality as the input data set provided to the encoder.

The values of the test code and the values of the input to the encoder may be compared through an error function in order to calculate an error. The error function may be the L1 error, given by the sum of absolute differences between the test code and the input to the encoder. The error function may be the L2 error or the Euclidean error, given by the sum of the squared differences between the test code and the input to the encoder. The error function may be an LN error, or a generalized Euclidean error of arbitrary dimensionality N. The error function may be any other error function known to those of skill in the art. In some instance, the error function used may be the same for each iteration. In some instances, the error function used may change between successive iterations.

In some instance, the error calculated from the test code and the input to the encoder may be compared to a specified condition. For example, the condition may be based on a predetermined threshold. If the error satisfies the condition, the instant value of the cell characterization data set may be accepted 314 and output 106 from the code layer. If the error fails to satisfy the specified condition, the weights of each node in each layer of the encoder 130, code layer 140, and decoder 150 may be updated 314 according to any preferred procedure. At this point, the procedure may proceed iteratively until the condition is satisfied. The condition may be defined such that that the error is smaller than a predetermined threshold value. The condition may also be defined such that the error is smaller than any of previously calculated errors. In some embodiments, the condition may remain the same for each iteration. In other embodiments, the condition may change between successive iterations. The procedure and iterations may be configured to end when the condition is met. In some embodiments, when the condition is met, the cell characterization data set from the current iteration will be output by the algorithm.

Although particular reference in this example is made to autoencoding methods, as noted above, other machine learning techniques, including various supervised machine learning techniques, various semi-supervised machine learning techniques, and/or various unsupervised machine learning techniques may be implemented in the in the machine learning module. For instance, the machine learning module may utilize alternating decision trees (ADTree), Decision Stumps, functional trees (FT), logistic model trees (LMT), logistic regression, Random Forests, linear classifiers, or any machine learning algorithm or statistical algorithm known in the art. One or more algorithms may be used together to generate an ensemble method, wherein the ensemble method may be optimized using a machine learning ensemble meta-algorithm such as a boosting (e.g., AdaBoost, LPBoost, TotalBoost, BrownBoost, MadaBoost, LogitBoost, etc.) to reduce bias and/or variance. Machine learning analyses may be performed using one or more of many programming languages and platforms known in the art, such as R, Weka, Python, and/or Matlab, for example.

Generative Modeling:

The machine learning systems and methods described herein may be utilized to perform data-driven cell biology experiments in silico through generative modeling techniques. The generative modeling techniques may comprise making one or more minor alterations to the cell characterization data set residing at the code layer 140 and propagating the changes through the layers of the decoder 150. The minor alterations may comprise varying one or more numerical entries of the cell characterization data set by, for example, a factor of less than 1%, less than 2%, less than 5%, less than 10%, less than 20%, or less than 50%. The output of the decoder may then be indicative of changes to the cell population data (e.g., cell features or phenotypes) that may be expected in response to small variations in the cell population. In this manner, generative modeling may be used to account for and predict systematic effects on cell phenotypic traits induced by a variety of experimental conditions and/or responses to physical stimuli, chemical stimuli, or environmental changes. This may allow for a comparison of cell populations subjected to different experiment conditions. In some instances, the generative modeling approach may serve as a quality control and benchmarking tool for detection of subtle systematic differences between experiments.

Digital Processing Device:

The systems, apparatus, and methods described herein may include a digital processing device, or use of the same. The digital processing device may include one or more hardware central processing units (CPU) that carry out the device's functions. The digital processing device may further comprise an operating system configured to perform executable instructions. In some instances, the digital processing device is optionally connected to a computer network, is optionally connected to the Internet such that it accesses the World Wide Web, or is optionally connected to a cloud computing infrastructure. In other instances, the digital processing device is optionally connected to an intranet. In other instances, the digital processing device is optionally connected to a data storage device.

In accordance with the description herein, suitable digital processing devices may include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers may include those with booklet, slate, and convertible configurations, known to those of skill in the art.

The digital processing device may include an operating system configured to perform executable instructions. The operating system may be, for example, software, including programs and data, which may manage the device's hardware and provides services for execution of applications. Those of skill in the art will recognize that suitable server operating systems may include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some cases, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some instances, the device may include a storage and/or memory device. The storage and/or memory device may be one or more physical apparatuses used to store data or programs on a temporary or permanent basis. In some instances, the device is volatile memory and requires power to maintain stored information. In other instances, the device is non-volatile memory and retains stored information when the digital processing device is not powered. In still other instances, the non-volatile memory comprises flash memory. The non-volatile memory may comprise dynamic random-access memory (DRAM). The non-volatile memory may comprise ferroelectric random access memory (FRAM). The non-volatile memory may comprise phase-change random access memory (PRAM). The device may be a storage device including, by way of non-limiting examples, CD-ROMs, DVDs, flash memory devices, magnetic disk drives, magnetic tapes drives, optical disk drives, and cloud computing based storage. The storage and/or memory device may also be a combination of devices such as those disclosed herein.

The digital processing device may include a display to send visual information to a user. The display may be a cathode ray tube (CRT). The display may be a liquid crystal display (LCD). Alternatively, the display may be a thin film transistor liquid crystal display (TFT-LCD). The display may further be an organic light emitting diode (OLED) display. In various cases, on OLED display is a passive-matrix OLED (PMOLED) or active-matrix OLED (AMOLED) display. The display may be a plasma display. The display may be a video projector. The display may be a combination of devices such as those disclosed herein.

The digital processing device may also include an input device to receive information from a user. For example, the input device may be a keyboard. The input device may be a pointing device including, by way of non-limiting examples, a mouse, trackball, track pad, joystick, game controller, or stylus. The input device may be a touch screen or a multi-touch screen. The input device may be a microphone to capture voice or other sound input. The input device may be a video camera or other sensor to capture motion or visual input. Alternatively, the input device may be a Kinect™, Leap Motion™, or the like. In further aspects, the input device may be a combination of devices such as those disclosed herein.

Non-Transitory Computer Readable Storage Medium:

In some instances, the systems, apparatus, and methods disclosed herein may include one or more non-transitory computer readable storage media encoded with a program including instructions executable by the operating system of an optionally networked digital processing device. In further instances, a computer readable storage medium is a tangible component of a digital processing device. In still further instances, a computer readable storage medium is optionally removable from a digital processing device. A computer readable storage medium may include, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Programs:

The systems, apparatus, and methods disclosed herein may include at least one computer program, or use of the same. A computer program includes a sequence of instructions, executable in the digital processing device's CPU, written to perform a specified task. In some embodiments, computer readable instructions are implemented as program modules, such as functions, objects, Application Programming Interfaces (APIs), data structures, and the like, that perform particular tasks or implement particular abstract data types. In light of the disclosure provided herein, those of skill in the art will recognize that a computer program, in certain embodiments, is written in various versions of various languages.

The functionality of the computer readable instructions may be combined or distributed as desired in various environments. A computer program may comprise one sequence of instructions. A computer program may comprise a plurality of sequences of instructions. In some instances, a computer program is provided from one location. In other instances, a computer program is provided from a plurality of locations. In additional cases, a computer program includes one or more software modules. Sometimes, a computer program may include, in part or in whole, one or more web applications, one or more mobile applications, one or more standalone applications, one or more web browser plug-ins, extensions, add-ins, or add-ons, or combinations thereof.

Web Applications:

A computer program may include a web application. In light of the disclosure provided herein, those of skill in the art will recognize that a web application, in various aspects, utilizes one or more software frameworks and one or more database systems. In some cases, a web application is created upon a software framework such as Microsoft® .NET or Ruby on Rails (RoR). In some cases, a web application utilizes one or more database systems including, by way of non-limiting examples, relational, non-relational, object oriented, associative, and XML database systems. Sometimes, suitable relational database systems may include, by way of non-limiting examples, Microsoft® SQL Server, mySQL™ and Oracle®. Those of skill in the art will also recognize that a web application, in various instances, is written in one or more versions of one or more languages. A web application may be written in one or more markup languages, presentation definition languages, client-side scripting languages, server-side coding languages, database query languages, or combinations thereof. A web application may be written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). A web application may be written to some extent in a client-side scripting language such as Asynchronous Javascript and XML (AJAX), Flash® Actionscript, Javascript, or Silverlight®. A web application may be written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. Sometimes, a web application may be written to some extent in a database query language such as Structured Query Language (SQL). Other times, a web application may integrate enterprise server products such as IBM® Lotus Domino®. In some instances, a web application includes a media player element. In various further instances, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Applications:

A computer program may include a mobile application provided to a mobile digital processing device. In some cases, the mobile application is provided to a mobile digital processing device at the time it is manufactured. In other cases, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Applications:

A computer program may include a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. A computer program may include one or more executable complied applications.

Web Browser Plug-Ins:

The computer program may include a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB .NET, or combinations thereof.

Web browsers (also called Internet browsers) may be software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules:

The systems and methods disclosed herein may include software, server, and/or database modules, or use of the same. In view of the disclosure provided herein, software modules may be created by techniques known to those of skill in the art using machines, software, and languages known to the art. The software modules disclosed herein may be implemented in a multitude of ways. A software module may comprise a file, a section of code, a programming object, a programming structure, or combinations thereof. A software module may comprise a plurality of files, a plurality of sections of code, a plurality of programming objects, a plurality of programming structures, or combinations thereof. In various aspects, the one or more software modules comprise, by way of non-limiting examples, a web application, a mobile application, and a standalone application. In some instances, software modules are in one computer program or application. In other instances, software modules are in more than one computer program or application. In some cases, software modules are hosted on one machine. In other cases, software modules are hosted on more than one machine. Sometimes, software modules may be hosted on cloud computing platforms. Other times, software modules may be hosted on one or more machines in one location. In additional cases, software modules are hosted on one or more machines in more than one location.

Databases:

The methods, apparatus, and systems disclosed herein may include one or more databases, or use of the same. In view of the disclosure provided herein, those of skill in the art will recognize that many databases are suitable for storage and retrieval of analytical information described elsewhere herein. In various aspects described herein, suitable databases may include, by way of non-limiting examples, relational databases, non-relational databases, object oriented databases, object databases, entity-relationship model databases, associative databases, and XML databases. A database may be internet-based. A database may be web-based. A database may be cloud computing-based. Alternatively, a database may be based on one or more local computer storage devices.

Services:

The methods and systems described herein may further be performed as a service. For example, a service provider may obtain a sample that a customer wishes to analyze. The service provider may then process image data for the sample to be analyzed by any of the methods described herein, perform the analysis, and provide a report to the customer. In some instances, the customer may perform all or a portion of the image acquisition, pre-processing, or analysis and provide the results to the service provider. In some instances, the service provider then completes all or a portion of the image acquisition, pre-processing, or analysis and provides the results to the customer. In other instances, the customer may receive encoded analysis of the samples from the provider and decode the results using software installed locally (e.g., at the customer's location) or remotely (e.g., on a server reachable through a network). Sometimes, the software may generate a report and transmit the report to the customer. Exemplary customers include clinical laboratories, hospitals, industrial manufacturers and the like. Sometimes, a customer or party may be any suitable customer or party with a need or desire to use the methods provided herein.

Figure 8:
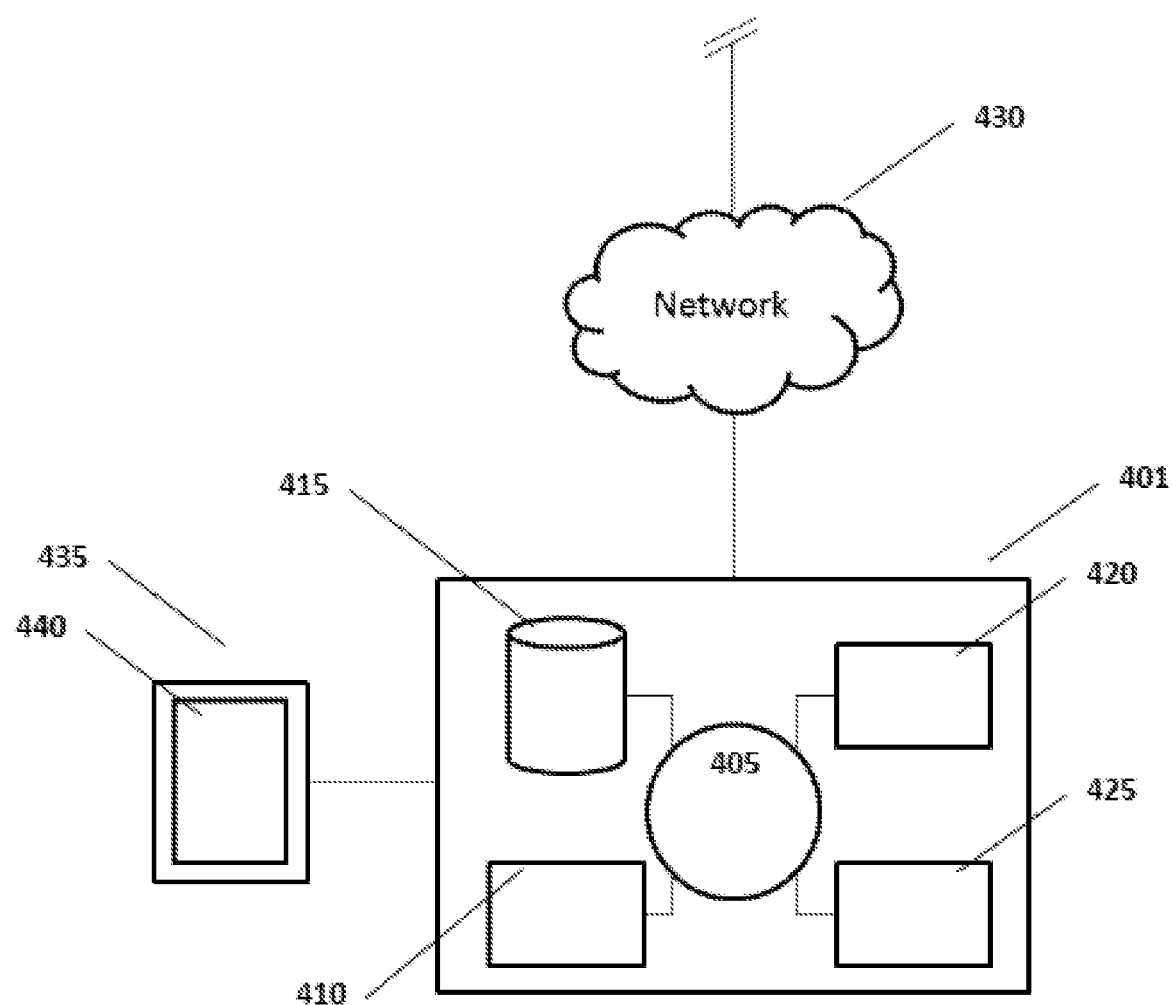
FIG. 8 shows a conceptual schematic of an exemplary computer system to be used for performing one or more of the image processing and cell characterization methods described herein.

Servers:

The methods provided herein may be processed on a server or a computer server, as shown in FIG. 8). The server 401 may include a central processing unit (CPU, also "processor") 405 which may be a single core processor, a multi core processor, or plurality of processors for parallel processing. A processor used as part of a control assembly may be a microprocessor. The server 401 may also include memory 410 (e.g. random access memory, read-only memory, flash memory); electronic storage unit 415 (e.g. hard disk);

communications interface 420 (e.g., network adaptor) for communicating with one or more other systems; and peripheral devices 425 which includes cache, other memory, data storage, and/or electronic display adaptors. The memory 410, storage unit 415, interface 420, and peripheral devices 425 may be in communication with the processor 405 through a communications bus (solid lines), such as a motherboard. The storage unit 415 may be a data storage unit for storing data. The server 401 may be operatively coupled to a computer network ("network") 430 with the aid of the communications interface 420. A processor with the aid of additional hardware may also be operatively coupled to a network. The network 430 may be the Internet, an intranet and/or an extranet, an intranet and/or extranet that is in communication with the Internet, a telecommunication or data network. The network 430 with the aid of the server 401, may implement a peer-to-peer network, which may enable devices coupled to the server 401 to behave as a client or a server. The server may be capable of transmitting and receiving computer-readable instructions (e.g., device/system operation protocols or parameters) or data (e.g., sensor measurements, raw data obtained from detecting metabolites, analysis of raw data obtained from detecting metabolites, interpretation of raw data obtained from detecting metabolites, etc.) via electronic signals transported through the network 430. Moreover, a network may be used, for example, to transmit or receive data across an international border.

The server 401 may be in communication with one or more output devices 435 such as a display or printer, and/or with one or more input devices 440 such as, for example, a keyboard, mouse, or joystick. The display may be a touch screen display, in which case it functions as both a display device and an input device. Different and/or additional input devices may be present such an enunciator, a speaker, or a microphone. The server may use any one of a variety of operating systems, such as for example, any one of several versions of Windows®, or of MacOS®, or of Unix®, or of Linux®.

The storage unit 415 may store files or data associated with the operation of a device, systems or methods described herein.

The server may communicate with one or more remote computer systems through the network 430. The one or more remote computer systems may include, for example, personal computers, laptops, tablets, telephones, Smart phones, or personal digital assistants.

A control assembly may include a single server 401. In other situations, the system may include multiple servers in communication with one another through an intranet, extranet and/or the Internet.

The server 401 may be adapted to store device operation parameters, protocols, methods described herein, and other information of potential relevance. Such information may be stored on the storage unit 415 or the server 401 and such data is transmitted through a network.

Applications:

The cell characterization methods and systems as described herein may be used to distinguish differences between single cells, sub-populations of cells, or large population of cells. In some cases, as the size of the population of cells being characterized increases, a lower resolution image may be used to provide segmented images and extracted feature data sets for the machine learning module. This may allow for the determination of a curve of detection using the machine learning approach, in which the number cells needed for analysis at a specific resolution may be determined empirically. Non-limiting examples of differences in cells that may be investigated may include chromatin structure, cell morphology, localization of small fragments of nucleic acids, proteins, lipids, and other biomolecules, or any combination thereof. These differences may comprise subtle patterns or differences that may not be assessed by the human eye. In some cases, for example, subtle patterns or differences in chromatin structure that may not be assessed by the human eye are determined by the methods described herein. Differences in chromatin structure between cells may be related to a difference in one or more genetic, epigenetic, or genomic traits between cells, which may be used to characterize single cells, sub-populations of cells, or large population of cells. Differences in chromatin structure between cells may be related to a difference in one or more observable phenotypic traits between cells, which may be used to characterize single cells, sub-populations of cells, or large population of cells. Thus, cells comprising a specific chromatin structure may be characterized as having one or more observable phenotypic, genetic, epigenetic, or genomic trait. In some cases, for example, Nano-FISH, which entails the detection of an oligonucleotide probe set labeled with a detectable moiety that hybridizes to the small fragments of nucleic acids may be used to investigate localization of small fragments of nucleic acids. Viral Nano-FISH, which entails the use of an oligonucleotide probe set labeled with a detectable moiety that hybridizes to viral vectors and vector payload, may be used to investigate localization of viral integrations into chromosomes. In some instances, the cells may be live cells or fixed cells. The cells may be human cells or non-human cells. The cell characterization system may be used to compare, for example, treated versus untreated cells. Treated cells may be cells treated with a drug or other chemical, may be cells infected by a pathogen or virus, may be cells that have undergone physical stress or temperature changes, may be cells that have undergone a genetic modification (e.g., a gene knockout), or may be cells that may have been grown in different conditions or environments. The cell characterization system may be used to compare diseased cells versus healthy cells, tumor cells versus non-tumor cells, or the same cell type from two different subjects. In some instances, the machine learning module may use a large scale databasing system to aid in the training of a machine learning algorithm and/or to facilitate image data processing. In some instance, the machine learning module may update a large scale databasing system using data obtained during cell characterization studies.

The disclosed systems and methods may have utility in a variety of biomedical research, drug discovery and development, and clinical diagnostic applications including, but not limited to, the study of intracellular signaling pathways, cell differentiation pathways, the identification of different cell types in heterogeneous tissues, drug candidate screening, cancer diagnosis, repurposing of existing regulatory elements or the design of new synthetic regulatory elements such as promoters (e.g., regions of DNA sequence that initiate transcription of a particular gene), enhancers (e.g., short regions of DNA sequence that are recognized and bound to by proteins (activators) to increase the likelihood that transcription of a particular gene will occur), insulators (e.g., DNA sequence boundary elements that block the interaction between enhancers and promoters), etc., through screening of environmental response levels for known-to-be tissue-specific regulatory elements, etc.

EXAMPLES

The following examples are included to further describe some aspects of the present disclosure, and should not be used to limit the scope of the present disclosure.

Example 1

Machine Learning Applied to Cells to Detect Different Chromatin Structure and/or Cellular Morphology This example demonstrates that, when applied to cells, machine learning is able to detect and correctly identify cells with different cellular morphologies and/or chromatin structures in a large population of cells. K265 cells are split into two different populations. One population is treated with an agent that changes chromatin structure and the other population is not treated. Each population is imaged, and a machine learning-based analysis is applied to the processed images. The populations are then mixed, and another image is taken. The machine learning-based analysis is then applied to the image data for the mixed population, and the cells that are derived from the treated versus untreated populations are identified on the basis of the detected changes in chomatin structure. The correct identification of the populations by the machine learning module is confirmed by performing the same experiment as described above, but with the additional step that the untreated and the treated cell populations are labeled with different fluorescent agents, e.g., fluorescently-labeled antibodies to the same cell surface receptor. When the populations are mixed, the different fluorescent agents for the treated cell population versus the untreated cell populations allows for confirmation that the machine learning module correctly distinguished between the two populations.

Example 2

Screening Drug Candidates to Identify Compounds that Affect Chromatin Structure

The primary role of the cell nucleus is to organize the genomic DNA that comprises the complete set of genetic instructions for replicating an organism, and to regulate the transcription of specific sets of genes and thus the set of proteins that are produced within different types of cells. Each cell comprises a complete genomic complement of DNA, yet different sets of genes are expressed in different types of cells as a result of regulatory mechanisms that control, for example, the accessibility of specific genes for transcription.

Chromatin is a macromolecular complex consisting of DNA, protein (e.g., histones), and RNA that is found in cell nuclei. In addition to packaging DNA into compact, dense structures, it plays a role in the regulation of gene expression. The overall structure depends on the stage of the cell cycle, for example, during interphase, the chromatin is structurally loose to allow access to RNA and DNA polymerases that transcribe and replicate the DNA. The local structure of chromatin depends on the genes present, such that DNA sequences that encode the genes that are actively transcribed (i.e., "turned on") in the cell are more loosely packaged and thus accessible to RNA polymerases, while DNA sequences that encode inactive genes (i.e., genes that are "turned off") is more condensed. Epigenetic chemical modification of the structural proteins in chromatin, e.g., chemical modifications of histone proteins by methylation and acetylation, can alter local chromatin structure. At other points in the cell cycle, e.g., mitosis or meiosis, the chromatin is packaged more tightly to facilitate segregation of the chromosomes during anaphase.

Because of its role in regulating gene expression in normal cells, chromatin presents a potential therapeutic target for treating disease, e.g., cancer (in which genes that are normally silent are accessible for transcription) and other genetic abnormalities. For example, drugs that target and modify chromatin structure, thereby causing it to pack more or less densely may provide tools for activating or silencing genes.

The disclosed methods and systems provide a means for screening drug candidates to identify compounds that intervene to alter chromatin structure, as detected and characterized by changes in one or more key attributes (e.g., one or more observable and/or latent phenotypic traits) and that would potentially provide tools for activating or silencing specific genes by altering their accessibility.

K265 cells or other suitable cell lines known to those of skill in the art are stained using a chromatin stain such as 4',6-diamidino-2-phenylindole (DAPI), a bis-benzimide Hoechst dye (e.g., Hoechst 33258, Hoechst 33342, or Hoechst 34580), SiR-DNA (SiR-Hoechst), or polychrome methylene blue-eosin Y (Giemsa stain) to visualize the chromatin structures within individual cell nuclei, and are imaged both before and after exposure to a drug candidate using a super-resolution fluorescence microscope. Variations in image intensity reflect variations in the density of the chromatin structure. Subsequent analysis using the disclosed cell characterization methods may identify a set of key phenotypic traits (observable and/or latent) that allow one to detect alterations in chromatin structure that have been induced by exposure to the drug candidate. Screening of compound libraries comprising hundreds to thousands of drug compounds select a subset of compounds to focus on for further development.

In some cases, the observed drug-induced alterations in chromatin structure may be correlated with the activation or silencing of specific genes by preparing genetically-engineered "knock-out" cell lines in which specific gene(s) have been mutated or deleted to disable the corresponding protein(s).

Example 3

Machine Learning for Phenotyping—Detection of Bromodomain Edits on Chromatin Structure Bromodomains are protein domains of approximately 110 amino acid residues that recognize and bind to acetylated lysine residues, such as those located on the N-terminal tail of histone proteins. Bromodomain-containing proteins play a role in transducing intracellular signals carried by acetylated lysine residues and translating them into various normal or abnormal phenotypes. This recognition event is often a prerequisite for triggering protein-histone association and chromatin structural reorganization. The bromodomain comprises an all-α protein fold, i.e., a bundle of four alpha helices each separated by loop regions of variable length that form a hydrophobic pocket that recognizes acetyl lysine.

Studies were conducted to evaluate the performance of a machine learning-based analysis of cell imaging data to detect changes in chromatin structure induced by editing specific genes the encode for proteins involved in bromodomain-mediated signaling. K562 cells were genetically-engineered to create 12 different bromodomain "knockouts" involving 10 genes. The cells were grown in 24 well plates. The cell nuclei for both wild-type and altered K562 cells were then stained with SiR-DNA stain (a far-red, fluorogenic, cell permeable, and highly specific probe for DNA), imaged using a high-resolution, high-throughput Stellar Vision fluorescence microscope, and processed to generate cell feature data sets that provided the input for a machine learning algorithm. 121 images were captured for each well of the 24 well plates, with each image comprising hundreds of cell nuclei per image.

Figure 9:
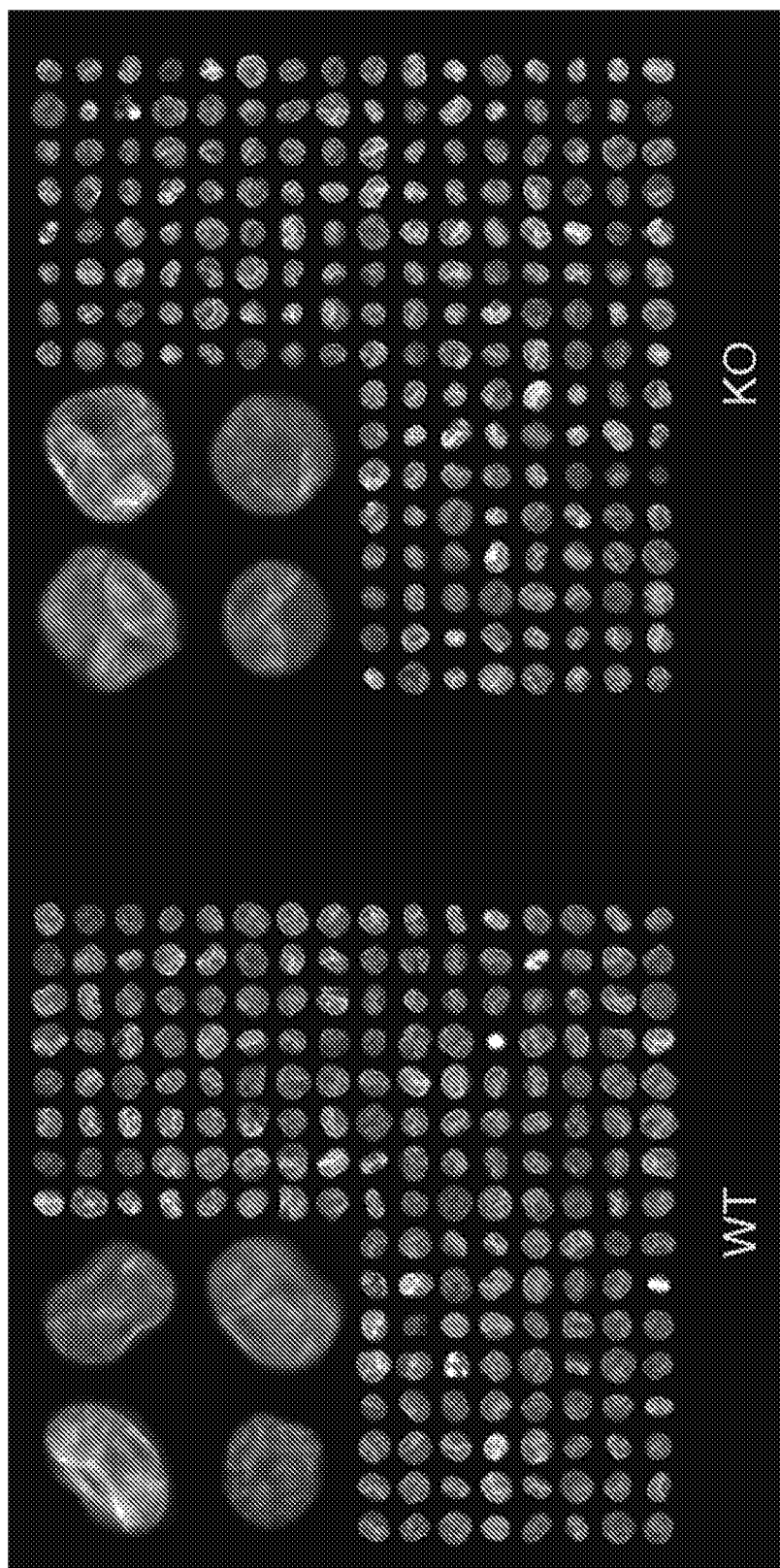
FIG. 9 provides non-limiting examples of two composite images comprised of images of single wild type (WT) or knock-out (KO) cell nuclei. The two inset figures illustrate magnified images of four representative cell nuclei within each of the larger populations represented in the composite images.

FIG. 9 provides examples of cell nuclei images that have been derived from the original images using image processing techniques to segment and tile the images. The images on the left are of wild-type (WT) cell nuclei. The images on the right are of the nuclei from a knock-out (KO) cell line. The insets for each show four magnified examples of individual cell nuclei. The objective of the study was to determine if a machine learning-based approach to image analysis can be used to detect subtle differences in phenotype (for single cells or for pools comprising a plurality of cells) that allow one to detect and discriminate between differences in the underlying chromatin structure as evidenced by subtle differences in phenotypic traits such as image intensity, intensity variation, image "texture", and the like. An additional objective was to test bromodomain inhibitors using the same machine learning-based approach.

Figure 10:
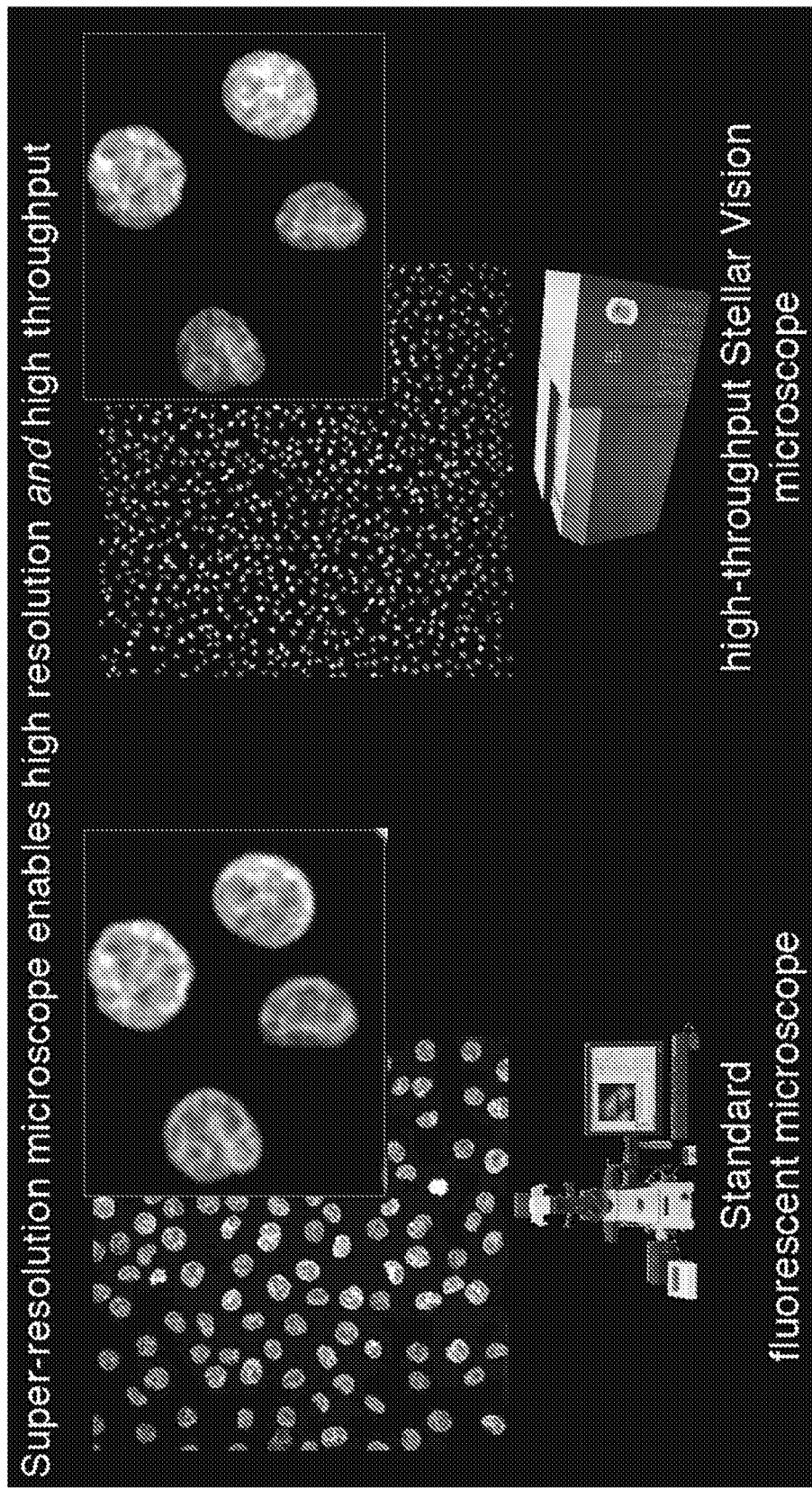
FIG. 10 provides a comparison of images of cell nuclei obtained using a conventional fluorescence microscope (left) versus those obtained using a super-resolution "Stellar Vision" fluorescence microscope (right). The two inset figures illustrate magnified images of four representative cell nuclei within each of the larger populations represented in the composite images.

FIG. 10 illustrates the difference between the images obtained using a standard fluorescence microscope (left) and those obtained using a high-resolution, high-throughput Stellar Vision microscope. The super-resolution optical design of the latter enables capture of wide field-of-view images comprising larger numbers of cells/nuclei while also preserving or exceeding the image resolution obtained at higher magnification using the standard fluorescence microscope. The insets provide a comparison of the image resolution obtained for images of the same set of four cells as captured by the two different microscope systems.

Figure 11:
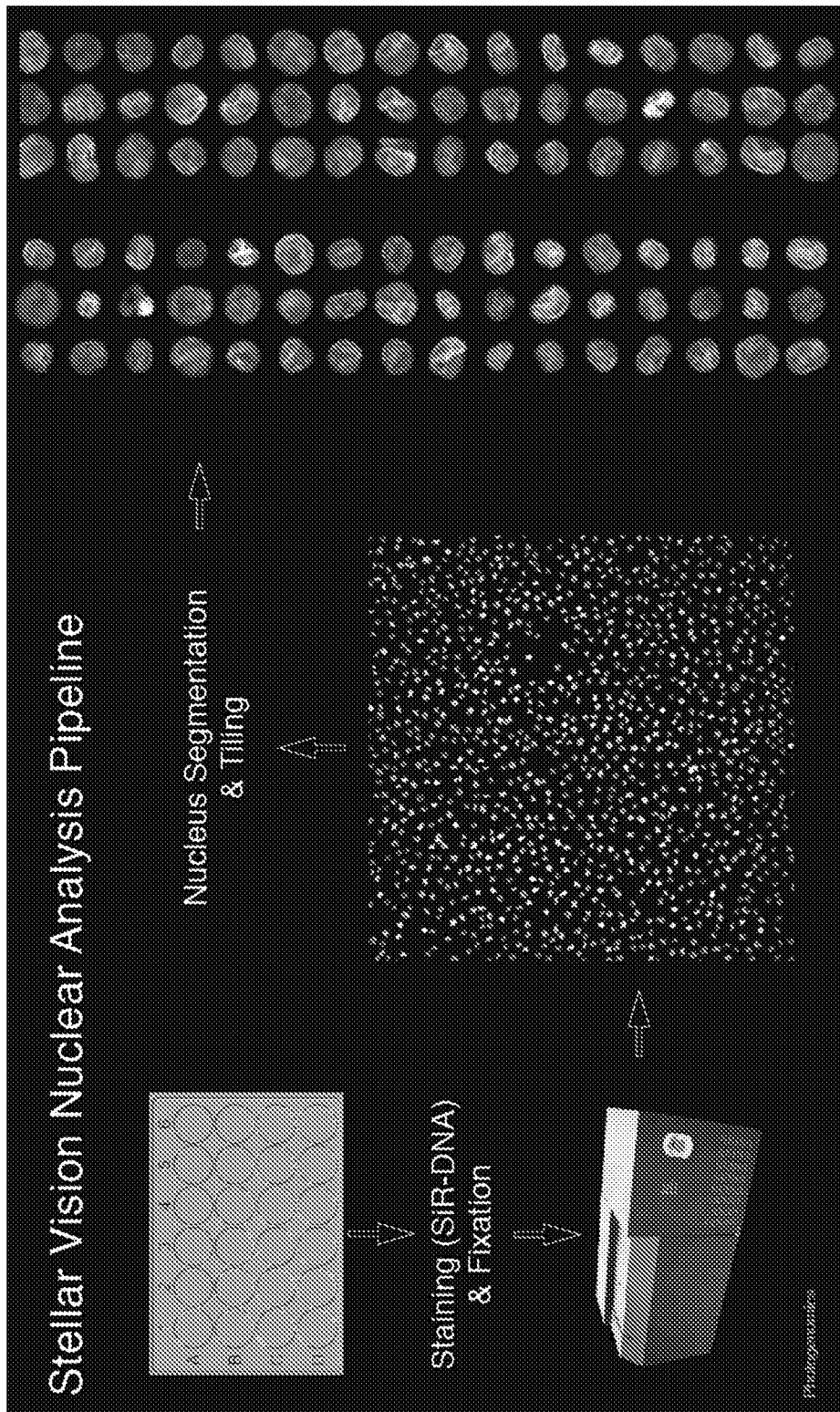
FIG. 11 provides a non-limiting illustration of a workflow for processing and analyzing images of cells or cell nuclei according to the methods disclosed herein. In this example, cells grown in microwell plates are stained and fixed prior to image capture using a super-resolution "Stellar Vision" fluorescence microscope. In this example, images of cell nuclei within each microwell are processed, segmented, and tiled to produce images of individual cell nuclei from which phenotypic data may be extracted.

FIG. 11 illustrates the initial workflow for image capture and processing used in these studies. Wild-type and knock-out K562 cells were grown in 24 well plates, stained using SiR-DNA stain, and imaged using the Stellar Vision fluorescence microscope as described above. The individual images were then processed to segment the images of individual cell nuclei and, if desired, tiled to create composite images.

Figure 12:
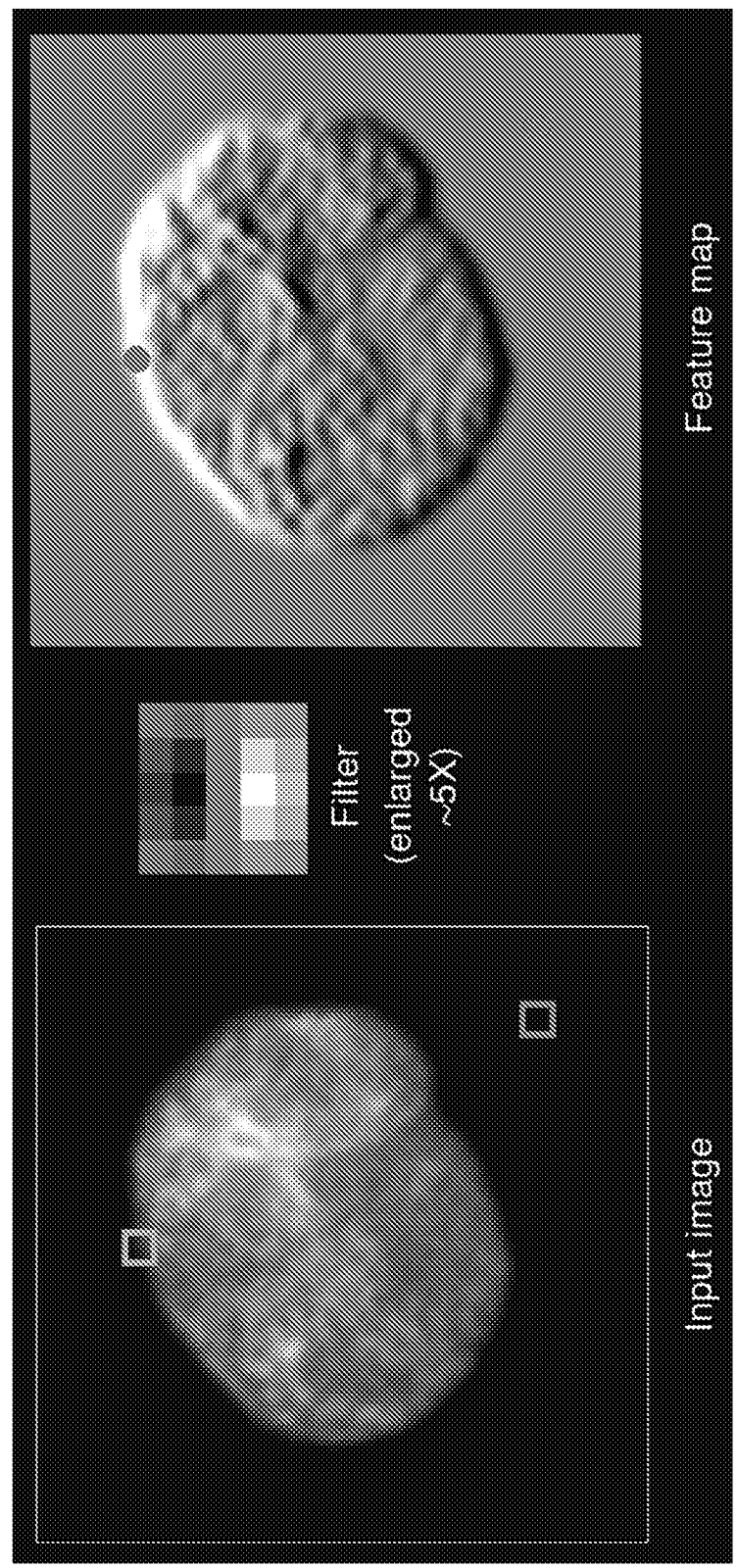
FIG. 12 illustrates an input cell nucleus image (left) and the feature map (right) obtained by processing the input image using a 5×5 pixel convolutional filter.

FIG. 12 illustrates an input cell nucleus image (left) and the feature map (right) obtained by processing the input image using a 5×5 pixel convolutional filter (center; enlarged representation shown). Convolutional filters are general purpose filters used in image processing and convolutional neural network algorithms for smoothing, sharpening, or feature extraction that, when applied to an input image, perform a mathematical operation on a matrix of image pixels, e.g., determining a new value of a central pixel by adding the weighted values of all neighboring pixels together. The two spots indicated in each image provide points of comparison for corresponding locations—one location being positioned in the background and one location comprising a specific location within the image of the cell nucleus.

Figure 13:
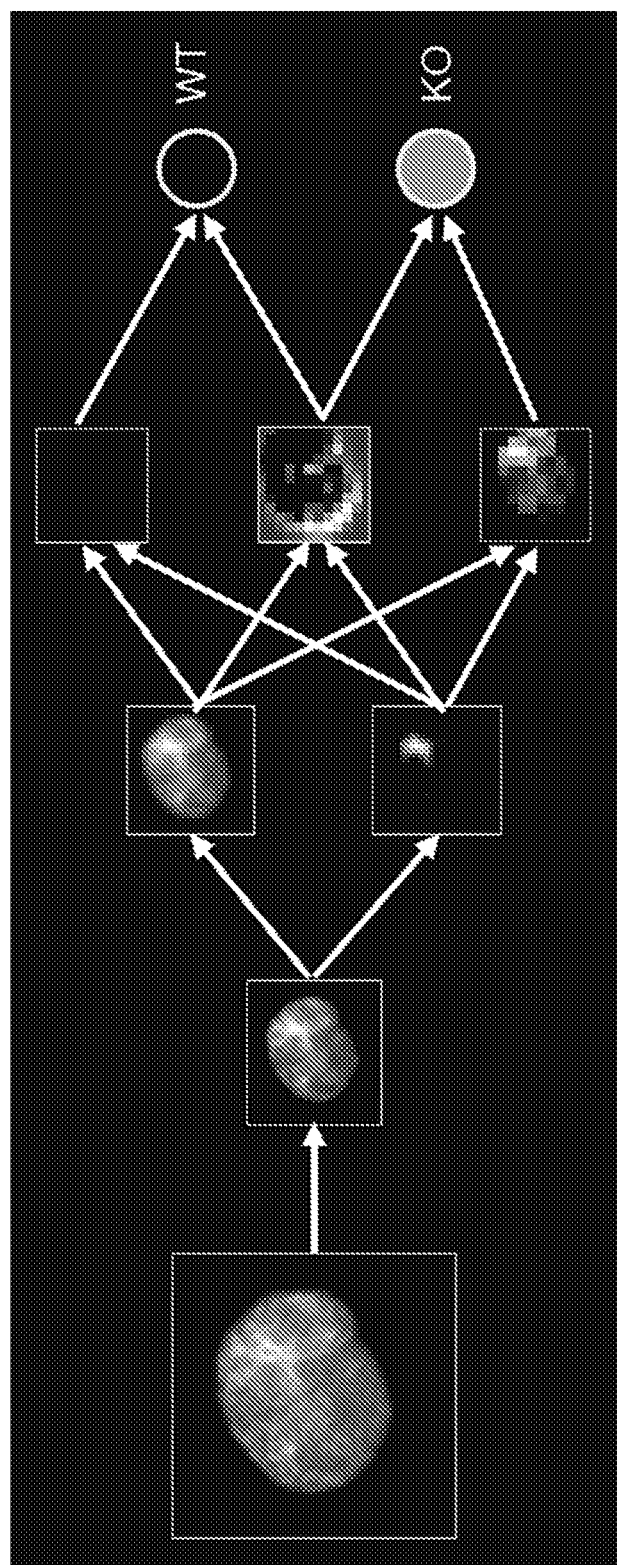
FIG. 13 illustrates the use of a convolutional neural network to classify images of single cell nuclei as either wild type (WT) or knock-out (KO) cells.

FIG. 13 illustrates the use of a convolutional neural network to classify images of single cell nuclei as either wild type (WT) or knock-out (KO) cells. Each layer of a convolutional neural network (CNN) performed a 5×5 pixel convolutional filtering operation on the input image data to generate successive feature maps. The convolution operation was performed using a strided approach in which the filters were stepped through the image in 2 pixel steps. The feature maps of the final layer were combined to determine image class. Convolutional filter coefficients and weighting factors for the final layer were learned using an labeled image data set. A separate CNN-based classifier was trained to differentiate each knock-out cell line from wild type controls.

Figure 14:
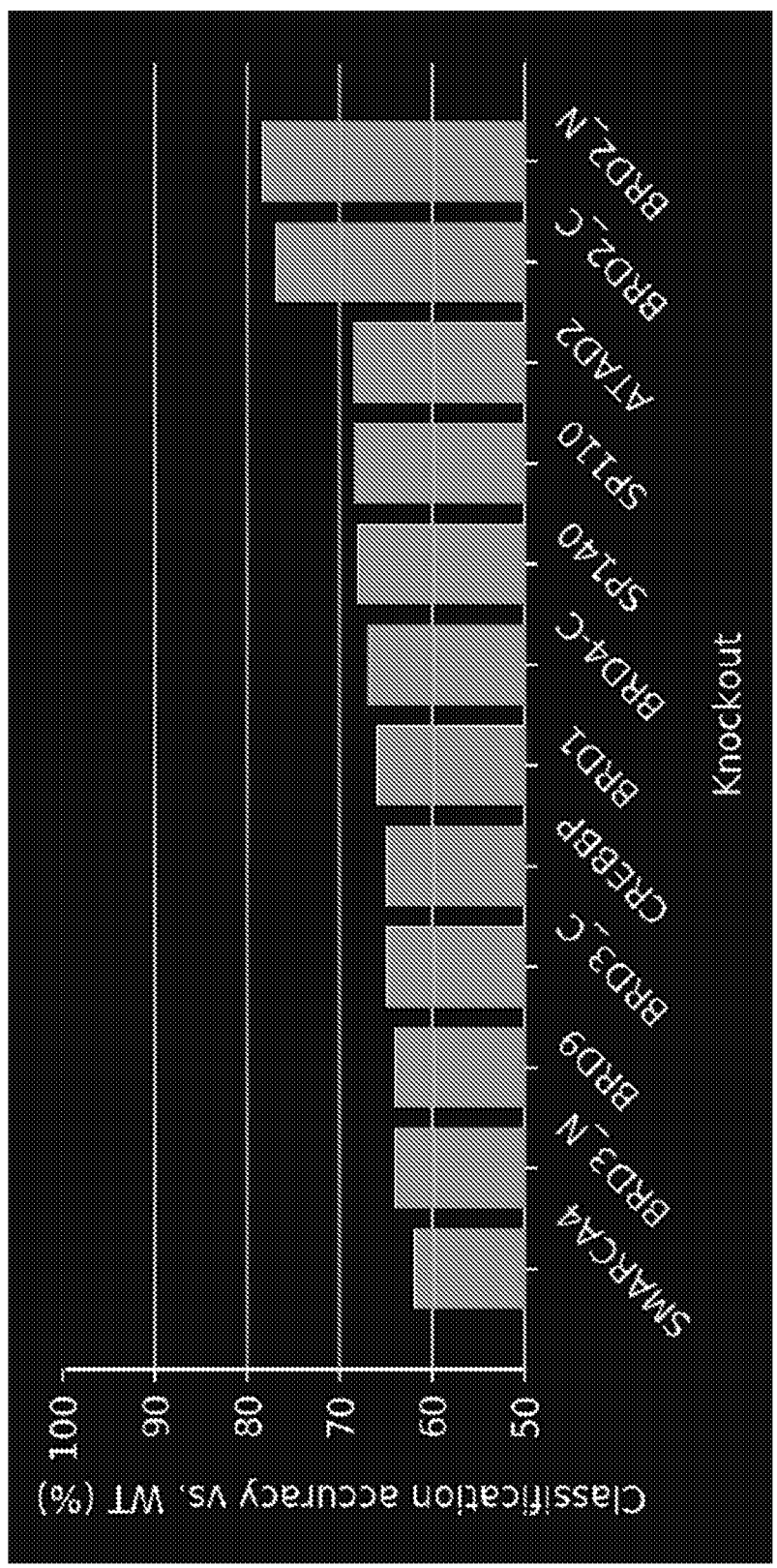
FIG. 14 provides a non-limiting example of classification accuracy data for use of a convolutional neural network to classify images of the nuclei of different types of knock-out cells versus images of the nuclei of wild type cells.

FIG. 14 provides an example of classification accuracy data obtained using the convolutional neural network to classify images of the nuclei of different types of knock-out cells versus images of the nuclei of wild type cells. The data indicate that in each case, the CNN-based classifier was able to distinguish between a knock-out cell line and wild-type cells with reasonable accuracy.

Figure 15:
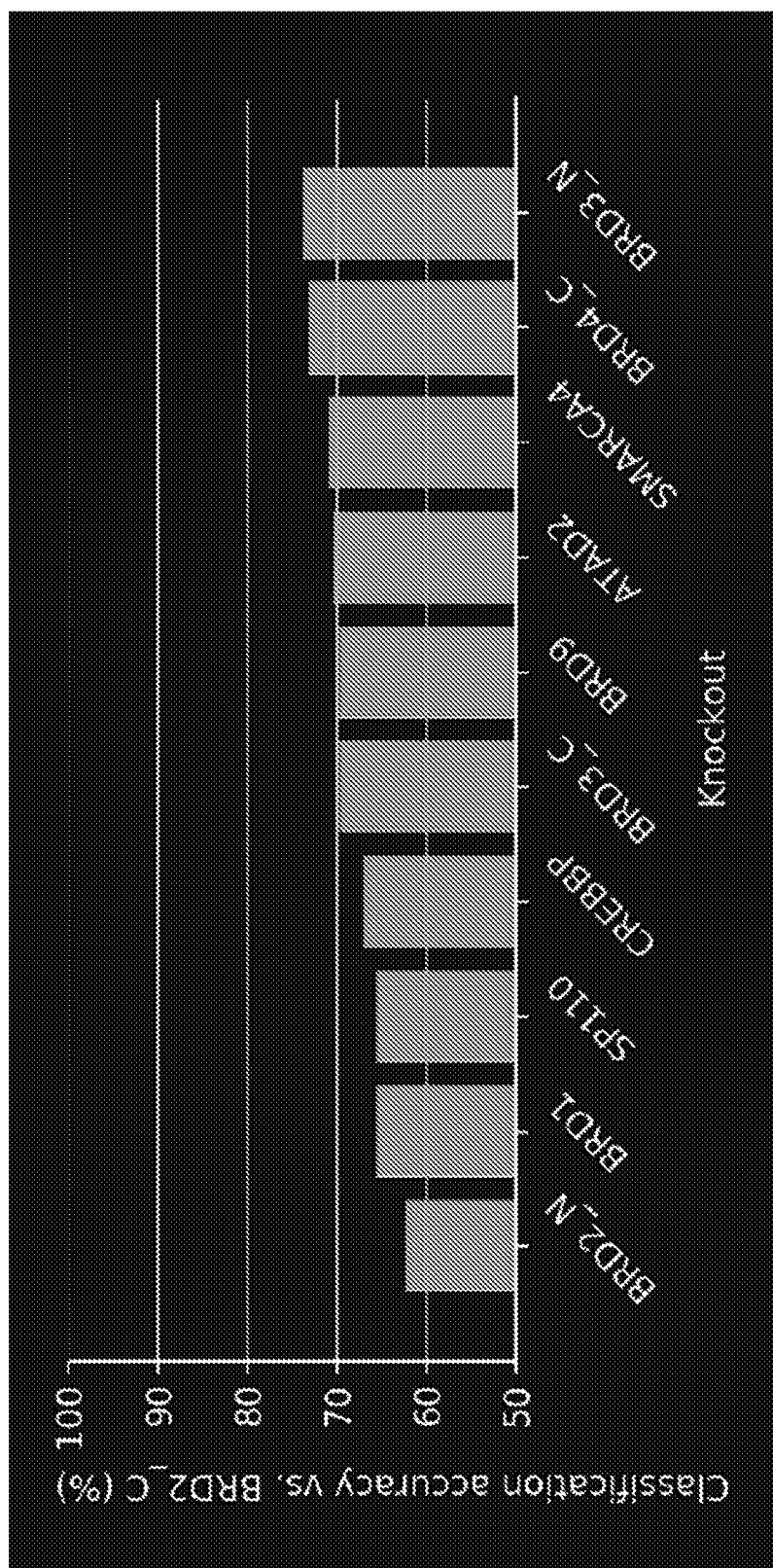
FIG. 15 provides a non-limiting example of classification accuracy data for use of a convolutional neural network to classify images of the nuclei of different types of knock-out cells versus images of the nuclei of BRD2_C knock-out cells.

FIG. 15 provides an example of classification accuracy data for use of the CNN-based classifier to classify images of the nuclei of different types of knock-out cells versus images of the nuclei of BRD2_C knock-out cells. The data indicate that in each case, the CNN-based classifier was able to distinguish between one knock-out cell line and another.

Figure 16:
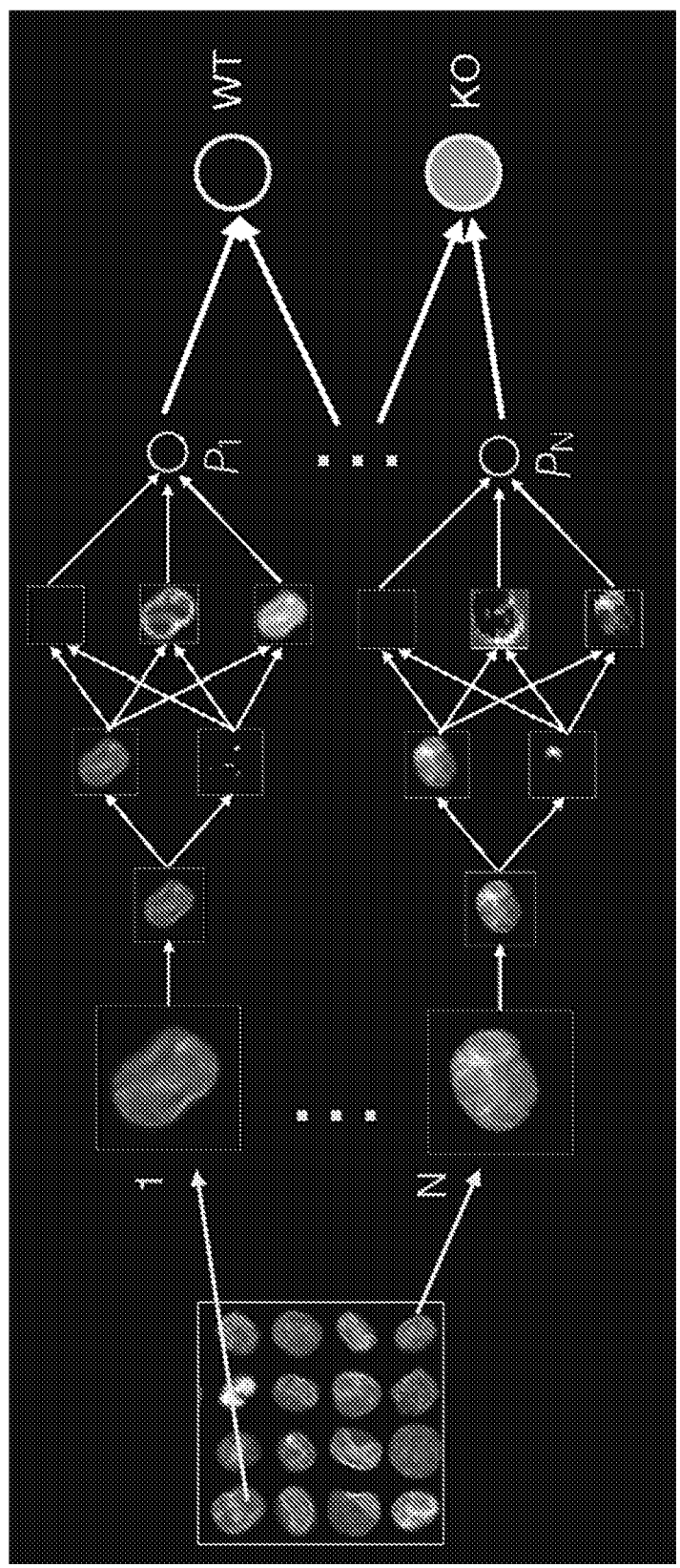
FIG. 16 illustrates the use of a convolutional neural network to classify images of pooled cell nuclei as belonging to either wild type (WT) or knock-out (KO) cells.

FIG. 16 illustrates the use of a convolutional neural network to classify images of pooled cell nuclei as belonging to either wild type (WT) or knock-out (KO) cells. The CNN-based classifier architecture and learned filter coefficients were taken from those learned in the single cell classifiers, and an additional layer ($P_1, P_2, \ldots, P_N$) was added to merge the outputs for single cell classification into an output (or classification decision) for the group.

Figure 17:
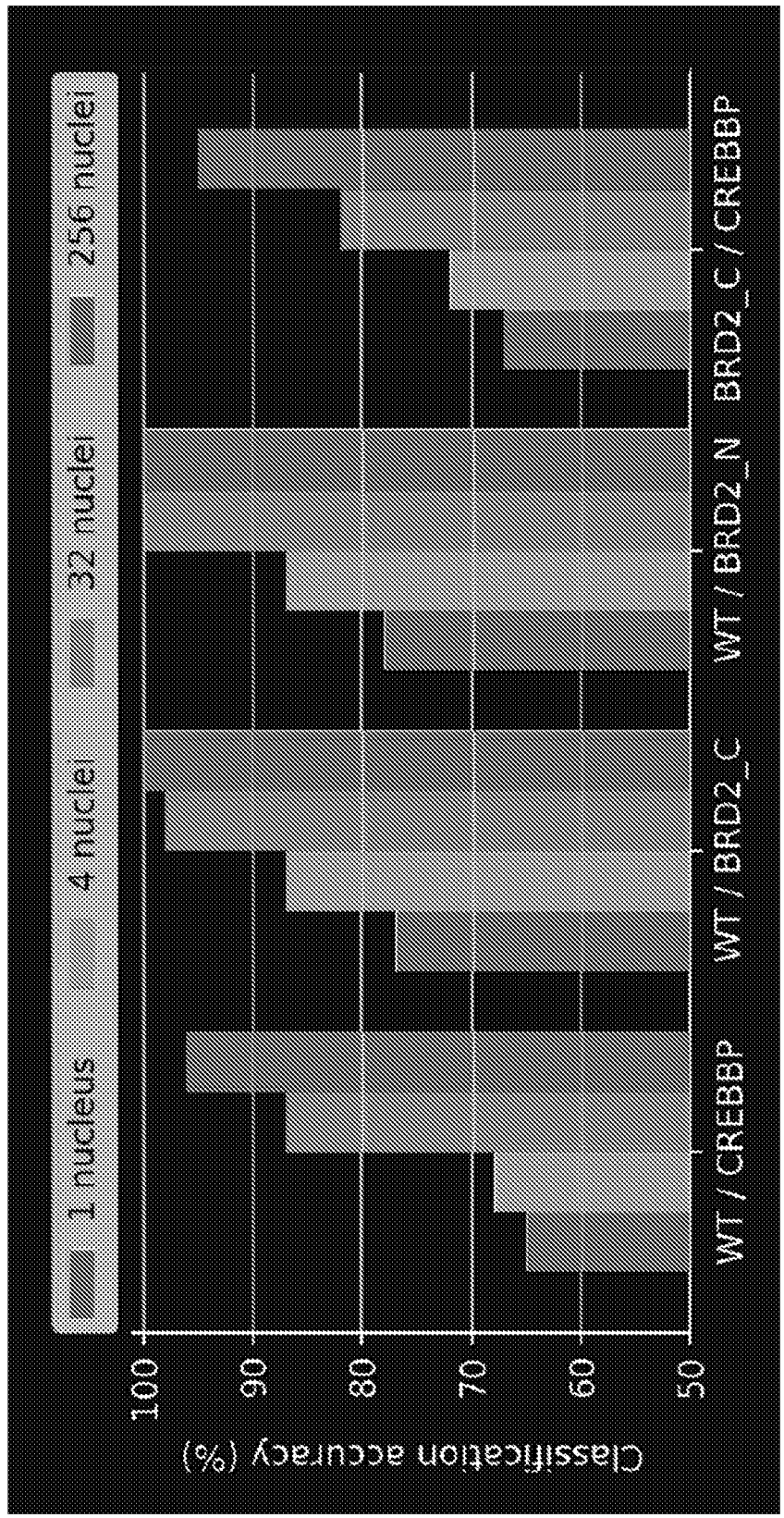
FIG. 17 provides a non-limiting example of classification accuracy data for use of a convolutional neural network to classify images of pooled cell nuclei as a function of the number of cell nuclei in the pool.

FIG. 17 provides an example of classification accuracy data for use of a CNN-based classifier to classify pooled images of cell nuclei as a function of the number of cell nuclei in the pool. Performing classification on pooled images comprising increasingly large numbers of individual cells led to improvements in accuracy approaching or reaching 100% accuracy.

Figure 18:
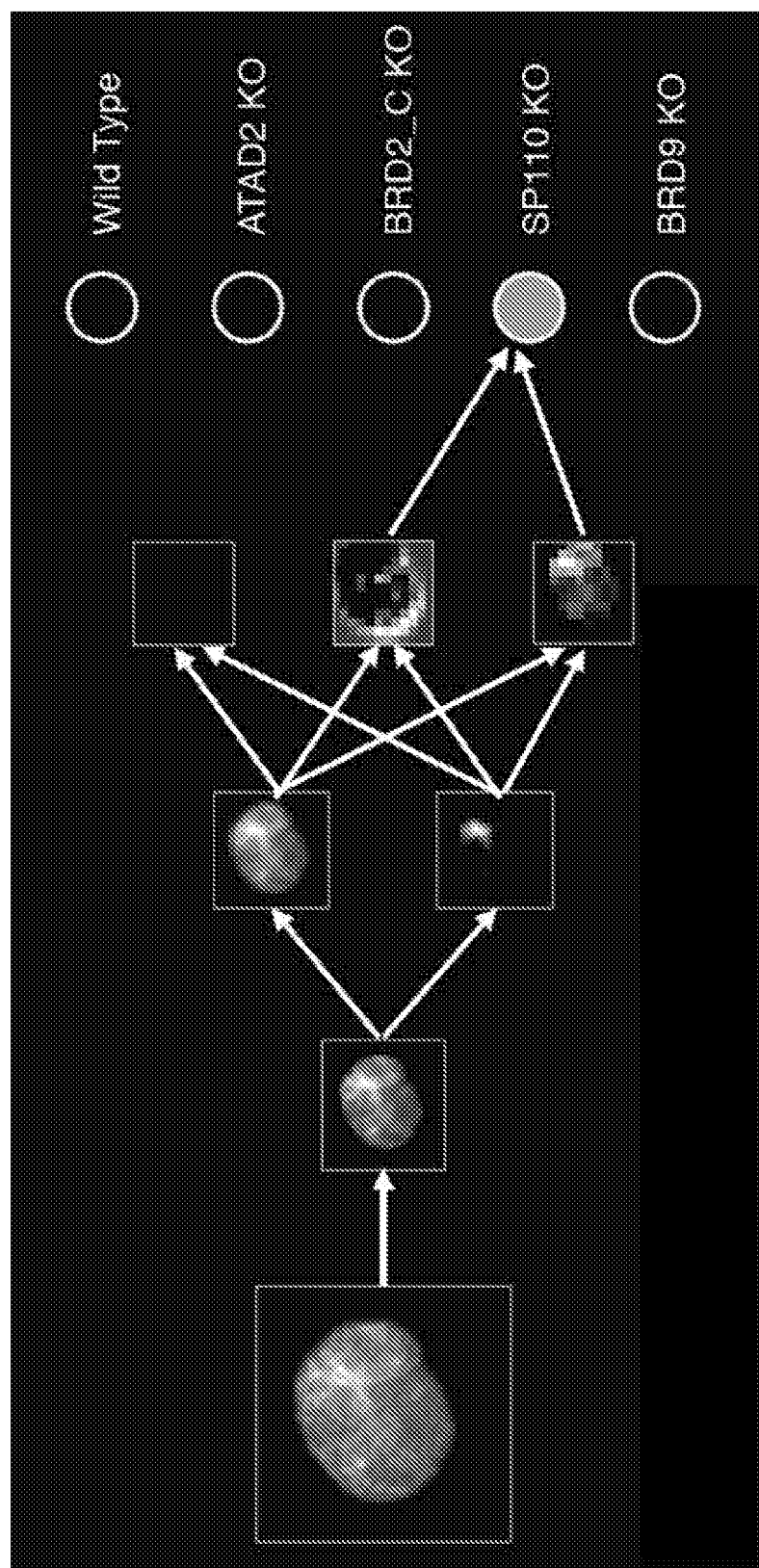
FIG. 18 illustrates the use of a pan-classifier based on a convolutional neural network to classify images of cell nuclei as having been derived from one of several different knock-out cell genotypes.

FIG. 18 illustrates the use of a multi-class or pan-classifier based on a convolutional neural network to classify images of cell nuclei as having been derived from one of several different knock-out cell genotypes. A CNN-based classifier comprising 12 output nodes was designed and trained to predict the most likely genotype for individual cells.

Figure 19:
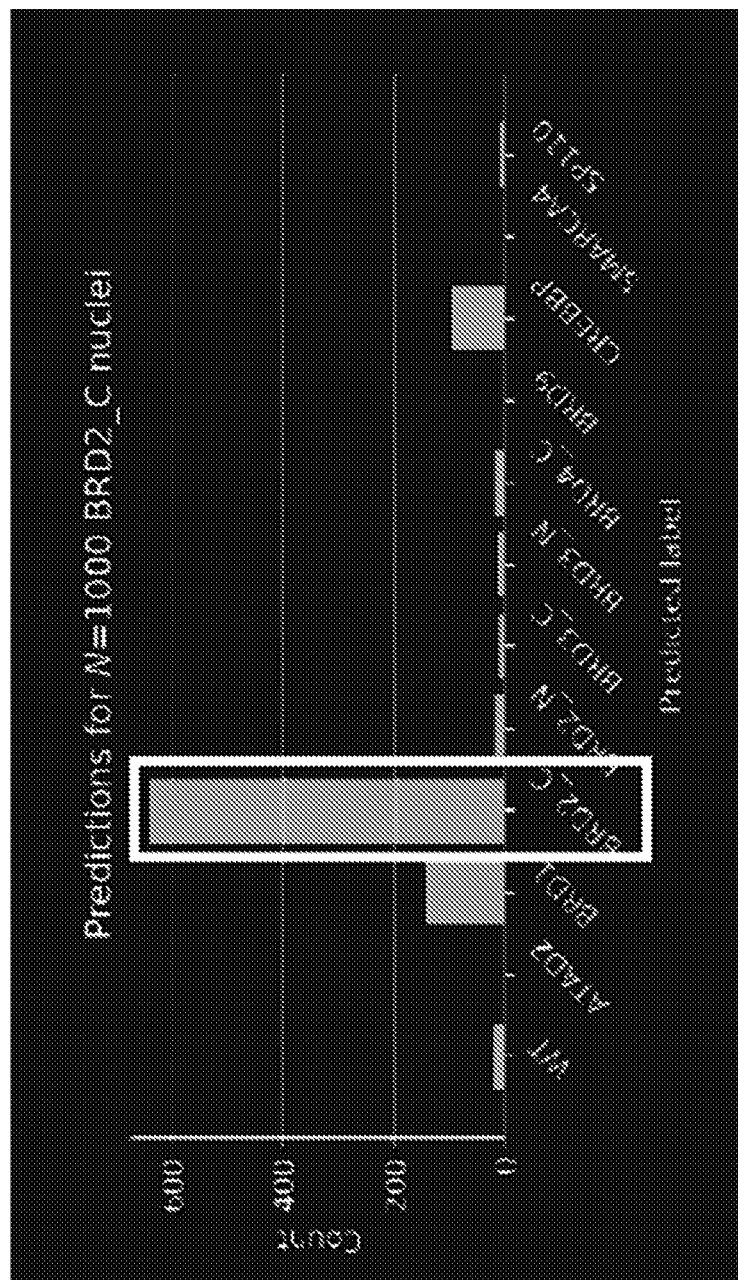
FIG. 19 provides a non-limiting example of classification prediction data for use of a multi-class convolutional neural network to classify BRD2_C nuclei.

FIG. 19 provides an example of classification prediction data for use of a multi-class convolutional neural network to classify BRD2_C nuclei. Predictions of genotype were made for 1,000 images of BRD2_C knock-out cell nuclei. A little over 600 of the nuclei were correctly assigned.

Figure 20:
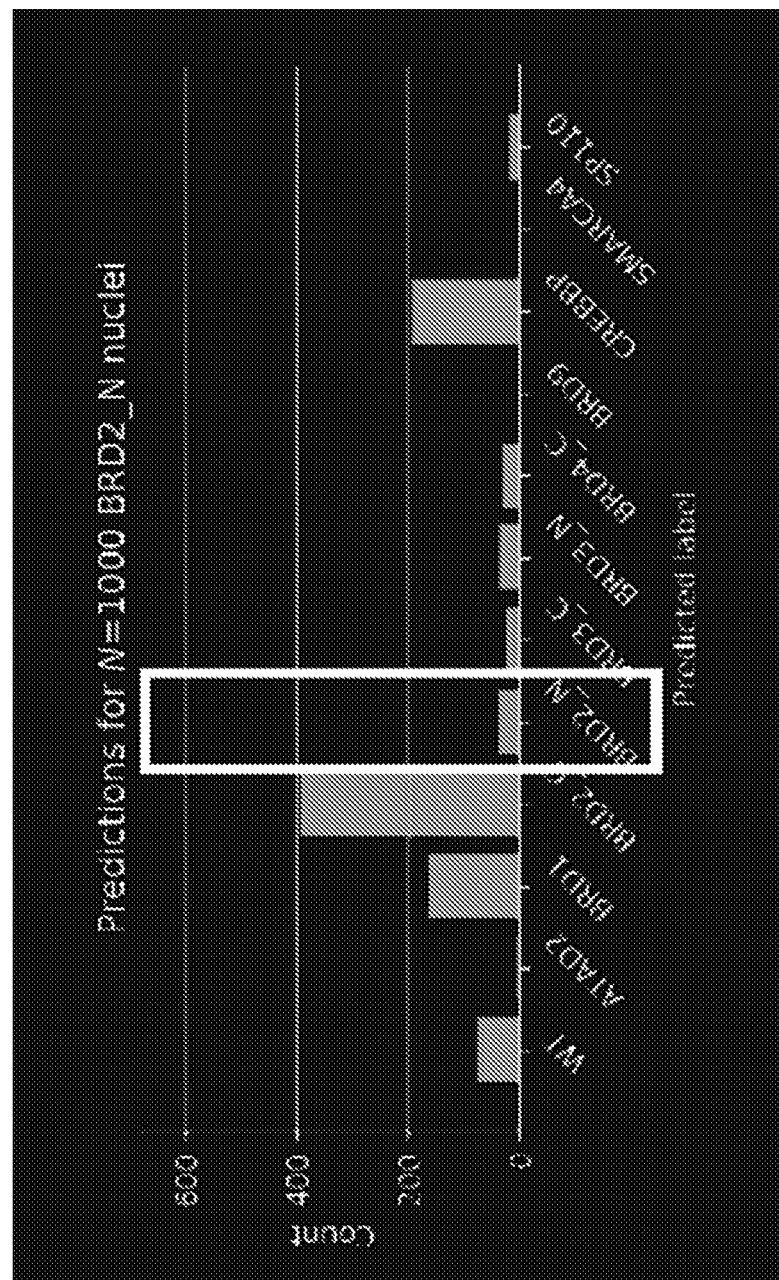
FIG. 20 provides a non-limiting example of classification prediction data for use of a multi-class convolutional neural network to classify BRD2 N nuclei.

FIG. 20 provides a non-limiting example of classification prediction data for use of a multi-class convolutional neural network to classify BRD2_N nuclei. Predictions of genotype were made for 1,000 images of BRD2_N knock-out cell nuclei. Only about 50 of the nuclei were correctly assigned. The performance of the CNN-based multi-class classifier varied widely for different cell line.

Figure 21:
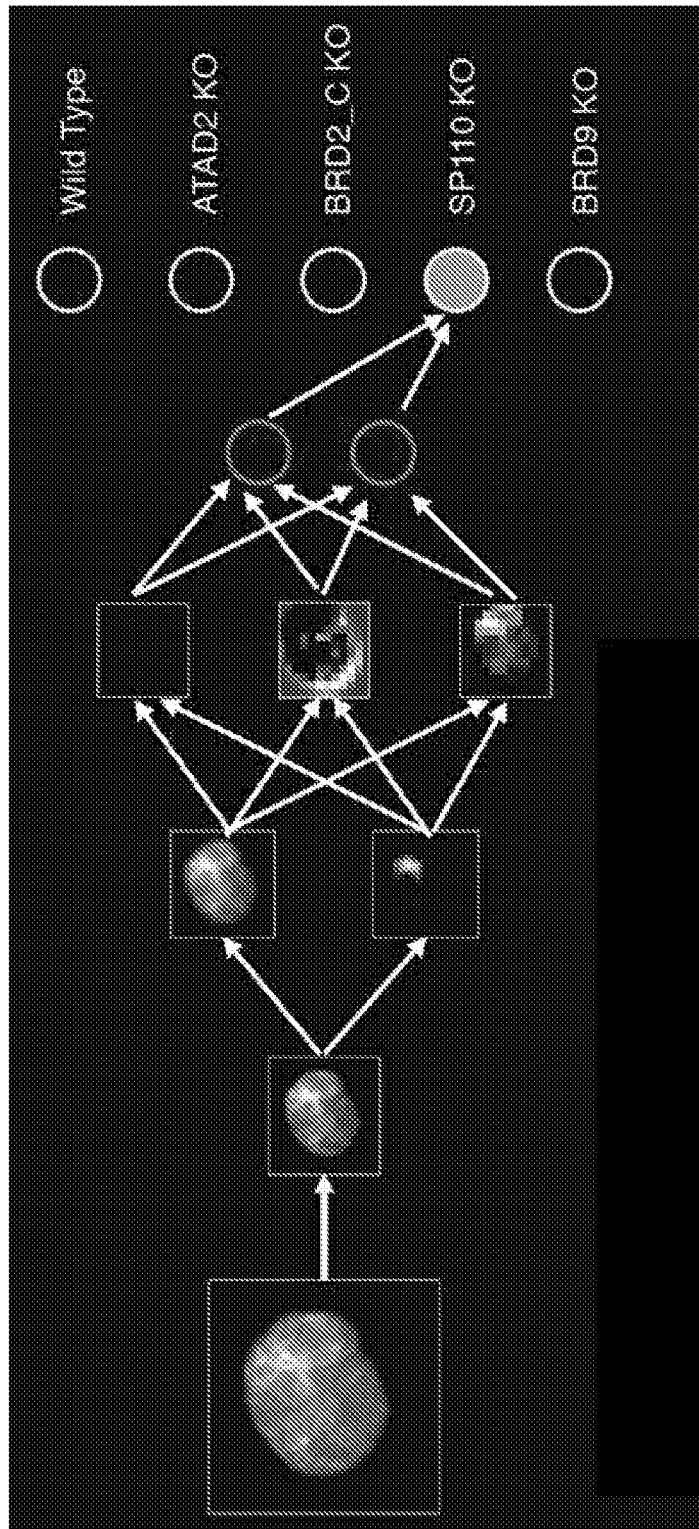
FIG. 21 illustrates a CNN-based classifier comprising an additional "2D latent space mapping" layer of nodes inserted prior to the final classification layer.

FIG. 21 illustrates a CNN-based classifier comprising an additional "2D latent space mapping" layer of nodes inserted prior to the final classification layer. The filters and model features learned by the multi-class network were retained, but a mapping layer comprising two nodes was inserted prior to the final layer used to determine class (genotype).

Figure 22:
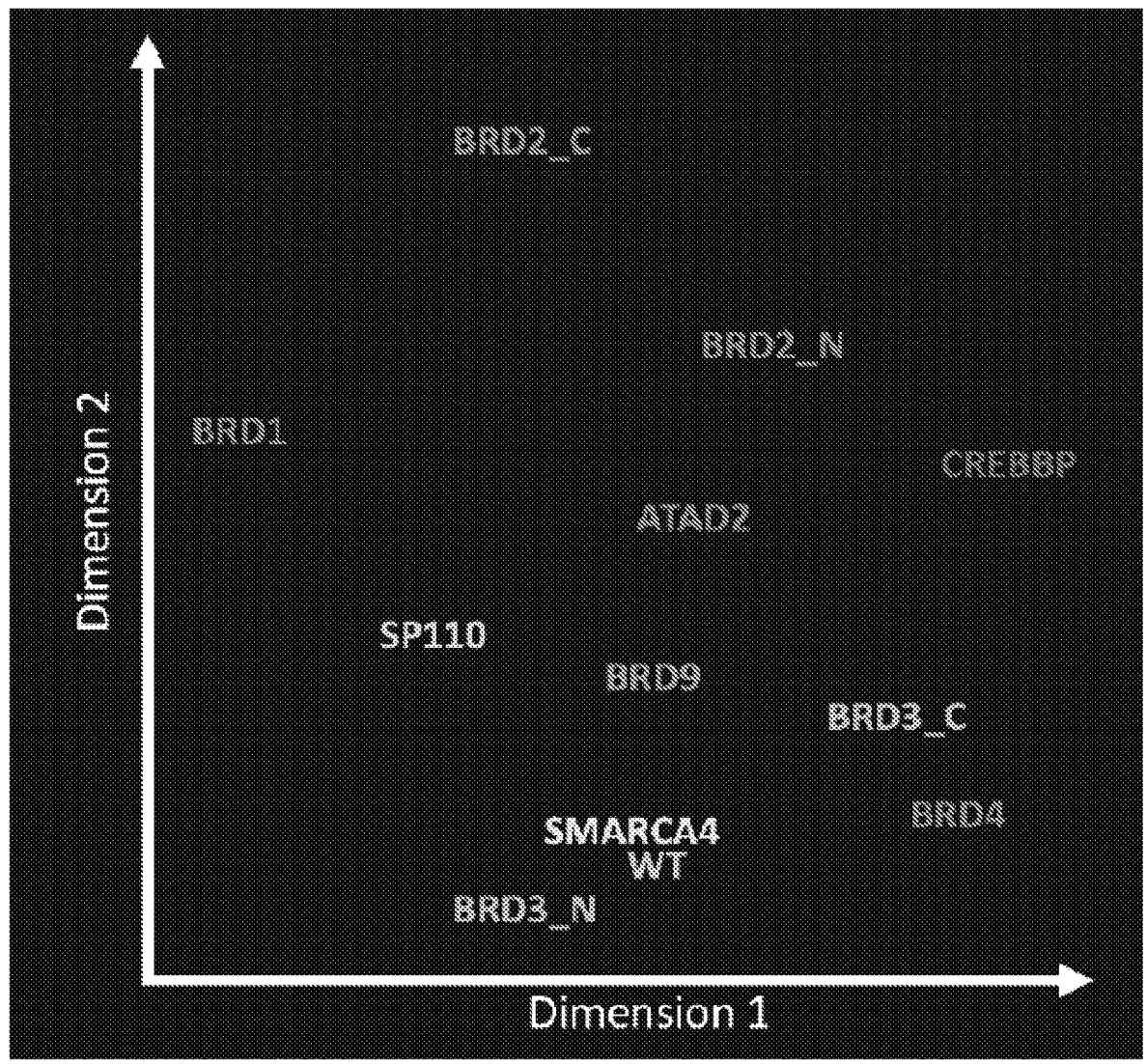
FIG. 22 provides a non-limiting example of data for classifying the images of cell nuclei for a variety of knock-out cell lines and mapping them to a two dimensional "latent" space.

FIG. 22 provides an example of data for classifying the images of cell nuclei for a variety of knock-out cell lines and mapping them to a two dimensional "latent" spaced defined by the two nodes of the layer immediately prior to the final classification layer. Pairs of knock-out cell lines that are easy to classify tend to be farther apart in the 2D latent space, however, the clusters of data overlap significantly (only the centroids of each data cluster is shown in the plot), and the "dimensions" are hard to interpret in terms of observable cell phenotypes.

Figure 23:
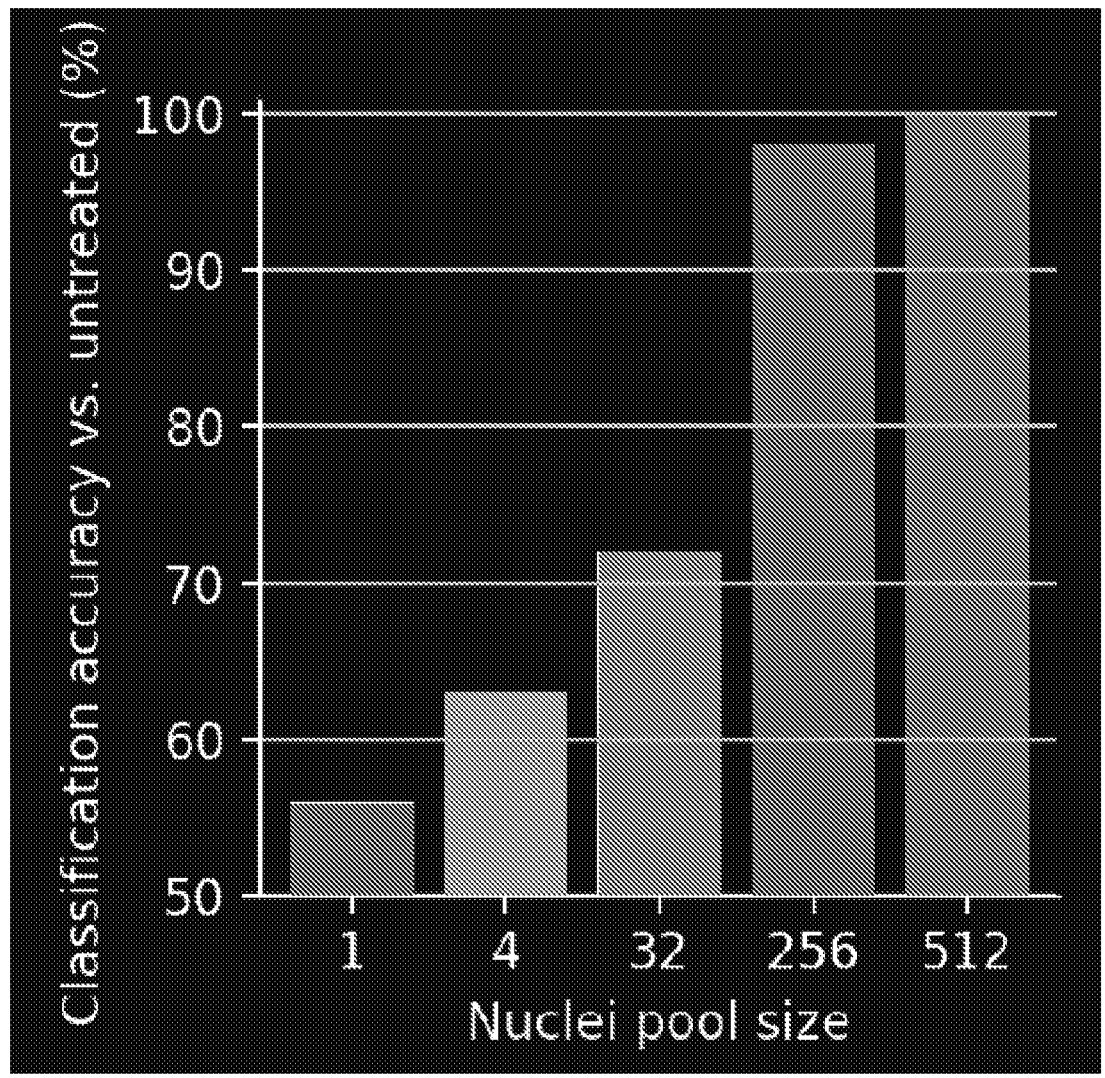
FIG. 23 provides a non-limiting example of classification accuracy for using a multi-class convolutional neural network to classify drug-treated cells as a function of the number of nuclei included in pooled images.

FIG. 23 provides an example of classification accuracy data for using a CNN-based classifier to classify drug-treated cells versus untreated cells as a function of the number of nuclei included in a pool of images. The drug-treated cells were treated with a BET (bromodomain and extra-terminal motif protein) inhibitor. Use of larger pools of cell nuclei resulted in significant improvements in classification accuracy.

Figure 24:
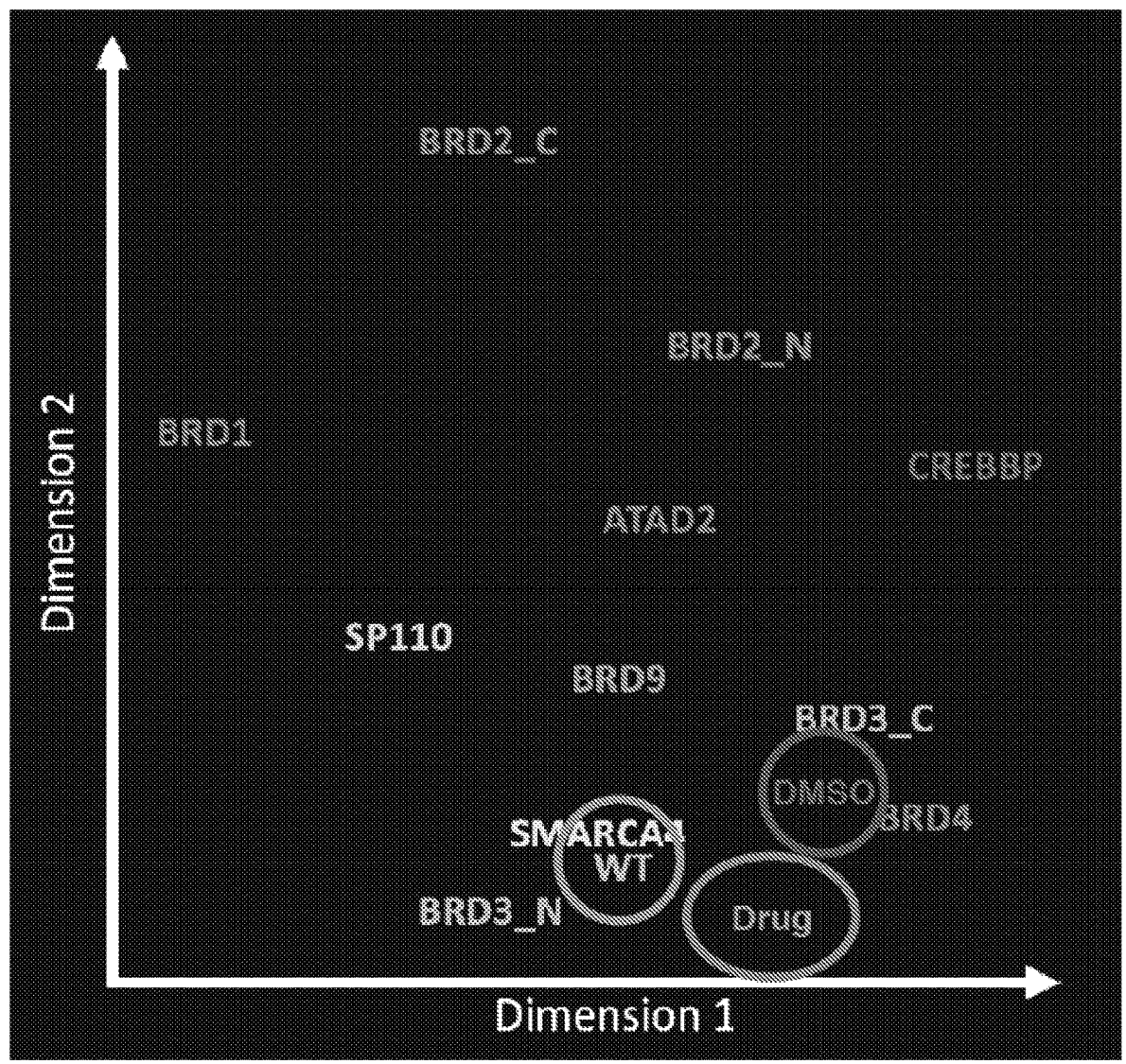
FIG. 24 provides a non-limiting example of data for classifying images of drug-treated, DMSO-treated, or wild-type cells and a variety of knock-out cell lines using a CNN-based classifier and mapping them to a two dimensional "latent" space.

FIG. 24 provides an example of data for classifying images of drug-treated, DMSO-treated, or wild-type cells and a variety of knock-out cell lines using a CNN-based classifier and mapping them to a two dimensional "latent" space. Drug-treated or DMSO-treated cells were somewhat distinguished from non-treated cells, while many of the bromodomain knock-out cell lines were mapped to significantly different coordinates in the two-dimensional space.

Example 4

Machine Learning for Correlating Cell Phenotype & Nucleic Acid Sequence Data—Design of Tissue-Restricted, Environmentally-Responsive Regulatory Elements In some cases, nucleic acid sequencing data may be used in conjunction with image data for training a machine learning algorithm to classify cells and/or determine a basis set of key attributes (i.e., a compressed representation of the input feature data) that may be used to characterize cells and identify correlations between specific cellular phenotypic traits and specific genetic or genomic traits. In some cases, such an approach may then allow one to use the machine learning algorithm to infer genetic or genomic traits of the imaged cells from an analysis of image data alone. Integrated analyses of imaging and sequence-based data using conventional techniques to provide coupled profiling of cells will lead to extremely large, multi-dimensional feature data sets (e.g., comprising not only sequence data but also image-derived feature data for millions of cells) that are complex and difficult to interpret. Machine learning methods such as those described herein may provide an alternative approach to simplify the data mining and interpretation process.

Figure 25:
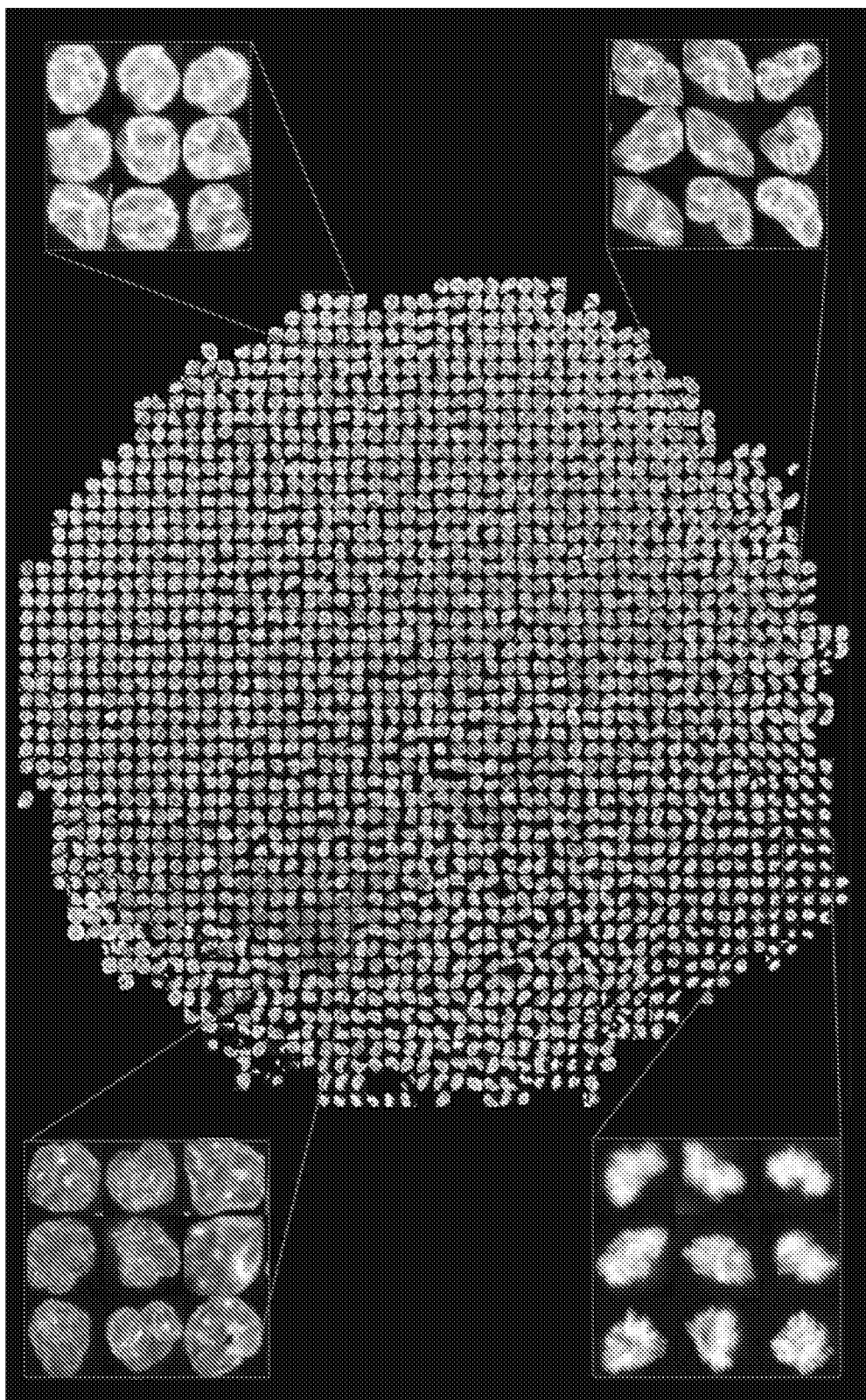
FIG. 25 provides an example of a composite image of single cell nuclei. The four inset figures provide magnified images of nuclei from distinct sub-populations of cells within the larger population represented in the composite image.

FIG. 25 provides an example of a composite image of single cell nuclei. The four inset figures provide magnified images of nuclei from distinct sub-populations of cells within the larger population represented in the composite image. As described above, machine learning-based analysis of such image data may be used to distinguish one or more sub-populations of cells, and in some instances may further allow one to infer genotypic or genomic traits of the cells based on observable or derived (i.e., latent) phenotypic traits of the sub-population.

Figure 26:
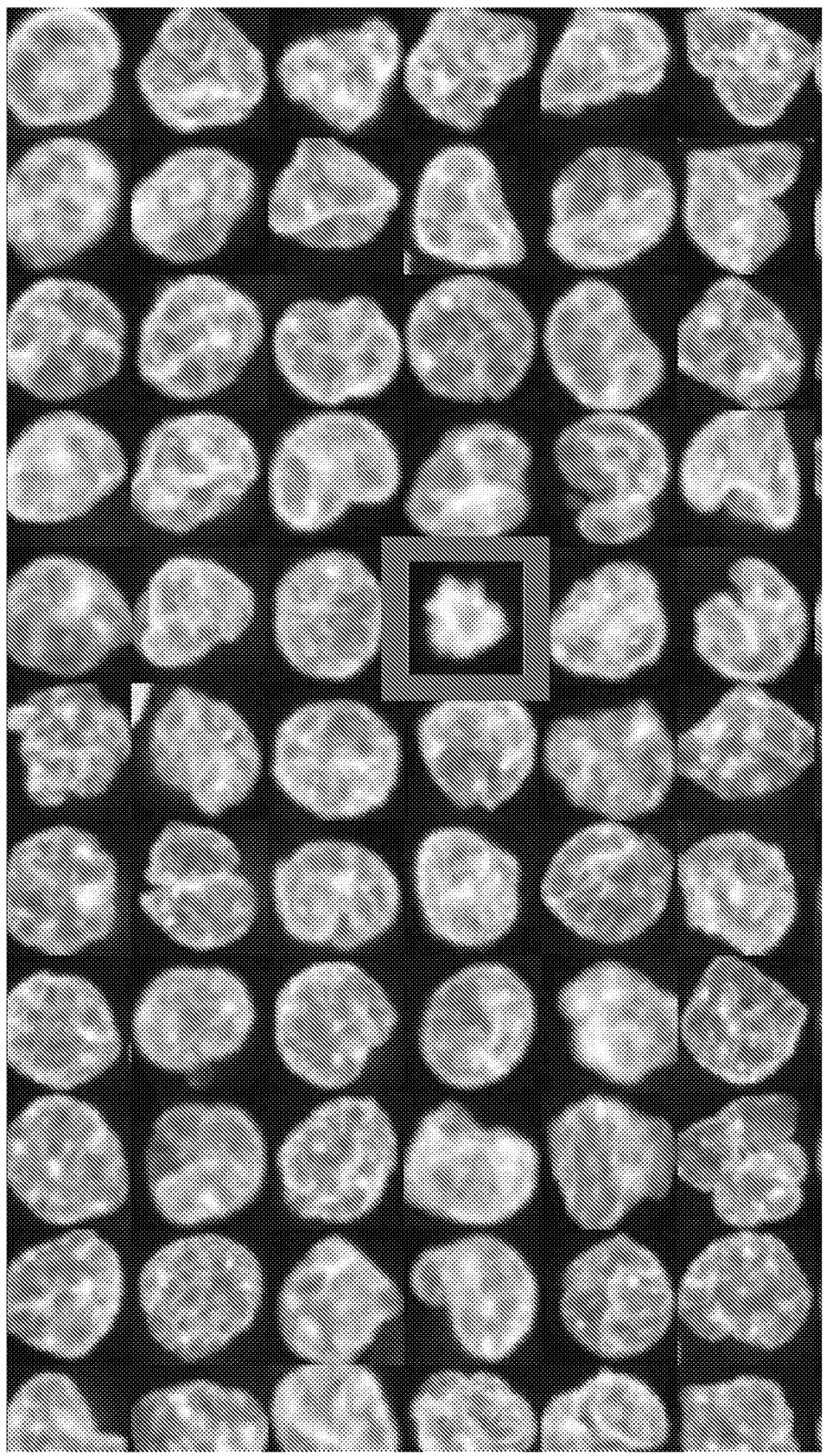
FIG. 26 provides an example of a composite image in which an example of an individual cell nucleus that exhibits markedly different phenotypic traits from those of the population at large is indicated within the box.

FIG. 26 provides an example of a composite image in which an example of an individual cell nucleus that exhibits markedly different phenotypic traits from those of the population at large is indicated within the box. As described above, machine learning-based analysis of such image data may be used to distinguish such individual cells from those of the population at large, and in some instances may further allow one to infer genotypic or genomic traits of individual cells based on observable or derived (i.e., latent) phenotypic traits of the individual cell.

Figure 27:
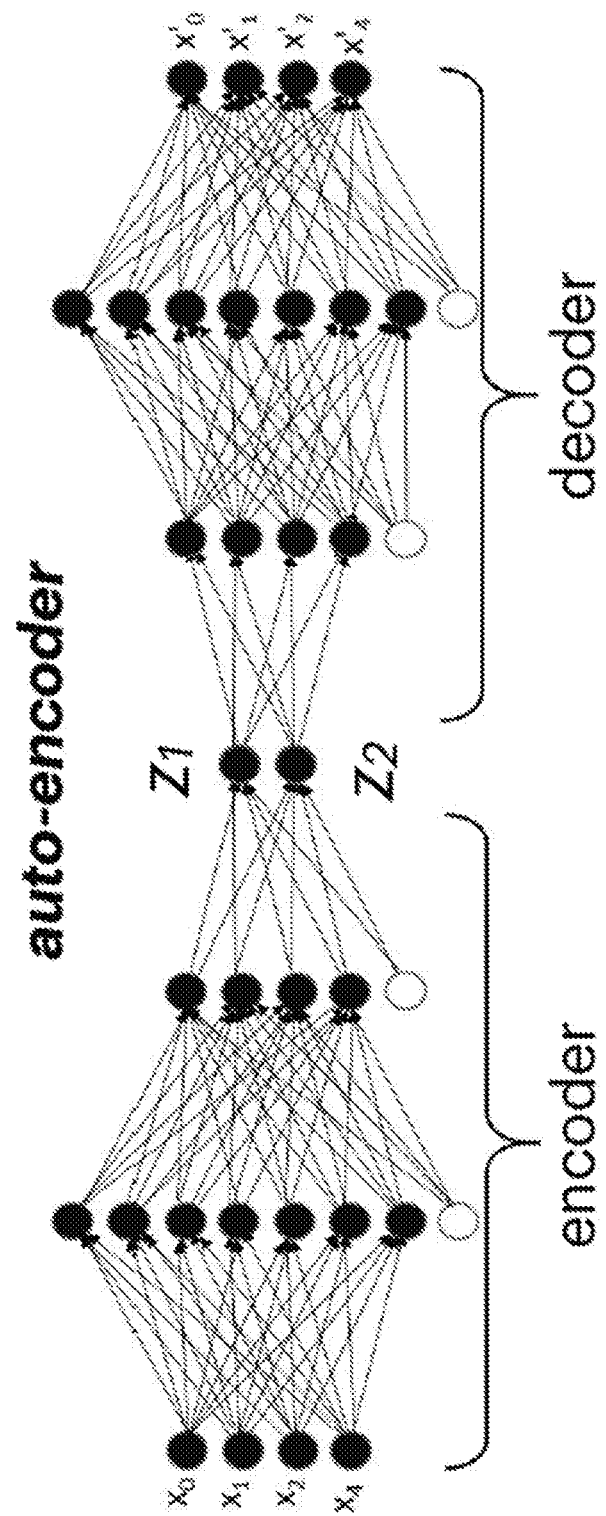
FIG. 27 illustrates the structure of an autoencoder, where the encoder maps input data comprising both cell nuclei image data and sequencing data to a minimal or basis set of latent parameters ($Z_1$, $Z_2$, etc.) that represent, for example, tissue-selectivity and environmental responsiveness properties.

FIG. 27 illustrates the structure of an autoencoder, where the encoder maps input data comprising both cell nuclei image data and sequencing data to a minimal or basis set of latent parameters ($Z_1$, $Z_2$, etc.) that represent, for example, tissue-selectivity and environmental responsiveness properties of a population of cells, a sub-population of cells, or individual cells. In some cases, the decoder portion of the autoencoder algorithm may then be used for generative modeling to predict the effects of small changes in one or more of the latent parameters $Z_1$, $Z_2$, ..., $ZN$ on, for example, cell phenotype, genotype, epigenotype, or genomic traits. In some cases, this capability may enable the design and synthesis of novel regulatory elements, e.g., regulatory elements (such as promoters, enhancers, or insulators) that do not otherwise existing in the genome, but that are predicted to behave in a certain manner both in terms of how cell-type specific they are, as well as in terms of how responsive they are to environmental changes, e.g., drug treatments. Such regulatory elements may have advantageous therapeutic properties in the treatment of cancer or other diseases.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. A method for characterizing a population of cells, the method comprising:
   a) acquiring a series of one or more images of a population of cells, wherein at least one image of the series comprises an image of one or more cells; and
   b) processing the series of one or more images using a statistical or machine learning algorithm, wherein the statistical or machine learning algorithm generates a cell characterization data set that comprises a basis representation of one or more key attributes of cells within the population of cells,
   wherein the statistical or machine learning algorithm comprises an unsupervised machine learning algorithm, and wherein the unsupervised machine learning algorithm comprises an artificial neural network, an association rule learning algorithm, a hierarchical clustering algorithm, a cluster analysis algorithm, a matrix factorization approach, a dimensionality reduction approach, or any combination thereof.

2. The method of claim 1, wherein the series of one or more images are acquired using phase contrast microscopy, fluorescence microscopy, super-resolution fluorescence microscopy, electron microscopy, or other super-resolution imaging technique.

3. The method of claim 1, wherein the processing steps further comprise applying a flat-field correction algorithm, a noise removal algorithm, an aberration correction algorithm, or any combination thereof to the images in each series of images.

4. The method of claim 1, wherein the processing steps further comprise applying one or more image processing algorithms to identify one or more regions of interest in the images of each series of images.

5. The method of claim 1, wherein the unsupervised machine learning algorithm is trained using a training data set that incorporates one or more constraints on cell population state.

6. The method of claim 1, wherein the unsupervised machine learning algorithm is trained using a training data set that incorporates nucleic acid sequencing data, gene expression profiling data, DNase I hypersensitivity assay data, or any combination thereof for one or more cells of the cell population.

7. The method of claim 6, wherein nucleic acid sequencing data or gene expression profiling data for one or more cells of the cell population is used as additional input for the statistical or machine learning algorithm.

8. The method of claim 1, wherein the unsupervised machine learning algorithm is continuously updated using new training data.

9. The method of claim 8, wherein the new training data is drawn from a training database that resides on the internet or in the cloud.

10. The method of claim 1, wherein the unsupervised machine learning algorithm comprises an artificial neural network, and wherein the artificial neural network comprises an autoencoder, a stacked autoencoder, a denoising autoencoder, a variational autoencoder, a deep learning neural network, a deep belief network, or any combination thereof.

11. The method of claim 1, further comprising making a cell classification decision based on the cell characterization data set.

12. The method of claim 11, wherein the cell characterization data set is used to (i) detect an effect of a change in environmental condition on cells of the population, (ii) detect an effect of an exposure to a chemical compound on cells of the population, or (iii) detect a disease state in cells of the population.

13. The method of claim 11, wherein the cell characterization data set is of lower dimensionality than that of image data used as input for the statistical or machine learning algorithm.

14. The method of claim 11, wherein the cell characterization data set comprises a representation of one or more key attributes of a single cell or of a sub-population of cells within the population.

15. The method of claim 1, wherein the one or more key attributes of the cells comprise one or more phenotypic traits, one or more genotypic traits, one or more epigenetic traits, one or more genomic traits, or any combination thereof.

16. The method of claim 15, wherein the one or more key attributes of the cells comprise one or more phenotypic traits and the one or more phenotypic traits comprise external shape, color, size, internal structure, patterns of distribution of one or more specific proteins, patterns of distribution of chromatin structure, glycosylated proteins, nucleic acid molecules, lipid molecules, glycosylated lipid molecules, carbohydrate molecules, metabolites, ions, or any combination thereof.

17. The method of claim 15, wherein the one or more key attributes of the cells comprise one or more genotypic traits and the one or more genotypic traits comprise a single nucleotide polymorphism (SNP), an insertion mutation, a deletion mutation, a repeat sequence, or any combination thereof.

18. The method of claim 15, wherein the one or more key attributes of the cells comprise one or more genomic traits and the one or more genomic traits comprise a gene expression level, a gene activation level, a gene suppression level, a chromatin accessibility level, or any combination thereof.

19. A method for screening drug candidates, the method comprising:
   a) acquiring a series of one or more images of a population of cells both before and after contacting the cells with a drug candidate, wherein at least one image of the series comprises an image of one or more cells;
   b) separately processing the series of one or more images acquired before and after the contacting step using a statistical or machine learning algorithm, wherein the statistical or machine learning algorithm generates a cell characterization data set for each series that comprises a basis representation of one or more key attributes of cells within the population of cells; and
   c) comparing the cell characterization data set for the population of cells after contacting with the drug candidate to that for the population of cells before contacting with the drug candidate, wherein detection of a change in the cell characterization data set indicates that the drug candidate activates or inactivates an intracellular signaling pathway that affects at least one key attribute of cells within the population of cells.

20. The method of claim 19, wherein the method further comprises:
   d) acquiring a series of one or more images of a population of cells both before and after independently contacting the cells with a plurality of drug candidates, wherein at least one image of the series comprises an image of one or more cells;
   e) separately processing the series of one or more images acquired before and after the independently contacting step for each drug candidate of the plurality of drug candidates using a statistical or machine learning algorithm, wherein the statistical or machine learning algorithm generates a cell characterization data set for each series that comprises a basis representation of one or more key attributes of cells within the population of cells;
   f) comparing the cell characterization data set for the population of cells after independently contacting the cells with the plurality of drug candidates to that for the population of cells before independently contacting the cells with the plurality of drug candidates, wherein detection of a change in the cell characterization data set indicates that a drug candidate of the plurality of drug candidates activates or inactivates an intracellular signaling pathway that affects at least one key attribute of cells within the population of cells; and
   g) selecting the drug candidate to be used as therapeutic drug based on a comparison of the characterization data set of the drug candidate with characterization data sets of the plurality of drug candidates.

\* \* \* \* \*